United States Patent
Ishida et al.

(10) Patent No.: US 9,771,351 B2
(45) Date of Patent: Sep. 26, 2017

(54) WNT SIGNALING INHIBITOR

(71) Applicant: KYOWA HAKKO KIRIN CO., LTD., Chiyoda-ku (JP)

(72) Inventors: Hiroshi Ishida, Sunto-gun (JP); Keiichi Motosawa, Sunto-gun (JP); Yusuke Miura, Sunto-gun (JP); Ryuichiro Nakai, Mishima (JP); Ryoko Okada, Yokohama (JP); Yuichi Takahashi, Mishima (JP)

(73) Assignee: KYOWA HAKKO KIRIN CO., LTD., Chiyoda-ku (JP)

( * ) Notice: Subject to any disclaimer, the term of this patent is extended or adjusted under 35 U.S.C. 154(b) by 0 days.

(21) Appl. No.: 14/908,945

(22) PCT Filed: Jul. 29, 2014

(86) PCT No.: PCT/JP2014/069872
§ 371 (c)(1),
(2) Date: Jan. 29, 2016

(87) PCT Pub. No.: WO2015/016195
PCT Pub. Date: Feb. 5, 2015

(65) Prior Publication Data
US 2016/0168125 A1     Jun. 16, 2016

(30) Foreign Application Priority Data

Jul. 29, 2013  (JP) .................... 2013-156458

(51) Int. Cl.
| C07D 401/14 | (2006.01) |
|---|---|
| C07D 475/00 | (2006.01) |
| C07D 405/14 | (2006.01) |
| C07D 413/14 | (2006.01) |
| C07D 471/04 | (2006.01) |
| C07D 487/04 | (2006.01) |

(Continued)

(52) U.S. Cl.
CPC ......... *C07D 401/14* (2013.01); *C07D 405/14* (2013.01); *C07D 413/14* (2013.01); *C07D 471/04* (2013.01); *C07D 475/00* (2013.01); *C07D 487/04* (2013.01); *C07D 491/052* (2013.01); *C07D 491/056* (2013.01); *C07D 498/04* (2013.01); *C07D 519/00* (2013.01)

(58) Field of Classification Search
None
See application file for complete search history.

(56) References Cited

U.S. PATENT DOCUMENTS 5,948,784 A * 9/1999 Fujiwara ............. C07D 401/14
                                                                        514/217.06
2009/0069319 A1    3/2009 Lundquist, IV et al.

(Continued)

FOREIGN PATENT DOCUMENTS

| CA | 2245896 | * 10/2003 |
|---|---|---|
| EP | 0 919 233 A1 | 6/1999 |

(Continued)

OTHER PUBLICATIONS

International Search Report and Written Opinion dated Sep. 16, 2014 in PCT/JP2014/069872 (English Translation only).
Yuji Nomoto et al., "Studies on Cardiotonic Agents. I. Synthesis of Some Quinazoline Derivatives", Chemical & Pharmaceutical Bulletin, vol. 38, No. 6, 1990, pp. 1591-1595.
Baozhi Chen et al., "Small Molecule—mediated Disruption of Wnt-dependent Signaling in Tissue Regeneration and Cancer", Nature Chemical Biology, vol. 5, No. 2, Feb. 2009, 8 pages.
Michael D. Shultz el al., "[1,2,4]Triazol-3-ylsulfanylmethyl)-3-phenyl-[1,2,4]oxadiazoles: Antagonists of the Wnt Pathway that Inhibit Tankyrases 1 and 2 via Novel Adenosine Pocket Binding", Journal of Medicinal Chemistry, vol. 55, 2012, pp. 1127-1136.
Shih-Min A. Huang et al., "Tankyrase Inhibition Stabilizes Axin and Antagonizes Wnt Signalling", Nature, vol. 461, Oct. 1, 2009, 7 pages.
Extended European Search Report dated Dec. 7, 2016 in Patent Application No. 14832281.1.
Andrey Voronkov, et al., "Wnt/beta-Catenin Signaling and Small Molecule Inhibitors" Current Pharmaceutical Design, vol. 19, XP002764558, pp. 634-664.

*Primary Examiner* — Anna Pagonakis
(74) *Attorney, Agent, or Firm* — Oblon, McClelland, Maier & Neustadt, L.L.P.

(57) ABSTRACT

A Wnt signaling inhibitor which comprises, as an active ingredient, a fused-ring heterocyclic compound represented by the following formula (IA) or a pharmaceutically acceptable salt thereof, and the like are provided:

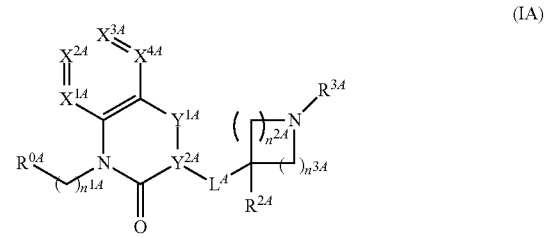

(IA)

(wherein, $n^{1A}$ represents 0 or 1; $n^{2A}$ and $n^{3A}$ may be the same or different, and each represents 1 or 2; $R^{OA}$ represents optionally substituted aryl or the like; $R^{2A}$ represents a hydrogen atom or the like; $R^{3A}$ represents an optionally substituted aromatic heterocyclic group or the like; $X^{1A}$, $X^{2A}$, $X^{3A}$ and $X^{4A}$ each represent CH or the like; $Y^{1A}$ represents $CH_2$ or the like; $Y^{2A}$ represents N or the like; and $L^A$ represents $CH_2$ or the like).

15 Claims, No Drawings

(51) Int. Cl.
*C07D 491/052* (2006.01)
*C07D 491/056* (2006.01)
*C07D 498/04* (2006.01)
*C07D 519/00* (2006.01)

(56) References Cited

U.S. PATENT DOCUMENTS

2011/0136813 A1 6/2011 Lum et al.
2012/0196851 A1 8/2012 Varrone et al.
2014/0038922 A1 2/2014 Lum et al.

FOREIGN PATENT DOCUMENTS

| JP | 2010-537998 A | 12/2010 |
| JP | 2011-521958 A | 7/2011 |
| WO | WO 96/06841 A1 | 3/1996 |
| WO | WO 97/29749 A1 | 8/1997 |
| WO | WO 2011/042145 A1 | 4/2011 |

\* cited by examiner

WNT SIGNALING INHIBITOR

CROSS-REFERENCE TO RELATED APPLICATIONS

This application is the U.S. National Stage of International Application No. PCT/JP2014/069872, filed Jul. 29, 2014. This application claims priority to Japanese Patent Application No. 2013-156458, filed Jul. 29, 2013.

TECHNICAL FIELD

The present invention relates to a fused-ring heterocyclic derivative or a pharmaceutically acceptable salt thereof, which has a Wnt signaling inhibitory activity, and is useful as a therapeutic and/or preventive agent for, for example, cancer, pulmonary fibrosis, fibromatosis, osteoarthritis, and the like, and the like.

BACKGROUND ART

In chemotherapy for cancer, various antitumor agents such as microtubule agonists such as taxanes, Vinca alkaloids and the like; topoisomerase inhibitors; alkylating agents and the like are used. These antitumor agents have various problems, for example, the types of cancer for which these antitumor agents can be used are limited, adverse effects such as myelotoxicity, neuropathy and the like are observed, drug-resistant tumors emerge, and the like (Nature Reviews Cancer 2003, 3, 502). Recently, a molecular targeted antitumor agent showing effectiveness against a specific type of cancer has been reported. Imatinib or gefitinib, which is a tyrosine kinase inhibitor, shows effectiveness also in chronic myeloid leukemia or non-small-cell lung cancer against which existing antitumor agents are ineffective. However, the types of cancer against which the agent shows effectiveness are limited, and also, a case where acquisition of resistance is observed has been reported (Nature Reviews Drug Discovery 2004, 3, 1001). Therefore, a novel antitumor agent in which such problems are improved has been demanded.

Wnt/β-catenin signaling is an important pathway associated with development, differentiation, and maintenance of living organisms (Nature Reviews Drug Discovery 2006, 5, 997). On the other hand, it is known that abnormal Wnt/β-catenin signaling is also associated with various diseases such as cancer and the like. In the absence of Wnt signaling, cytoplasmic β-catenin is kept at a low level. Axin and Adenomatous Polyposis Coli (APC) form a scaffold to accelerate the phosphorylation of intracellular β-catenin by casein kinase 1α (CK1α) and glycogen synthase kinase 3β (GSK3β). The phosphorylated β-catenin is ubiquitinated and degraded by proteasome. Due to this, β-catenin is kept at a low level, and therefore cannot play a role as a transcriptional activator. In the presence of a Wnt ligand, when the Wnt ligand binds to a Frizzled (Fzd) receptor and a low-density lipoprotein receptor-related protein (LRP) receptor, an Axin-APC-CK1α-GSK3β complex is inactivated through Deshevelled (Dv1). Dephosphorylated β-catenin is stable and is accumulated in cells and transferred to the nucleus, and then binds to a T-cell factor (Tcf)/lymphoid enhancer factor (Lef) family transcription factor. This transcription factor complex induces the transcriptional activation of various target genes associated with proliferation, survival, and differentiation of cells.

Abnormal activation of Wnt/β-catenin signaling has been reported in various tumor tissues. The activation of Wnt/β-catenin signaling in a tumor is associated with a gene mutation of a molecule constituting this signaling or an increase or decrease in the expression level of a gene product thereof (Nature Reviews Drug Discovery 2006, 5, 997, Nature Reviews Cancer 2008, 8, 387). For example, in large bowel cancer and familial adenomatous polyposis coli, an APC gene loss-of-function mutation has been reported. In large bowel cancer, hepatocellular carcinoma, hepatoblastoma, and medulloblastoma, an Axin gene loss-of-function mutation has been reported. In large bowel cancer, stomach cancer, hepatocellular carcinoma, hepatoblastoma, Wilms' tumor, ovarian cancer, and pancreatic cancer, a β-catenin gene gain-of-function mutation has been reported. In large bowel cancer, breast cancer, melanoma, head and neck cancer, non-small-cell lung cancer, stomach cancer, mesothelioma, and pancreatic cancer, an increase in the expression of a Wnt ligand has been reported. In large bowel cancer, breast cancer, head and neck cancer, stomach cancer, synovial sarcoma, and pancreatic cancer, an increase in the expression of a Fzd receptor has been reported. In mesothelioma, non-small-cell lung cancer, and cervical cancer, an increase in the expression of a Dvl family member has been reported. In large bowel cancer, breast cancer, stomach cancer, mesothelioma, non-small-cell lung cancer, prostate cancer, esophageal cancer, and leukemia, a decrease in the expression of a secreted frizzled-related protein (SFRP) family member, which is a Wnt ligand inhibitory factor, has been reported. In large bowel cancer, breast cancer, prostate cancer, lung cancer, bladder cancer, and mesothelioma, a decrease in the expression of a Wnt inhibitory factor (WIF) family member has been reported. The inhibition of Wnt/β-catenin signaling inhibits the proliferation of a cancer cell line in which Wnt/β-catenin signaling is activated in this manner (Cell 2002, 111, 241, Oncogene 2005, 24, 3054, Neoplasia 2004, 6, 7, Clinical Cancer Research 2003, 9, 1291, Cancer Research 2004, 64, 5385, Cancer Cell 2004, 5, 91, Proceedings of the National Academy of Sciences of the U.S. Pat. No. 2,004,101, 12682). Therefore, a molecule that inhibits Wnt/β-catenin pathway is considered to be promising as an antitumor agent. There has been a report that diseases other than cancer including pulmonary fibrosis, fibromatosis, and osteoarthritis are associated with Wnt/β-catenin signaling (The American Journal of Pathology 2003, 162, 1393, Proceedings of the National Academy of Sciences of the United States of America 2002, 99, 6973, Proceedings of the National Academy of Sciences of the U.S. Pat. No. 2,004,101, 9757). Therefore, a molecule that inhibits Wnt/β-catenin pathway is expected to be useful as a therapeutic agent in these fields.

As a compound that inhibits Wnt/β-catenin signaling, a tankyrase inhibitor has been reported (Nature 2009, 461, 614). Tankyrase belongs to the family of poly-(ADP-ribose) polymerases (PARP), and is also known as "PARP5" (Nature Reviews Molecular Cell Biology 2006, 7, 517). It has been reported that tankyrase binds to Axin which is associated with the degradation of cytoplasmic β-catenin to perform poly-ADP ribosylation, thereby accelerating the degradation of Axin (Nature 2009, 461, 614). It has been reported that a tankyrase inhibitor accelerates the degradation of β-catenin by stabilizing Axin and inhibits Wnt/β-catenin pathway, thereby inhibiting the proliferation of a cancer cell line in which Wnt/β-catenin signaling is activated (Nature 2009, 461, 614). Therefore, such a tankyrase inhibitor is expected to be useful as a therapeutic agent for a disease in which Wnt/β-catenin signaling is activated as described above.

On the other hand, it is known that a compound represented by the following formula (A) has an adenosine uptake activity (patent document 1).

[Chem. 1]

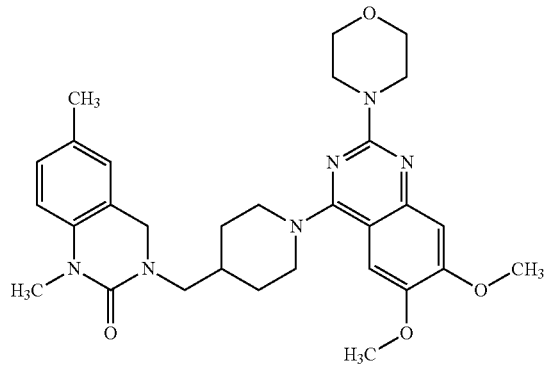

(A)

It is also known that a compound represented by the following formula (B) has a cardiotonic activity (non-patent document 1).

[Chem. 2]

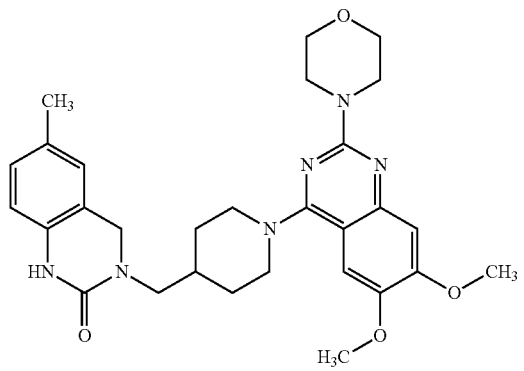

(B)

As a compound having a Wnt pathway inhibitory activity, a compound represented by the following formula (C) (non-patent document 2) is known.

[Chem. 3]

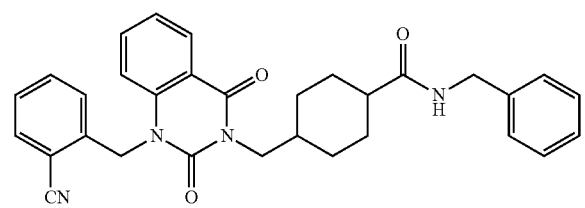

(C)

As a compound having a tankyrase inhibitory activity, a compound represented by the following formula (D) (non-patent document 3), a compound represented by the following formula (E) (non-patent document 4), and the like are known.

[Chem. 4]

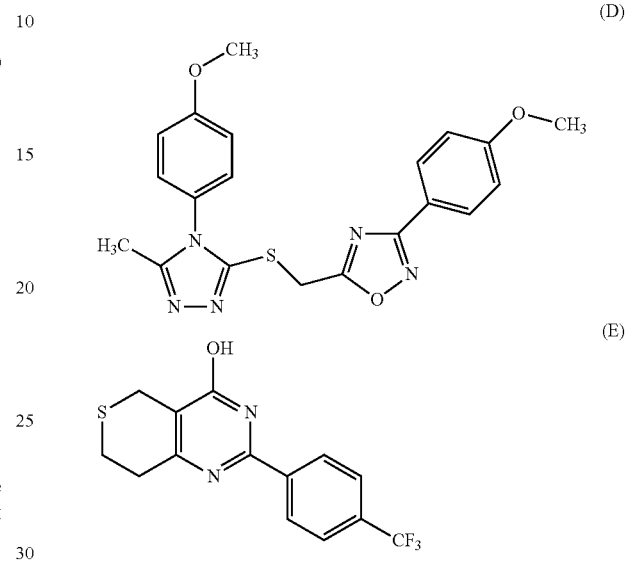

PRIOR ART DOCUMENTS

Patent Document patent document 1: WO96/06841

Non-Patent Documents non-patent document 1: Chemical and Pharmaceutical Bulletin (Chem. Pharm. Bull.), 1990, vol. 38, p. 1591
non-patent document 2: Nature Chemical Biology (Nat. Chem. Biol.), 2009, vol. 5, p. 100
non-patent document 3: Journal of Medicinal Chemistry (J. Med. Chem.), 2012, vol. 55, p. 1127
non-patent document 4: Nature, 2009, vol. 461, p. 61

SUMMARY OF INVENTION

Problems to be Solved by the Invention

An object of the present invention is to provide a fused-ring heterocyclic compound or a pharmaceutically acceptable salt thereof, which has a Wnt signaling inhibitory activity, and is useful as a therapeutic and/or preventive agent for, for example, cancer, pulmonary fibrosis, fibromatosis, osteoarthritis, and the like, and the like.

Means of Solving the Problems

The present invention relates to the following (1) to (35).
(1) A Wnt signaling inhibitor, comprising, as an active ingredient, a fused-ring heterocyclic compound represented by the general formula (IA) or a pharmaceutically acceptable salt thereof:

[Chem. 5]

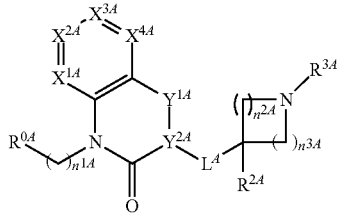

(IA)

[wherein $n^{1A}$ represents 0 or 1;

$n^{2A}$ and $n^{3A}$ may be the same or different, and each represents 1 or 2;

$R^{0A}$ represents a hydrogen atom, optionally substituted aryl, an optionally substituted aromatic heterocyclic group or an optionally substituted aliphatic heterocyclic group;

$R^{2A}$ represents a hydrogen atom or hydroxy;

$R^{3A}$ represents an optionally substituted aromatic heterocyclic group or an optionally substituted aliphatic heterocyclic group;

$X^{1A}$, $X^{2A}$, $X^{3A}$, and $X^{4A}$ may be the same or different, and each represents N or $CR^{4A}$ (wherein $R^{4A}$ represents a hydrogen atom, lower alkyl, cyano, halogen, hydroxy, lower alkoxy, lower alkanoyl or lower alkylsulfonyl);

$Y^{1A}$ represents $CH_2$ or $C(=O)$;

$Y^{2A}$ represents CH or N; and $L^A$ represents $CH_2$ or NH].

(2) A fused-ring heterocyclic compound represented by the general formula (I) or a pharmaceutically acceptable salt thereof:

[Chem. 6]

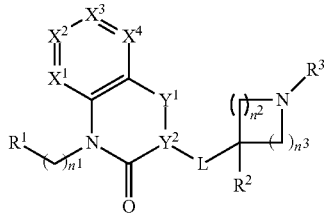

(I)

[wherein $n^1$ represents 0 or 1;

$n^2$ and $n^3$ may be the same or different, and each represents 1 or 2;

$R^1$ represents optionally substituted aryl, an optionally substituted aromatic heterocyclic group or an optionally substituted aliphatic heterocyclic group;

$R^2$ represents a hydrogen atom or hydroxy;

$R^3$ represents an optionally substituted aromatic heterocyclic group or an optionally substituted aliphatic heterocyclic group;

$X^1$, $X^2$, $X^3$, and $X^4$ may be the same or different, and each represents N or $CR^4$ (wherein $R^4$ represents a hydrogen atom, lower alkyl, cyano, halogen, hydroxy, lower alkoxy, lower alkanoyl or lower alkylsulfonyl);

$Y^1$ represents $CH_2$ or $C(=O)$;

$Y^2$ represents CH or N; and

L represents $CH_2$ or NH].

(3) The compound or the pharmaceutically acceptable salt thereof according to (2), wherein $n^2$ and $n^3$ are each 2.

(4) The compound or the pharmaceutically acceptable salt thereof according to (2) or (3), wherein $Y^2$ is N, and L is $CH_2$.

(5) The compound or the pharmaceutically acceptable salt thereof according to any one of (2) to (4), wherein $Y^1$ is $CH_2$.

(6) The compound or the pharmaceutically acceptable salt thereof according to any one of (2) to (5), wherein $n^1$ is 0.

(7) The compound or the pharmaceutically acceptable salt thereof according to any one of (2) to (6), wherein $R^1$ is (i) optionally substituted aryl, in which the aryl is phenyl, or (ii) an optionally substituted aromatic heterocyclic group, in which the aromatic heterocyclic group is pyridyl, pyridonyl or pyrimidinyl.

(8) The compound or the pharmaceutically acceptable salt thereof according to any one of (2) to (7), wherein $R^1$ is optionally substituted aryl or an optionally substituted aromatic heterocyclic group, and the group is a group represented by the following formula (a1):

[Chem. 7]

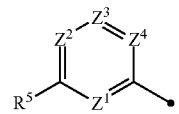

(a1)

[wherein $R^5$ represents a hydrogen atom, $C_{1-10}$ alkyl which may be substituted with hydroxy, $C_{1-10}$ alkoxycarbonyl, $C_{2-11}$ alkanoyl, $C_{1-10}$ alkylsulfonyl, $-NR^{6a}R^{6b}$ (wherein $R^{6a}$ and $R^{6b}$ may be the same or different, and each represents a hydrogen atom, $C_{2-11}$ alkanoyl or $C_{1-10}$ alkyl), $-CONR^{6c}R^{6d}$ (wherein $R^{6c}$ and $R^{6d}$ may be the same or different, and each represents a hydrogen atom or $C_{1-10}$ alkyl), $-SO_2NR^{6e}R^{6f}$ (wherein $R^{6e}$ and $R^{6f}$ may be the same or different, and each represents a hydrogen atom or $C_{1-10}$ alkyl), halogen, cyano, carboxy or nitro, and $Z^1$, $Z^2$, $Z^3$ and $Z^4$ may be the same or different, and each represents N or $CR^7$ (wherein $R^7$ represents a hydrogen atom, carboxy or halogen)], or a group represented by the following formula (a2):

[Chem. 8]

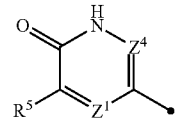

(a2)

(wherein $R^5$, $Z^1$ and $Z^4$ have the same definitions as described above, respectively).

(9) The compound or the pharmaceutically acceptable salt thereof according to (8), wherein $R^5$ is cyano, $-CONH_2$ or $-SO_2NH_2$.

(10) The compound or the pharmaceutically acceptable salt thereof according to (8), wherein $R^5$ is cyano.

(11) The compound or the pharmaceutically acceptable salt thereof according to any one of (8) to (10), wherein $R^7$ is a hydrogen atom or a fluorine atom.

(12) The compound or the pharmaceutically acceptable salt thereof according to any one of (2) to (11), wherein $R^3$ is an optionally substituted aromatic heterocyclic group.
(13) The compound or the pharmaceutically acceptable salt thereof according to (12), wherein the aromatic heterocyclic group is a bicyclic aromatic heterocyclic group.
(14) The compound or the pharmaceutically acceptable salt thereof according to (12), wherein the aromatic heterocyclic group is quinazolinyl.
(15) The compound or the pharmaceutically acceptable salt thereof according to any one of (2) to (11), wherein $R^3$ is an optionally substituted aliphatic heterocyclic group.
(16) A pharmaceutical composition, comprising, as an active ingredient, the compound or the pharmaceutically acceptable salt thereof described in any one of (2) to (15).
(17) A Wnt signaling inhibitor, comprising, as an active ingredient, the compound or the pharmaceutically acceptable salt thereof described in any one of (2) to (15).
(18) The Wnt signaling inhibitor according to (1) or (17), wherein the Wnt signaling inhibition is Wnt signaling inhibition by tankyrase inhibition.
(19) A therapeutic and/or preventive agent for a disease associated with Wnt signaling, comprising, as an active ingredient, the compound or the pharmaceutically acceptable salt thereof described in any one of (1) to (15).
(20) The agent according to (19), wherein the disease associated with Wnt signaling is cancer, pulmonary fibrosis, fibromatosis or osteoarthritis.
(21) A method for inhibiting Wnt signaling, comprising administering an effective amount of a fused-ring heterocyclic compound represented by the general formula (IA) or a pharmaceutically acceptable salt thereof:

[Chem. 9]

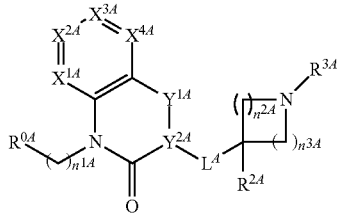

(IA)

(wherein $n^{1A}$, $n^{2A}$, $n^{3A}$, $R^{0A}$, $R^{2A}$, $R^{3A}$, $X^{1A}$, $X^{2A}$, $X^{3A}$, $X^{4A}$, $Y^{1A}$, $Y^{2A}$, and $L^A$ have the same definitions as described above, respectively).
(22) A method for inhibiting Wnt signaling, comprising administering an effective amount of the compound or the pharmaceutically acceptable salt thereof described in any one of (2) to (15).
(23) The method according to (21) or (22), wherein the method for inhibiting Wnt signaling is a method for inhibiting Wnt signaling by tankyrase inhibition.
(24) A method for treating and/or preventing a disease associated with Wnt signaling, comprising administering an effective amount of the compound or the pharmaceutically acceptable salt thereof described in any one of (2) to (15) and (21).
(25) The method according to (24), wherein the disease associated with Wnt signaling is cancer, pulmonary fibrosis, fibromatosis or osteoarthritis.
(26) A fused-ring heterocyclic compound represented by the general formula (IA) or a pharmaceutically acceptable salt thereof for use in Wnt signaling inhibition:

[Chem. 10]

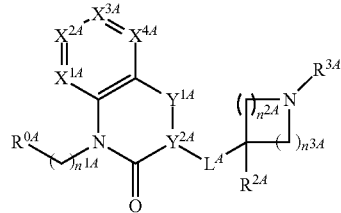

(IA)

(wherein $n^{1A}$, $n^{2A}$, $n^{3A}$, $R^{0A}$, $R^{2A}$, $R^{3A}$, $X^{1A}$, $X^{2A}$, $X^{3A}$, $X^{4A}$, $Y^{1A}$, $Y^{2A}$ and $L^A$ have the same definitions as described above, respectively).
(27) The compound or the pharmaceutically acceptable salt thereof described in any one of (2) to (15) for use in Wnt signaling inhibition.
(28) The compound or the pharmaceutically acceptable salt thereof according to (26) or (27), wherein the Wnt signaling inhibition is Wnt signaling inhibition by tankyrase inhibition.
(29) The compound or the pharmaceutically acceptable salt thereof described in any one of (2) to (15) and (26) for use in the treatment and/or prevention of a disease associated with Wnt signaling.
(30) The compound or the pharmaceutically acceptable salt thereof according to (29), wherein the disease associated with Wnt signaling is cancer, pulmonary fibrosis, fibromatosis or osteoarthritis.
(31) Use of a fused-ring heterocyclic compound represented by the general formula (IA) or a pharmaceutically acceptable salt thereof for the manufacture of a Wnt signaling inhibitor:

[Chem. 11]

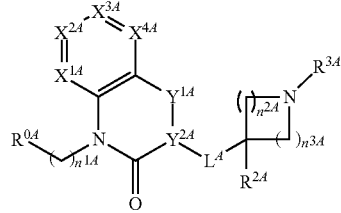

(IA)

(wherein $n^{1A}$, $n^{2A}$, $n^{3A}$, $R^{0A}$, $R^{2A}$, $R^{3A}$, $X^{1A}$, $X^{2A}$, $X^{3A}$, $X^{4A}$, $Y^{1A}$, $Y^{2A}$ and $L^A$ have the same definitions as described above, respectively).
(32) Use of the compound or the pharmaceutically acceptable salt thereof described in any one of (2) to (15) for the manufacture of a Wnt signaling inhibitor.
(33) The use of the compound or the pharmaceutically acceptable salt thereof according to (31) or (32), wherein the Wnt signaling inhibition is Wnt signaling inhibition by tankyrase inhibition.
(34) Use of the compound or the pharmaceutically acceptable salt thereof described in any one of (2) to (15) and (31) for the manufacture of a therapeutic and/or preventive agent for a disease associated with Wnt signaling.
(35) The use according to (34), wherein the disease associated with Wnt signaling is cancer, pulmonary fibrosis, fibromatosis or osteoarthritis.

Effects of Invention

A fused-ring heterocyclic compound or a pharmaceutically acceptable salt thereof according to the present invention has a Wnt signaling inhibitory activity and is useful as a therapeutic and/or preventive agent for, for example, cancer, pulmonary fibrosis, fibromatosis, osteoarthritis, and the like.

MODE FOR CARRYING OUT THE INVENTION

Hereinafter, a compound represented by the general formula (I) is referred to as Compound (I). The compounds having the other formula numbers are referred to in the same manner.

In the definitions of the respective groups in the general formula (I) and the general formula (IA), examples of the lower alkyl; the lower alkyl moieties of the lower alkoxy, the lower alkanoyl and the lower alkylsulfonyl; the $C_{1-10}$ alkyl; and the $C_{1-10}$ alkyl moieties of the $C_{1-10}$ alkoxycarbonyl, the $C_{2-11}$ alkanoyl and the $C_{1-10}$ alkylsulfonyl include linear or branched alkyl each having 1 to 10 carbon atoms, and more specifically include methyl, ethyl, propyl, isopropyl, butyl, isobutyl, sec-butyl, tert-butyl, pentyl, isopentyl, neopentyl, hexyl, heptyl, octyl, nonyl, decyl, and the like.

Examples of the aryl include aryl each having 6 to 14 carbon atoms, and more specifically include phenyl, naphthyl, azulenyl, anthryl, and the like.

Examples of the aliphatic heterocyclic group include a 5- or 6-membered monocyclic aliphatic heterocyclic group having at least one atom selected from a nitrogen atom, an oxygen atom and a sulfur atom, a bicyclic or tricyclic fused-ring aliphatic heterocyclic group in which 3- to 8-membered rings are fused and at least one atom selected from a nitrogen atom, an oxygen atom and a sulfur atom is contained, and the like, and more specifically include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzoimidazolidinyl, dihydrobenzoxazolyl, dihydrobenzothioxazolyl, benzodioxolinyl, tetrahydroquinolyl, tetrahydroisoquinolyl, dihydro-2H-chromanyl, dihydro-H-chromanyl, dihydro-2H-thiochromanyl, dihydro-1H-thiochromanyl, tetrahydroquinoxalinyl, tetrahydroquinazolinyl, dihydrobenzodioxanyl, 7,8-dihydro-5H-pyrano[4,3-d]pyrimidinyl, 5,6,7,8-tetrahydropyrido[4,3-d]pyrimidinyl, dioxoloquinazolinyl, 6-oxo-6,7-dihydro-5H-pyrimido[4,5-b][1,4]oxazin-4-yl, and the like.

Examples of the aromatic heterocyclic group include a 5- or 6-membered monocyclic aromatic heterocyclic group having at least one atom selected from a nitrogen atom, an oxygen atom and a sulfur atom, a bicyclic or tricyclic fused-ring aromatic heterocyclic group in which 3- to 8-membered rings are fused and at least one atom selected from a nitrogen atom, an oxygen atom and a sulfur atom is contained, and the like, and more specifically include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridonyl, pyridazinyl, pyrimidinyl, pyrazinyl, triazinyl, benzofuranyl, benzothiophenyl, benzoxazolyl, benzothiazolyl, isoindolyl, indolyl, indazolyl, benzoimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, pyridopyrimidinyl, 7-oxidopyrido[4,3-d]pyrimidinyl, benzo[d][1,2,3]triazinyl, [1,2,4]triazolo[4,3-a]pyridin-3(2H)-onyl, 8-oxo-8,9-dihydro-7H-purin-6-yl, 3-oxo-2,3-dihydro-[1,2,4]triazolo[4,3-a]pyridin-5-yl, 4-oxo-3,4-dihydropyrido[4,3-d]pyrimidin-5-yl, 4-oxo-3,4-dihydropyrido[4,3-d]pyrimidin-7-yl, 4-oxo-3,4-dihydropyrido[3,4-d]pyrimidin-5-yl, 4-oxo-3,4-dihydropyrido[3,4-d]pyrimidin-8-yl, 3-oxo-2,3-dihydro-[1,2,4]triazolo[4,3-a]pyridin-6-yl, 3-oxo-2,3-dihydro-[1,2,4]triazolo[4,3-a]pyrazin-6-yl, 3-oxo-2,3-dihydro-[1,2,4]triazolo[4,3-a]pyrazin-8-yl, imidazo[1,2-a]pyrazinyl, and the like.

Examples of the bicyclic aromatic heterocyclic group include, among the above-mentioned aromatic heterocyclic rings, benzofuranyl, benzothiophenyl, benzoxazolyl, benzothiazolyl, isoindolyl, indolyl, indazolyl, benzoimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, pyridopyrimidinyl, 7-oxidopyrido[4,3-d]pyrimidinyl, benzo[d][1,2,3]triazinyl, [1,2,4]triazolo[4,3-a]pyridin-3(2H)-onyl, 8-oxo-8,9-dihydro-7H-purin-6-yl, 3-oxo-2,3-dihydro-[1,2,4]triazolo[4,3-a]pyridin-5-yl, 4-oxo-3,4-dihydropyrido[4,3-d]pyrimidin-5-yl, 4-oxo-3,4-dihydropyrido[4,3-d]pyrimidin-7-yl, 4-oxo-3,4-dihydropyrido[3,4-d]pyrimidin-5-yl, 4-oxo-3,4-dihydropyrido[3,4-d]pyrimidin-8-yl, 3-oxo-2,3-dihydro-[1,2,4]triazolo[4,3-a]pyridin-6-yl, 3-oxo-2,3-dihydro-[1,2,4]triazolo[4,3-a]pyrazin-6-yl, 3-oxo-2,3-dihydro-[1,2,4]triazolo[4,3-a]pyrazin-8-yl, imidazo[1,2-a]pyrazinyl, and the like.

The halogen means each atom of fluorine, chlorine, bromine or iodine.

Examples of the substituents in the optionally substituted aryl and the optionally substituted aromatic heterocyclic group, which may be the same or different and in number of, for example, 1 to 3, include substituents selected from the group comprising halogen, hydroxy, nitro, cyano, carboxy, sulfamoyl, $C_{1-10}$ alkyl which may be substituted with hydroxy, trifluoromethyl, $C_{3-8}$ cycloalkyl, $C_{6-14}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —NR$^{Xa}$R$^{Ya}$ (wherein R$^{Xa}$ and R$^{Ya}$ may be the same or different, and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$alkoxycarbonyl or $C_{7-16}$ aralkyloxycarbonyl, or R$^{Xa}$ and R$^{Ya}$ are combined together with the adjacent nitrogen atom thereto to form a nitrogen-containing heterocyclic group which may be substituted with $C_{1-10}$ alkyl), $C_{2-11}$ alkanoyl, $C_{7-15}$ aroyl, $C_{1-10}$ alkoxycarbonyl, $C_{6-14}$ aryloxycarbonyl, $C_{1-10}$ alkylsulfonyl, —CONR$^{Xb}$R$^{Yb}$ (wherein R$^{Xb}$ and $R^{Yb}$ may be the same or different, and each represents a hydrogen atom, $C_{1-10}$ alkyl, $C_{3-8}$ cycloalkyl, $C_{6-14}$ aryl, an aromatic heterocyclic group or $C_{7-16}$ aralkyl, or $R^{Xb}$ and $R^{Yb}$ are combined together with the adjacent nitrogen atom thereto to form a nitrogen-containing heterocyclic group which may be substituted with $C_{1-10}$ alkyl), —SO$_2$NR$^{Xc}$R$^{Yc}$ (wherein $R^{Xc}$ and $R^{Yc}$ may be the same or different, and each represents a hydrogen atom or $C_{1-10}$ alkyl, or $R^{Xc}$ and $R^{Yc}$ are combined together with the adjacent nitrogen atom thereto to form a nitrogen-containing heterocyclic group which may be substituted with $C_{1-10}$ alkyl), and the like.

Examples of the substituents of the optionally substituted aliphatic heterocyclic group, which may be the same or different and in number of, for example, 1 to 3, include substituents selected from the group comprising oxo, halogen, hydroxy, nitro, cyano, carboxy, sulfamoyl, $C_{1-10}$ alkyl which may be substituted with hydroxy, trifluoromethyl, $C_{3-8}$ cycloalkyl, $C_{6-14}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —NR$^{Xd}$R$^{Yd}$ (wherein $R^{Xd}$ and $R^{Yd}$ may be the same or different, and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl, or $R^{Xd}$ and $R^{Yd}$ are combined together with the adjacent nitrogen atom thereto to form a nitrogen-containing heterocyclic group which may be substituted with $C_{1-10}$ alkyl), $C_{2-11}$ alkanoyl, $C_{7-15}$ aroyl, $C_{1-10}$ alkoxycarbonyl, $C_{6-14}$ aryloxycarbonyl, —CONR$^{Xe}$R$^{Ye}$ (wherein $R^{Xe}$ and $R^{Ye}$ may be the same or different, and each represents a hydrogen atom, $C_{1-10}$ alkyl, $C_{3-8}$ cycloalkyl, $C_{6-14}$ aryl, an aromatic heterocyclic group or $C_{7-16}$ aralkyl, or $R^{Xe}$ and $R^{Ye}$ are combined together with the adjacent nitrogen atom thereto to form a nitrogen-containing heterocyclic group which may be substituted with $C_{1-10}$ alkyl), $C_{1-10}$ alkylsulfonyl, —SO$_2$NR$^{Xf}$R$^{Yf}$ (wherein $R^{Xf}$ and $R^{Yf}$ may be the same or different, and each represents a hydrogen atom or $C_{1-10}$ alkyl, or $R^{Xf}$ and $R^{Yf}$ are combined together with the adjacent nitrogen atom thereto to form a nitrogen-containing heterocyclic group which may be substituted with $C_{1-10}$ alkyl), and the like.

Examples of the $C_{1-10}$ alkyl and the $C_{1-10}$ alkyl moieties of the $C_{1-10}$ alkoxy, the $C_{2-11}$ alkanoyloxy, the $C_{1-10}$ alkylsulfanyl, the $C_{2-11}$ alkanoyl, the $C_{1-10}$ alkylsulfonyl and the $C_{1-10}$ alkoxycarbonyl shown here include the groups exemplified as the lower alkyl described above.

Examples of the $C_{3-8}$ cycloalkyl and the cycloalkyl moiety of the $C_{3-8}$ cycloalkoxy include cyclopropyl, cyclobutyl, cyclopentyl, cyclohexyl, cycloheptyl, cyclooctyl, and the like.

Examples of the $C_{6-14}$ aryl and the aryl moieties of the $C_{6-14}$ aryloxy, the $C_{7-15}$ aroyl, the $C_{7-15}$ aroyloxy and the $C_{6-14}$ aryloxycarbonyl include the groups exemplified as the aryl described above.

Examples of the aryl moieties of the $C_{7-16}$ aralkyloxy, the $C_{7-16}$ aralkyl and the $C_{7-16}$ aralkyloxycarbonyl include the groups exemplified as the aryl described above, and examples of the alkyl moieties thereof include $C_{1-10}$ alkylene, and more specifically include groups in which one hydrogen atom is removed from the groups exemplified as the lower alkyl described above.

The aliphatic heterocyclic group, the aromatic heterocyclic group and the halogen have the same definitions as described above, respectively.

Examples of the nitrogen-containing heterocyclic group formed together with the adjacent nitrogen atom include a 5- or 6-membered monocyclic heterocyclic group having at least one nitrogen atom (the monocyclic heterocyclic group may contain another nitrogen atom, an oxygen atom or a sulfur atom), a bicyclic or tricyclic fused-ring heterocyclic group in which 3- to 8-membered rings are fused and at least one nitrogen atom is contained (the fused-ring heterocyclic group may contain another nitrogen atom, an oxygen atom or a sulfur atom), and the like, and more specifically include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzoimidazolidinyl, benzoimidazolyl, dihydroindazolyl, indazolyl, benzotriazolyl, pyrrolopyridinyl, pyrrolopyrimidinyl, imidazopyridinyl, purinyl, and the like.

The pharmaceutically acceptable salts of Compounds (IA) and (I) include, for example, pharmaceutically acceptable acid addition salts, metal salts, ammonium salts, organic amine addition salts, amino acid addition salts, and the like. Examples of the pharmaceutically acceptable acid addition salts of Compounds (IA) and (I) include inorganic acid salts such as hydrochlorides, hydrobromides, nitrates, sulfates, phosphates and the like, organic acid salts such as acetates, oxalates, maleates, fumarates, citrates, benzoates, methanesulfonates and the like. Examples of the pharmaceutically acceptable metal salts include alkali metal salts such as sodium salts, potassium salts and the like, alkaline earth metal salts such as magnesium salts, calcium salts, aluminum salts, zinc salts, and the like. Examples of the pharmaceutically acceptable ammonium salts include salts of ammonium, tetramethylammonium, and the like. Examples of the pharmaceutically acceptable organic amine addition salts include addition salts of morpholine, piperidine, and the like. Examples of the pharmaceutically acceptable amino acid addition salts include addition salts of lysine, glycine, phenylalanine, aspartic acid, glutamic acid, and the like.

Next, production processes for Compounds (IA) and (I) will be explained.

Incidentally, in the production processes shown below, when a defined group changes under the conditions of the production processes or is inappropriate for performing the production processes, a target compound can be produced by using the methods for introducing and removing a protective group conventionally used in the organic synthetic chemistry [for example, Protective Groups in Organic Synthesis, third edition, written by T. W. Greene, John Wiley & Sons, Inc. (1999), and the like] and the like. Also, if necessary, it is possible to change the order of the reaction steps of introducing a substituent and the like.

Compounds (IA) and (I) can be produced according to, for example, the following steps.

Production Process 1

Among Compounds (I), Compound (I-a) in which $Y^1$ is $CH_2$, $Y^2$ is N, and L is $CH_2$ can be produced according to, for example, the following steps.

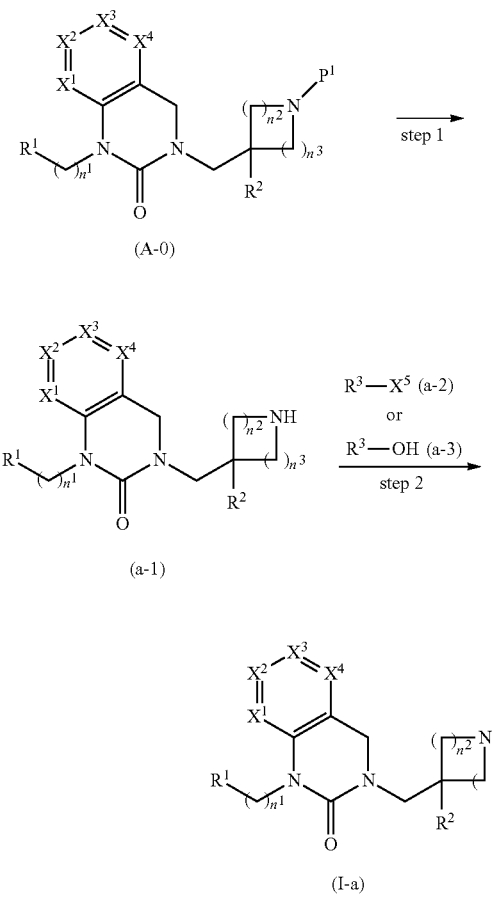

(wherein, $P^1$ represents a protective group for a nitrogen atom conventionally used in the organic synthetic chemistry, for example, methoxycarbonyl, ethoxycarbonyl, tert-butoxycarbonyl, 9-fluorenylmethoxycarbonyl, 2,2,2-trichloroethoxycarbonyl, vinyloxycarbonyl, allyloxycarbonyl, or the like, $X^5$ represents a chlorine atom, a bromine atom, an iodine atom, methanesulfonyloxy, trifluoromethanesulfonyloxy, benzenesulfonyloxy, p-toluenesulfonyloxy, or the like, and $X^1$, $X^2$, $X^3$, $X^4$, $R^1$, $R^2$, $R^3$, $n^1$, $n^2$ and $n^3$ have the same definitions as described above, respectively)

Step 1

Compound (a-1) can be produced by, for example, a modified method of the method for removing a protective group described in Protective Groups in Organic Synthesis, written by T. W. Greene, John Wiley & Sons, Inc. (1981), and the like.

For example, in the case where $P^1$ is tert-butoxycarbonyl, Compound (a-1) can be produced by treating Compound (A-0), for example, without solvent or in a solvent with 1 equivalent to a large excess amount of an acid at a temperature between −30° C. and 100° C. for 5 minutes to 72 hours.

Examples of the acid include hydrochloric acid, sulfuric acid, trifluoroacetic acid, methanesulfonic acid, and the like. Examples of the solvent include methanol, ethanol, 1-propanol, 2-propanol, tetrahydrofuran (THF), 1,4-dioxane, 1,2-dimethoxyethane (DME), toluene, ethyl acetate, dichloromethane, 1,2-dichloroethane, water, and the like, and these are used alone or in admixture.

Compound (A-0) can be produced according to the below-mentioned steps.

Step 2

Compound (I-a) can be produced by reacting Compound (a-1) with preferably 1 to 10 equivalents of Compound (a-2) without solvent or in a solvent, and if necessary, in the presence of preferably 1 to 10 equivalents of a base at a temperature between −20° C. and 150° C. for 5 minutes to 72 hours.

Examples of the base include potassium carbonate, potassium hydroxide, sodium hydroxide, sodium methoxide, sodium hydride, potassium tert-butoxide, triethylamine, diisopropylethylamine, N-methylmorpholine, pyridine, 1,8-diazabicyclo[5.4.0]-7-undecene (DBU), and the like.

Examples of the solvent include methanol, ethanol, 2-propanol, dichloromethane, chloroform, 1,2-dichloroethane, toluene, ethyl acetate, acetonitrile, diethyl ether, THF, DME, 1,4-dioxane, N,N-dimethylformamide (DMF), N,N-dimethylacetamide (DMA), N-methylpyrrolidone (NMP), pyridine, water, and the like, and these are used alone or in admixture.

Compound (a-2) is obtained as a commercially available product or can be obtained by a known method [for example, Jikken Kagaku Koza (Encyclopedia of Experimental Chemistry), 5th Ed., vol. 13, p. 341, Maruzen Co., Ltd. (2003), or the like] or a modified method thereof.

Compound (I-a) can be produced by treating Compound (a-1) with preferably 1 to 10 equivalents of Compound (a-3) in a solvent, in the presence of preferably 1 to 10 equivalents of a condensing agent, and if necessary, in the presence of preferably 1 to 10 equivalents of a base at a temperature between −20° C. and 150° C. for 5 minutes to 72 hours.

Compound (a-3) is obtained as a commercially available product or can be obtained by a known method (for example, Journal of Medicinal Chemistry, 2010, 53, 8089, or the like) or a modified method thereof.

Examples of the condensing agent include benzotriazol-1-yloxytris(dimethylamino)phosphonium hexafluorophosphate (BOP), benzotriazol-1-yloxytris(pyrrolidino)phosphonium hexafluorophosphate (PyBOP), bromotris(pyrrolidino)phosphonium hexafluorophosphate (PyBroP), and the like, and preferably include BOP and the like. Examples of the base include triethylamine, N,N-diisopropylethylamine, DBU, 1,5-diazabicyclo[4.3.0]non-5-ene (DBN), N-methylpiperidine, N-methylphorpholine, and the like, and preferably include DBU and the like. Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, water, and the like, and these are used alone or in admixture.

Compound (A-0) to be used in the above production process 1 can be produced according to the following steps.

Among Compounds (A-0), Compound (A-1), in which $n^1$ is 1, and Compound (A-2), in which $n^1$ is 0 and $R^1$ is optionally substituted aryl or an optionally substituted aromatic heterocyclic group, can be produced according to, for example, the following steps.

[Chem. 13]

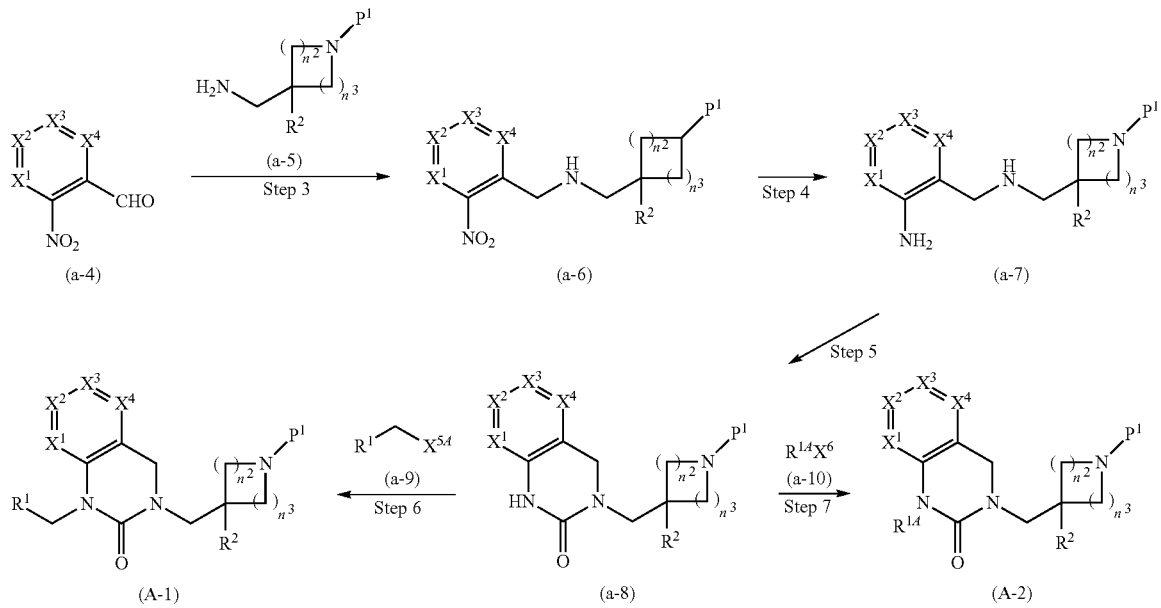

(wherein, $R^{14}$ represents optionally substituted aryl or an optionally substituted aromatic heterocyclic group in the definition of $R^1$, $X^{5A}$ and each represents a chlorine atom, an iodine atom, methanesulfonyloxy, trifluoromethanesulfonyloxy, benzenesulfonyloxy, p-toluenesulfonyloxy, or the like, $X^6$ represents a chlorine atom, a bromine atom, an iodine atom, methanesulfonyloxy, trifluoromethanesulfonyloxy, benzenesulfonyloxy, p-toluenesulfonyloxy, $B(OR^{B1})(OR^{B2})$ (wherein $R^{B1}$ and $R^{B2}$ may be the same or different, and each represents a hydrogen atom, $C_{1-6}$ alkyl, or the like, or $R^{B1}$ and $R^{B2}$ are combined to represent $C_{1-6}$ alkylene or the like), or the like, and $X^1$, $X^2$, $X^3$, $X^4$, $R^2$, $P^1$, $n^2$ and $n^3$ have the same definitions as described above, respectively)

Step 3

Compound (a-6) can be produced by reacting Compound (a-4) with preferably 1 to 10 equivalents of Compound (a-5) in a solvent, in the presence of preferably 1 to 10 equivalents of a reducing agent and preferably 1 to 10 equivalents of an acid at a temperature between −20° C. and 150° C. for 5 minutes to 72 hours.

Examples of the reducing agent include sodium triacetoxyborohydride, sodium cyanoborohydride, and the like.

Examples of the acid include hydrochloric acid, sulfuric acid, formic acid, acetic acid, trifluoroacetic acid, p-toluenesulfonic acid, titanium tetrachloride, and the like.

Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, water, and the like, and these are used alone or in admixture.

Compound (a-5) is obtained as a commercially available product or can be obtained by a known method [for example, Jikken Kagaku Koza, 5th Ed., vol. 14, p. 351, Maruzen Co., Ltd. (2003), or the like] or a modified method thereof.

Compound (a-4) can be obtained as a commercially available product.

Step 4

Compound (a-7) can be produced by treating Compound (a-6) in a solvent in the presence of 1 to 30 equivalents of an additive at a temperature between −20° C. and the boiling point of the solvent to be used for 5 minutes to 72 hours, or by treating Compound (a-6) under a hydrogen atmosphere or in the presence of a hydrogen source in the presence of a catalyst at a temperature between −20° C. and the boiling point of the solvent to be used at normal pressure or under increased pressure for 5 minutes to 72 hours.

Examples of the additive include reduced iron, tin(II) chloride, and the like.

Examples of the catalyst include palladium on carbon, palladium, palladium hydroxide, palladium acetate, palladium black, and the like, and these are used in an amount of preferably 0.01 to 50 weight % with respect to Compound (a-6).

Examples of the hydrogen source include formic acid, ammonium formate, sodium formate, cyclohexadiene, hydrazine, and the like, and these are used in an amount of preferably 2 equivalents to a large excess amount with respect to Compound (a-6).

Examples of the solvent include methanol, ethanol, toluene, ethyl acetate, acetonitrile, diethyl ether, THF, DME, 1,4-dioxane, DMF, DMA, NMP, acetic acid, water, and the like, and these are used alone or in admixture.

Step 5

Compound (a-8) can be produced by reacting Compound (a-7) in a solvent in the presence of preferably 1 to 10 equivalents of phosgene or 1,1-carbonyldiimidazole, and if necessary, in the presence of preferably 1 to 10 equivalents of a base at a temperature between −20° C. and the boiling point of the solvent to be used for 5 minutes to 72 hours.

Examples of the base include potassium carbonate, potassium hydroxide, sodium hydroxide, sodium methoxide, sodium hydride, potassium tert-butoxide, triethylamine, diisopropylethylamine, DBU, and the like.

Examples of the solvent include dichloromethane, chloroform, 1,2-dichloroethane, toluene, ethyl acetate, acetonitrile, diethyl ether, THF, DMF, NMP, pyridine, and the like, and these are used alone or in admixture.

Step 6

Compound (A-1) can be obtained in the same manner as in the above-mentioned Step 2 using Compound (a-8) and preferably 1 to 10 equivalents of Compound (a-9).

Compound (a-9) can be obtained as a commercially available product.

Step 7

Compound (A-2) can be produced by reacting Compound (a-8) with 1 to 10 equivalents of Compound (a-10) in a solvent in the presence of a catalytic amount to 10 equivalents of a copper catalyst or a palladium catalyst at a temperature between room temperature and 140° C. for 5 minutes to 72 hours. The reaction can also be performed in the presence of a catalytic amount to 10 equivalents of a base, and can also be performed in the presence of a catalytic amount to 10 equivalents of an organophosphorus compound.

Examples of the copper catalyst include copper(0), copper (I) iodide, copper(II) iodide, copper(II) acetate, copper(II) oxide, copper(I) chloride, di-μ-hydroxo-bis[(N,N,N',N'-tetramethylethylenediamine)copper(II)] chloride, and the like, and preferably include copper(I) iodide, copper(II) acetate, and the like.

Examples of the palladium catalyst include palladium(II) acetate, bis(triphenylphosphine)palladium(II) chloride, tetrakis(triphenylphosphine)palladium(0), [1,2-bis(diphenylphosphino)ethane]palladium(II) chloride, [1,1'-bis(diphenylphosphino)ferrocene]palladium(II) chloride, Tris (dibenzylideneacetone)dipalladium(0), and the like, and preferably include palladium(II) acetate, bis(triphenylphosphine)palladium(II) chloride, tetrakis(triphenylphosphine) palladium(0), Tris(dibenzylideneacetone)dipalladium(0), and the like.

Examples of the base include potassium carbonate, cesium carbonate, lithium chloride, potassium chloride, potassium tert-butoxide, sodium tert-butoxide, triethylamine, potassium acetate, sodium ethoxide, sodium carbonate, sodium hydroxide, potassium phosphate, ethylenediamine, glycine, N-methylpyrrolidine, pyridine, 1,2-diaminocyclohexane, and the like, and preferably include potassium carbonate, cesium carbonate, potassium tert-butoxide, potassium phosphate, ethylenediamine, 1,2-diaminocyclohexane, triethylamine, and the like.

Examples of the organophosphorus compound include triphenylphosphine, tri(2-furyl)phosphine, 2-dicyclohexylphosphino-2'-(N,N-dimethylamino)biphenyl, diphenylphosphinoferrocene, 2-dicyclohexylphosphino-2'4'6'-triisopropylbiphenyl (XPhos), and the like, and preferably include 2-dicyclohexylphosphino-2'-(N,N-dimethylamino)biphenyl, XPhos, and the like.

Examples of the solvent include diethyl ether, THF, 1,4-dioxane, DMF, DMA, dimethyl sulfoxide (DMSO), benzene, toluene, xylene, dichloromethane, chloroform, carbon tetrachloride, 1,2-dichloroethane, acetonitrile, ethyl acetate, methyl acetate, methyl ethyl ketone, methanol, ethanol, propanol, 2-propanol, butanol, hexane, and the like, and preferably include THF, 1,4-dioxane, DMF, and the like.

Compound (a-10) is obtained as a commercially available product or can be obtained by a known method [for example, Jikken Kagaku Koza, 5th Ed., vol. 13, p. 341, Maruzen Co., Ltd. (2003), or the like] or a modified method thereof.

Among Compounds (A-0), Compound (A-3) in which $n^1$ is 0 and $R^1$ is an optionally substituted aliphatic heterocyclic group can be produced according to, for example, the following steps.

[Chem. 14]

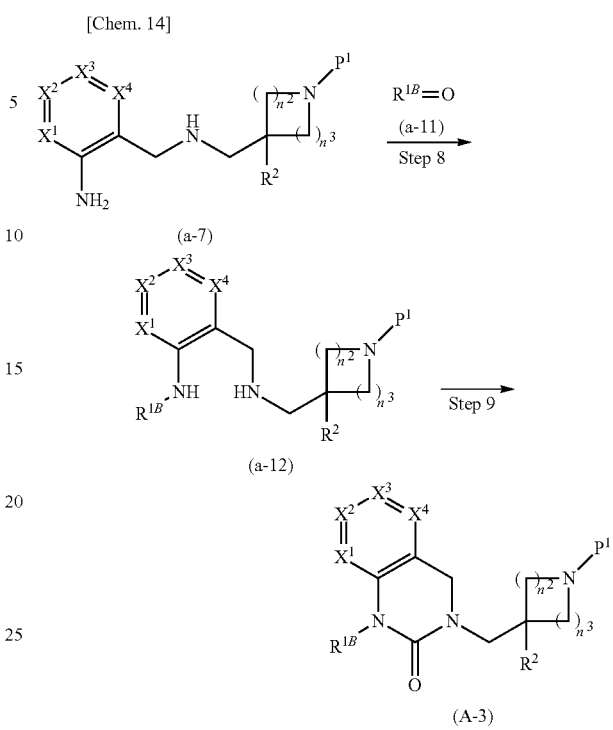

(wherein, $R^{1B}$ represents an optionally substituted aliphatic heterocyclic group in the definition of $R^1$, and $X^1$, $X^2$, $X^3$, $X^4$, $R^2$, $P^1$, $n^2$ and $n^3$ have the same definitions as described above, respectively)

Step 8

Compound (a-12) can be produced in the same manner as in the above-mentioned Step 3 using Compound (a-7) obtained in Step 4 and Compound (a-11).

Compound (a-11) is obtained as a commercially available product or can be obtained by a known method [for example, Jikken Kagaku Koza, 5th Ed., vol. 15, p. 154, Maruzen Co., Ltd. (2003), or the like] or a modified method thereof.

Step 9

Compound (A-3) can be produced in the same manner as in the above-mentioned Step 5 using Compound (a-12).

Production Process 2

Among Compounds (I), Compound (I-b) and Compound (I-c), in which $R^2$ is a hydrogen atom, $Y^1$ is $CH_2$, $Y^2$ is CH, and L is NH, and (i) $n^1$ is 1 (Compound (I-b)) or (ii) $n^1$ is 0 and $R^1$ is optionally substituted aryl or an optionally substituted aromatic heterocyclic group (Compound (I-c)), can be produced according to, for example, the following steps.

[Chem. 15]

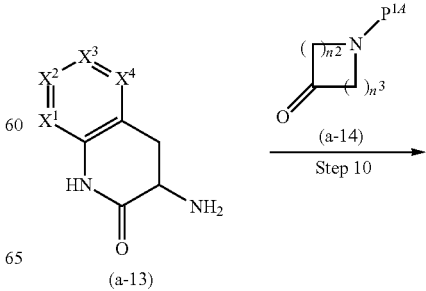

-continued

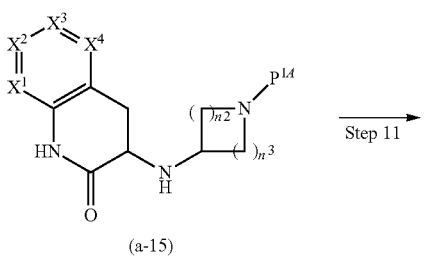

(a-15)

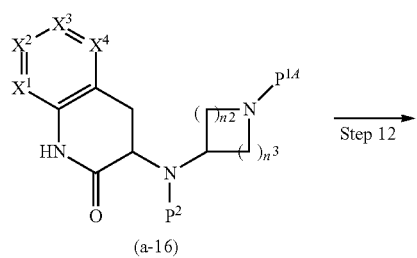

(a-16)

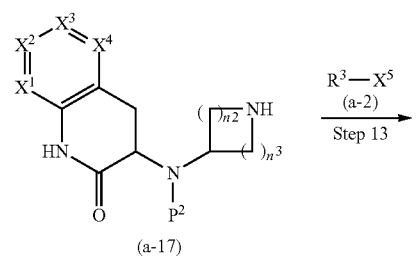

(a-17)

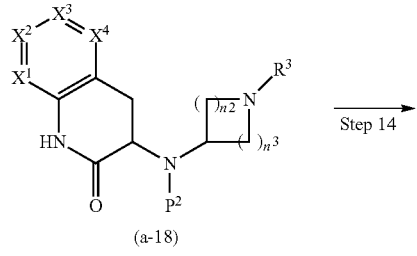

(a-18)

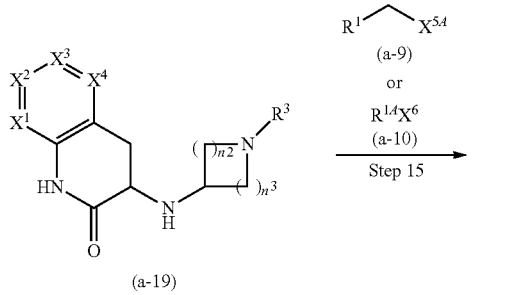

(a-19)

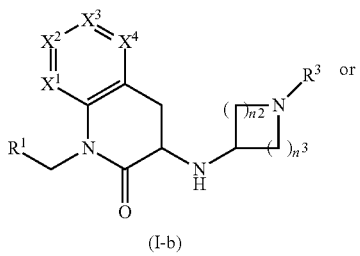

(I-b)

-continued

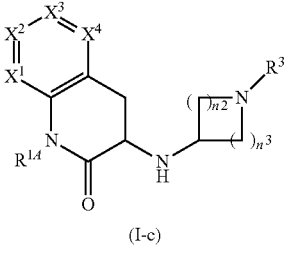

(I-c)

(wherein, $P^{1A}$ represents a protective group which can be removed with an acid among the groups represented by $P^1$, for example, tert-butoxycarbonyl or the like, $P^2$ represents a protective group for a nitrogen atom conventionally used in the organic synthetic chemistry, for example, acyl such as formyl, acetyl, monochloroacetyl, trifluoroacetyl, trichloroacetyl, benzoyl, or the like, and $X^1$, $X^2$, $X^3$, $X^4$, $X^5$, $X^{5A}$, $X^6$, $R^1$, $R^{1A}$, $R^3$, $n^2$ and $n^3$ have the same definitions as described above, respectively)

Step 10

Compound (a-15) can be produced in the same manner as in the above-mentioned Step 3 using Compound (a-13) and Compound (a-14).

Compound (a-13) is obtained as a commercially available product or can be obtained by a known method (for example, WO2004/98589 or the like) or a modified method thereof.

Compound (a-14) is obtained as a commercially available product or can be obtained by a known method [for example, Jikken Kagaku Koza, 5th Ed., vol. 15, p. 153, Maruzen Co., Ltd. (2003), or the like] or a modified method thereof.

Step 11

Compound (a-16) can be produced by, for example, a modified method of the method for introducing a protective group described in Protective Groups in Organic Synthesis, written by T. W. Greene, John Wiley & Sons, Inc. (1981), or the like using Compound (a-15).

For example, in the case where $P^2$ is trifluoroacetyl, Compound (a-16) can be produced by reacting Compound (a-15) with preferably 1 to 10 equivalents of trifluoroacetic anhydride without solvent or in a solvent in the presence of preferably 1 to 10 equivalents of a base at a temperature between −78° C. and 150° C. for 5 minutes to 72 hours.

Examples of the base include triethylamine, N,N-diisopropylethylamine, pyridine, N-methylpiperidine, N-methylmorpholine, and the like.

Examples of the solvent include methanol, ethanol, dichloromethane, chloroform, 1,2-dichloroethane, toluene, ethyl acetate, acetonitrile, diethyl ether, THF, DME, 1,4-dioxane, DMF, DMA, NMP, water, and the like, and these are used alone or in admixture.

Step 12

Compound (a-17) can be obtained in the same manner as in the above-mentioned Step 1 using Compound (a-16).

Step 13

Compound (a-18) can be produced in the same manner as in the above-mentioned Step 2 using Compound (a-17) and Compound (a-2).

Step 14

Compound (a-19) can be produced by, for example, a modified method of the method for removing a protective group described in Protective Groups in Organic Synthesis, written by T. W. Greene, John Wiley & Sons, Inc. (1981), or the like.

For example, in the case where $P^2$ is trifluoroacetyl, Compound (a-19) can be produced by treating Compound (a-18) in a solvent containing water with preferably 1 equivalent to a large excess amount of a base at a temperature between −30° C. and the boiling point of the solvent to be used for 5 minutes to 72 hours.

Examples of the base include sodium hydroxide, potassium hydroxide, lithium hydroxide, barium hydroxide, sodium carbonate, potassium carbonate, and the like. Examples of the solvent include methanol, ethanol, propanol, THF, 1,4-dioxane, DME, toluene, dichloromethane, DMF, water, and the like, and these are used alone or in admixture.

Step 15

Compounds (I-b) and (I-c) can be obtained in the same manner as in Step 6 or Step 7 using Compound (a-19), and Compound (a-9) or Compound (a-10).

Production Process 3

Among Compounds (I), Compound (I-d) and Compound (I-e), in which $Y^1$ is C(=O), $Y^2$ is N, and L is CH$_2$, and (i) $n^1$ is 1 (Compound (I-d)) or (ii) $n^1$ is 0 and $R^1$ is optionally substituted aryl or an optionally substituted aromatic heterocyclic group (Compound (I-e)), can be produced according to, for example, the following steps.

[Chem. 16]

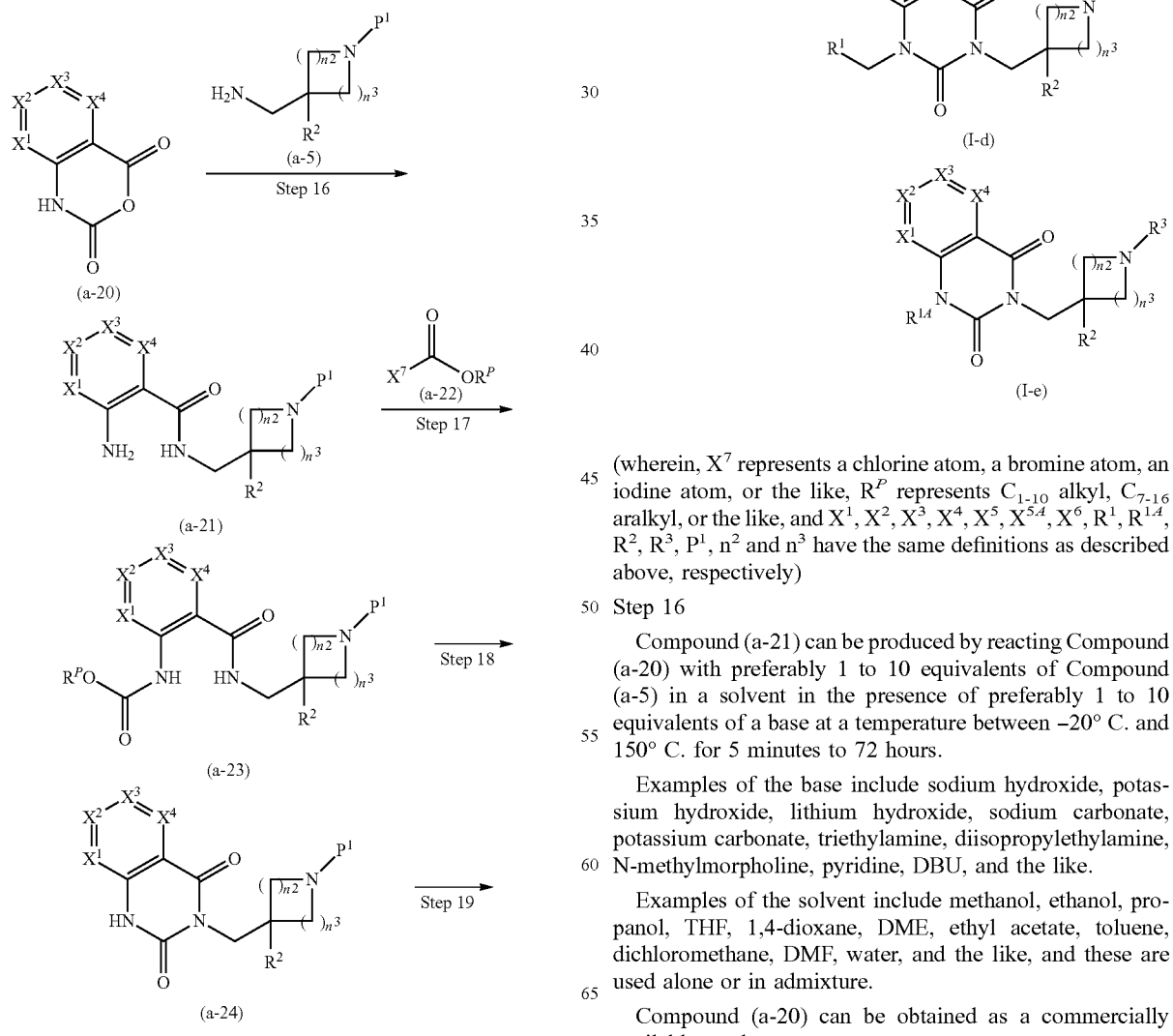

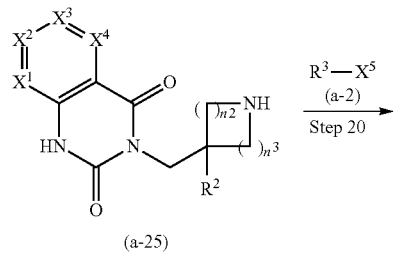

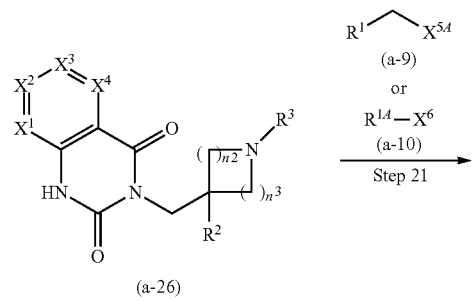

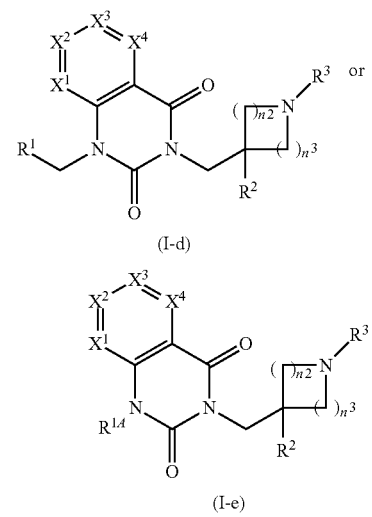

(wherein, $X^7$ represents a chlorine atom, a bromine atom, an iodine atom, or the like, $R^P$ represents $C_{1-10}$ alkyl, $C_{7-16}$ aralkyl, or the like, and $X^1$, $X^2$, $X^3$, $X^4$, $X^5$, $X^{5A}$, $X^6$, $R^1$, $R^{1A}$, $R^2$, $R^3$, $P^1$, $n^2$ and $n^3$ have the same definitions as described above, respectively)

Step 16

Compound (a-21) can be produced by reacting Compound (a-20) with preferably 1 to 10 equivalents of Compound (a-5) in a solvent in the presence of preferably 1 to 10 equivalents of a base at a temperature between −20° C. and 150° C. for 5 minutes to 72 hours.

Examples of the base include sodium hydroxide, potassium hydroxide, lithium hydroxide, sodium carbonate, potassium carbonate, triethylamine, diisopropylethylamine, N-methylmorpholine, pyridine, DBU, and the like.

Examples of the solvent include methanol, ethanol, propanol, THF, 1,4-dioxane, DME, ethyl acetate, toluene, dichloromethane, DMF, water, and the like, and these are used alone or in admixture.

Compound (a-20) can be obtained as a commercially available product.

Step 17

Compound (a-23) can be produced by reacting Compound (a-21) with preferably 1 to 10 equivalents of Compound (a-22) in a solvent in the presence of preferably 1 to 10 equivalents of a base at a temperature between −20° C. and 150° C. for 5 minutes to 72 hours.

Examples of the base include sodium hydroxide, potassium hydroxide, lithium hydroxide, sodium carbonate, potassium carbonate, triethylamine, diisopropylethylamine, N-methylmorpholine, pyridine, 4-dimethylaminopyridine, DBU, and the like.

Examples of the solvent include methanol, ethanol, propanol, THF, 1,4-dioxane, DME, ethyl acetate, toluene, dichloromethane, 1,2-dichloroethane, DMF, water, and the like, and these are used alone or in admixture.

Compound (a-22) can be obtained as a commercially available product.

Step 18

Compound (a-24) can be produced by treating Compound (a-23) in a solvent in the presence of preferably 1 to 10 equivalents of a base at a temperature between −20° C. and the boiling point of the solvent to be used for 5 minutes to 72 hours.

Examples of the base include sodium hydroxide, potassium hydroxide, lithium hydroxide, sodium carbonate, potassium carbonate, triethylamine, diisopropylethylamine, N-methylmorpholine, pyridine, 4-dimethylaminopyridine, DBU, and the like.

Examples of the solvent include methanol, ethanol, propanol, THF, 1,4-dioxane, DME, ethyl acetate, toluene, dichloromethane, 1,2-dichloroethane, DMF, water, and the like, and these are used alone or in admixture.

Step 19

Compound (a-25) can be produced in the same manner as in the above-mentioned Step 1 using Compound (a-24).

Step 20

Compound (a-26) can be produced in the same manner as in the above-mentioned Step 2 using Compound (a-25) and Compound (a-2).

Step 21

Compound (I-d) and Compound (I-e) can be produced in the same manner as in the above-mentioned Step 6 or Step 7 using Compound (a-26), and Compound (a-9) or Compound (a-10).

Production Process 4

Among Compounds (I), Compound (I-f), in which $R^3$ is an optionally substituted aromatic heterocyclic group or an optionally substituted aliphatic heterocyclic group, and the group is an aromatic heterocyclic group substituted with —$NR^8R^9$ (wherein $R^8$ and $R^9$ may be the same or different, and each represents a hydrogen atom, $C_{1-10}$ alkyl, $C_{3-8}$ cycloalkyl, $C_{6-14}$ aryl, an aromatic heterocyclic group or $C_{7-16}$ aralkyl, or $R^8$ and $R^9$ are combined together with the adjacent nitrogen atom thereto to form a nitrogen-containing heterocyclic group which may be substituted with $C_{1-10}$ alkyl) (the aromatic heterocyclic group may further has another substituent) or an aliphatic heterocyclic group substituted with —$NR^8R^9$ (wherein $R^8$ and $R^9$ have the same definitions as described above, respectively) (the aliphatic heterocyclic group may further has another substituent), can also be produced according to, for example, the following method.

[Chem. 17]

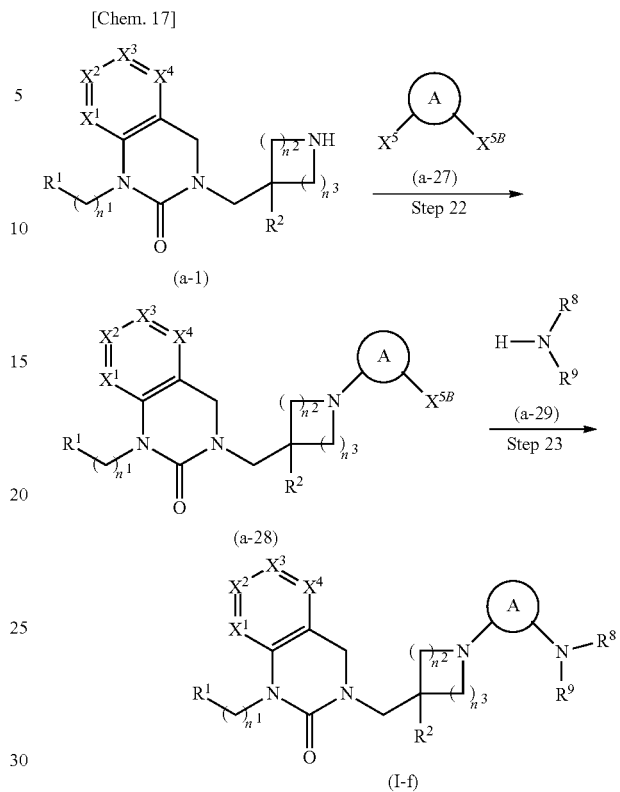

(wherein, $X^{5B}$ represents a chlorine atom, a bromine atom, an iodine atom, methanesulfonyloxy, trifluoromethanesulfonyloxy, benzenesulfonyloxy, p-toluenesulfonyloxy, or the like, the ring A represents an aromatic heterocyclic group moiety of an optionally substituted aromatic heterocyclic group (the aromatic heterocyclic group moiety may further has a substituent) or an aliphatic heterocyclic group moiety of an optionally substituted aliphatic heterocyclic group (the aliphatic heterocyclic group moiety may further has a substituent) in the definition of $R^3$, and $X^1$, $X^2$, $X^3$, $X^4$, $X^5$, $R^1$, $R^2$, $R^8$, $R^9$, $n^1$, $n^2$ and $n^3$ have the same definitions as described above, respectively)

Step 22

Compound (a-28) can be produced in the same manner as in the above-mentioned Step 2 using Compound (a-1) and Compound (a-27).

Compound (a-27) is obtained as a commercially available product or can be obtained by a known method [for example, Jikken Kagaku Koza, 5th Ed., vol. 13, p. 341, Maruzen Co., Ltd. (2003), or the like] or a modified method thereof.

Step 23

Compound (I-f) can be produced by reacting Compound (a-28) with 1 to 10 equivalents of Compound (a-29) in a solvent in the presence of a catalytic amount to 10 equivalents of a palladium catalyst at a temperature between room temperature and 140° C. for 5 minutes to 72 hours. The reaction can also be performed in the presence of a catalytic amount to 10 equivalents of a base, and can also be performed in the presence of a catalytic amount to 10 equivalents of an organophosphorus compound.

Examples of the palladium catalyst include palladium(II) acetate, bis(triphenylphosphine)palladium(II) chloride, tetrakis(triphenylphosphine)palladium(0), [1,2-bis(diphenylphosphino)ethane]palladium(II) chloride, [1,1'-bis(diphenylphosphino)ferrocene]palladium(II) chloride, Tris (dibenzylideneacetone)dipalladium(0), and the like, and preferably include palladium(II) acetate, bis(triphenylphosphine)palladium(II) chloride, tetrakis(triphenylphosphine)palladium(0), Tris(dibenzylideneacetone)dipalladium(0), and the like.

Examples of the base include potassium carbonate, cesium carbonate, lithium chloride, potassium chloride, potassium tert-butoxide, sodium tert-butoxide, triethylamine, potassium acetate, sodium ethoxide, sodium carbonate, sodium hydroxide, potassium phosphate, ethylenediamine, glycine, N-methylpyrrolidine, pyridine, 1,2-diaminocyclohexane, and the like, and preferably include potassium carbonate, cesium carbonate, potassium tert-butoxide, potassium phosphate, triethylamine, and the like.

Examples of the organophosphorus compound include triphenylphosphine, tri(2-furyl)phosphine, 2-dicyclohexylphosphino-2'-(N,N-dimethylamino)biphenyl, diphenylphosphinoferrocene, XPhos, and the like, and preferably include 2-dicyclohexylphosphino-2'-(N,N-dimethylamino)biphenyl, XPhos, and the like.

Examples of the solvent include diethyl ether, THF, 1,4-dioxane, DMF, DMA, DMSO, benzene, toluene, xylene, dichloromethane, chloroform, carbon tetrachloride, 1,2-dichloroethane, acetonitrile, ethyl acetate, methyl acetate, methyl ethyl ketone, methanol, ethanol, propanol, 2-propanol, butanol, hexane, and the like, and preferably include THF, 1,4-dioxane, DMF, and the like.

Compound (a-29) is obtained as a commercially available product or can be obtained by a known method [for example, Jikken Kagaku Koza, 5th Ed., vol. 14, p. 351, Maruzen Co., Ltd. (2003), or the like] or a modified method thereof.

Production Process 5

Among Compounds (I), Compound (I-g) and Compound (I-h), in which $R^3$ is an optionally substituted aromatic heterocyclic group or an optionally substituted aliphatic heterocyclic group, and the group is an aromatic heterocyclic group substituted with carboxy or —$CONR^{8'}R^{9'}$ (wherein $R^{8'}$ and $R^{9'}$ may be the same or different, and each represents a hydrogen atom, $C_{1-10}$ alkyl, $C_{3-8}$ cycloalkyl, $C_{6-14}$ aryl, an aromatic heterocyclic group or $C_{7-16}$ aralkyl, or $R^{8'}$ and $R^{9'}$ are combined together with the adjacent nitrogen atom thereto to form a nitrogen-containing heterocyclic group which may be substituted with $C_{1-10}$ alkyl) (the aromatic heterocyclic group may further has another substituent) or an aliphatic heterocyclic group substituted with carboxy or —$CONR^{8'}R^{9'}$ (wherein $R^{8'}$ and $R^{9'}$ have the same definitions as described above, respectively) (the aliphatic heterocyclic group may further has another substituent), can also be produced according to, for example, the following method.

[Chem. 18]

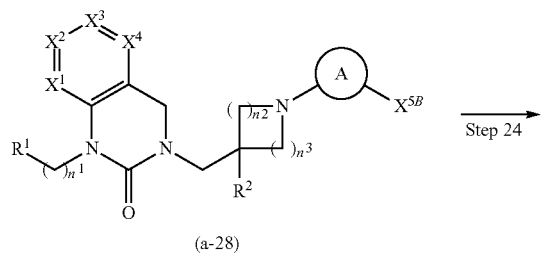

(a-28)

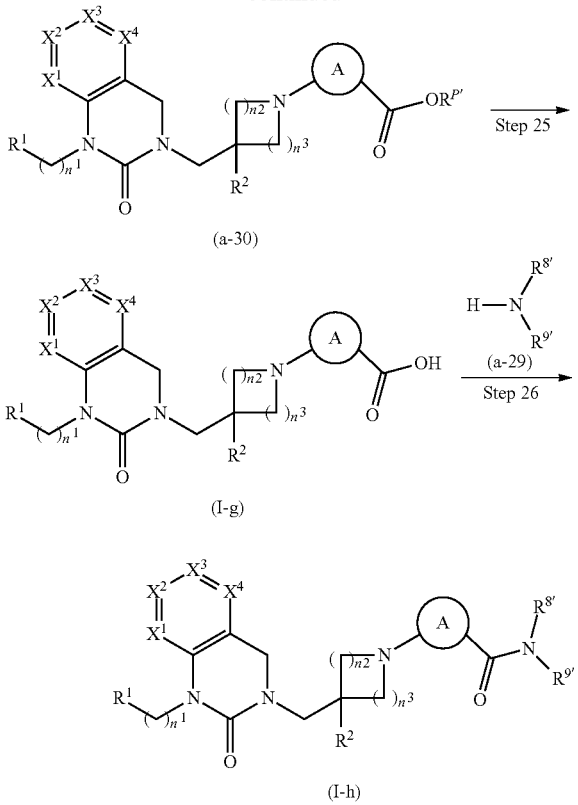

(wherein, $R^{P'}$ represents $C_{1-10}$ alkyl, $C_{7-16}$ aralkyl, or the like, and the ring A, $X^1$, $X^2$, $X^3$, $X^4$, $R^1$, $R^2$, $R^{8'}$, $R^{9'}$, $n^1$, $n^2$ and $n^3$ have the same definitions as described above, respectively)

Step 24

Compound (a-30) can be produced by reacting Compound (a-28) in a solvent under a carbon monoxide atmosphere in the presence of preferably 1 equivalent to a large excess amount of $R^{P'}OH$ (wherein $R^{P'}$ has the same definition as described above) and preferably 1 to 100 mol % of a palladium catalyst, and if necessary, in the presence of preferably 1 to 100 mol % of an organophosphorus compound and/or preferably 1 to 10 equivalents of a base at a temperature between −20° C. and the boiling point of the solvent to be used at normal pressure or under increased pressure for 5 minutes to 72 hours.

Examples of the base include potassium carbonate, potassium phosphate, potassium hydroxide, triethylamine, diisopropylethylamine, N-methylmorpholine, pyridine, DBU, potassium acetate, sodium acetate, and the like. Examples of the palladium catalyst include palladium acetate, tetrakis(triphenylphosphine)palladium, and the like.

Examples of the organophosphorus compound include triphenylphosphine, 1,1'-bis(diphenylphosphino)ferrocene, 1,3-bis(diphenylphosphino)propane, and the like.

Examples of the solvent include dichloromethane, chloroform, 1,2-dichloroethane, toluene, ethyl acetate, acetonitrile, diethyl ether, THF, DME, 1,4-dioxane, DMF, DMA, NMP, water, and the like, and these are used alone or in admixture.

Step 25

Compound (I-g) can be produced by, for example, a modified method of the method for removing a protective group described in Protective Groups in Organic Synthesis, third edition, written by T. W. Greene, John Wiley & Sons, Inc. (1999), or the like using Compound (a-30).

For example, in the case where $R^{P'}$ is methyl, ethyl or n-propyl, Compound (I-g) can be produced by treating Compound (a-30) in a solvent containing water with preferably 1 equivalent to a large excess amount of a base at a temperature between 0° C. and the boiling point of the solvent to be used for 5 minutes to 72 hours.

Examples of the base include sodium hydroxide, potassium hydroxide, lithium hydroxide, and the like.

Examples of the solvent include methanol, ethanol, propanol, THF, 1,4-dioxane, DME, toluene, dichloromethane, DMF, water, and the like, and these are used alone or in admixture.

Further, for example, in the case where $R^{P'}$ is tert-butyl, Compound (I-g) can be produced by treating Compound (a-30) without solvent or in a solvent with 1 equivalent to a large excess amount of an acid at a temperature between −30° C. and 100° C. for 5 minutes to 72 hours.

Examples of the acid include hydrochloric acid, sulfuric acid, trifluoroacetic acid, methanesulfonic acid, and the like.

Examples of the solvent include methanol, ethanol, propanol, THF, 1,4-dioxane, DME, toluene, ethyl acetate, dichloromethane, DMF, water, and the like, and these are used alone or in admixture.

Step 26

Compound (I-h) can be produced by reacting Compound (I-g) with preferably 1 to 30 equivalents of Compound (a-29) without solvent or in a solvent, in the presence of preferably 1 to 30 equivalents of a condensing agent, and if necessary, in the presence of preferably 1 to 30 equivalents of an additive at a temperature between −30° C. and 150° C. for 5 minutes to 72 hours.

Examples of the condensing agent include dicyclohexylcarbodiimide (DCC), diisopropylcarbodiimide, N-(3-dimethylaminopropyl)-N'-ethylcarbodiimide (EDC), EDC hydrochloride, O-(7-aza-1H-benzotriazol-1-yl)-N,N,N',N'-tetramethyluronium hexafluorophosphate (HATU), and the like.

Examples of the additive include 1-hydroxybenzotriazole monohydrate (HOBt.H$_2$O), triethylamine, diisopropylethylamine, 4-dimethylaminopyridine (DMAP), and the like, and these are used alone or in admixture.

Examples of the solvent include acetonitrile, dichloromethane, 1,2-dichloroethane, chloroform, DME, DMF, DMA, 1,4-dioxane, THF, diethyl ether, diisopropyl ether, benzene, toluene, xylene, pyridine, NMP, water, and the like, and these are used alone or in admixture.

Production Process 6

Among Compounds (I), Compound (I-i) and Compound (I-j), in which $R^3$ is an optionally substituted aromatic heterocyclic group, and the aromatic heterocyclic group is an aromatic heterocyclic group containing a nitrogen atom, and is a group in which oxo is attached to the nitrogen of the aromatic heterocyclic group (the group may further has another substituent), and (i) $n^1$ is 1 (Compound (I-i)) or (ii) $n^1$ is 0 and $R^1$ is optionally substituted aryl or an optionally substituted aromatic heterocyclic group (Compound (I-j)), can also be produced according to, for example, the following method.

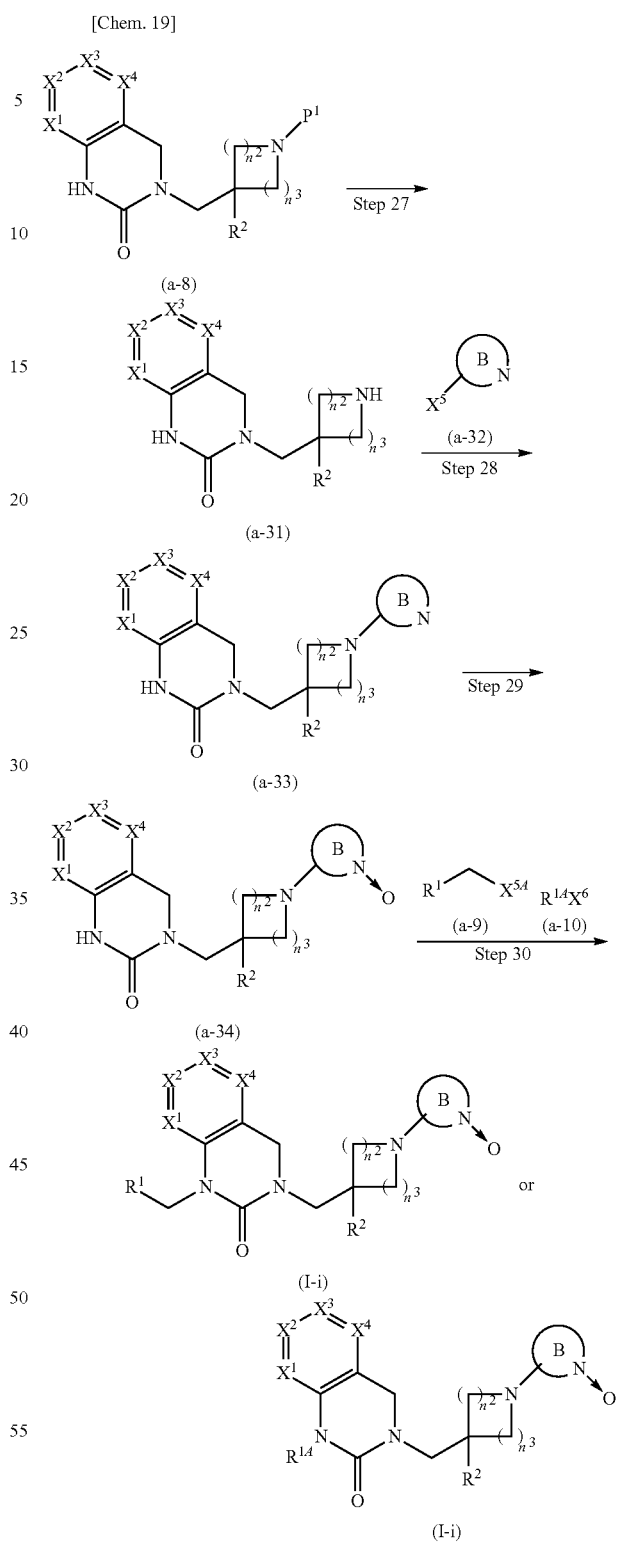

[Chem. 19]

(wherein, the ring B represents an optionally substituted aromatic heterocyclic group, and the aromatic heterocyclic group is an aromatic heterocyclic group containing a nitrogen atom (the aromatic heterocyclic group moiety may further has a substituent) in the definition of $R^3$, and $X^1$, $X^2$, $X^3$, $X^4$, $X^5$, $X^{5A}$, $X^6$, $P^1$, $R^1$, $R^{1A}$, $R^2$, $n^2$ and $n^3$ have the same definitions as described above, respectively)

Step 27

Compound (a-31) can be produced in the same manner as in the above-mentioned Step 1 using Compound (a-8).

Step 28

Compound (a-33) can be produced in the same manner as in the above-mentioned Step 2 using Compound (a-31) and Compound (a-32).

Compound (a-32) is obtained as a commercially available product or can be obtained by a known method [for example, Jikken Kagaku Koza, 5th Ed., vol. 13, p. 341, Maruzen Co., Ltd. (2003), or the like] or a modified method thereof.

Step 29

Compound (a-34) can be produced by treating Compound (a-33) in a solvent with 1 equivalent to a large excess amount, preferably, 1 to 10 equivalents of an oxidizing agent at a temperature between 0° C. and the boiling point of the solvent to be used for 5 minutes to 72 hours.

Examples of the solvent include dichloromethane, chloroform, 1,2-dichloroethane, THF, 1,4-dioxane, dimethoxyethane, diethyl ether, diisopropyl ether, methanol, ethanol, isopropyl alcohol, benzene, toluene, xylene, acetonitrile, ethyl acetate, water, and the like, and these are used alone or in admixture.

Examples of the oxidizing agent include meta-chloroperoxybenzoic acid, benzoyl peroxide, peracetic acid, hydrogen peroxide, sodium periodate, oxone, and the like.

Step 30

Compound (I-i) and Compound (I-j) can be produced in the same manner as in the above-mentioned Step 6 or Step 7 using Compound (a-34), and Compound (a-9) or Compound (a-10).

Production Process 7

Among Compounds (I), Compound (I-k) in which $R^3$ is represented by the following formula:

[Chem. 20]

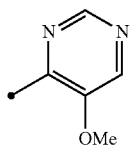

can also be produced according to, for example, the following method.

[Chem. 21]

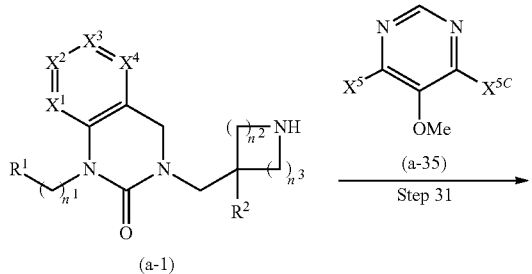

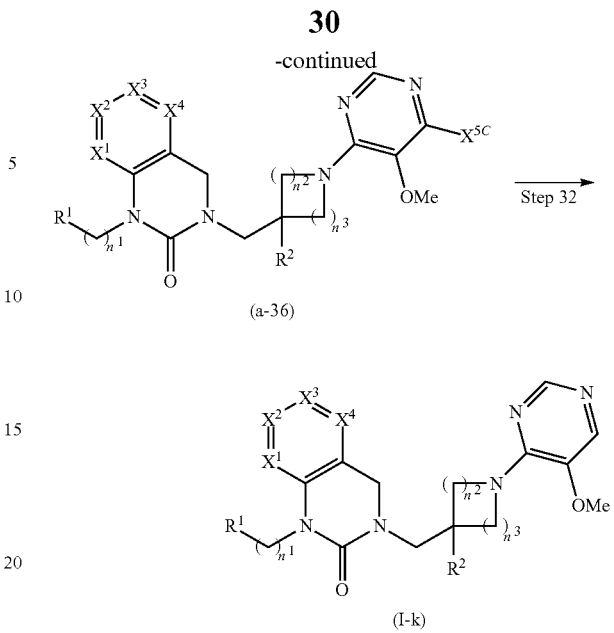

(wherein, $X^{5C}$ represents a chlorine atom, a bromine atom, an iodine atom, methanesulfonyloxy, trifluoromethanesulfonyloxy, benzenesulfonyloxy, p-toluenesulfonyloxy, or the like, and $X^1$, $X^2$, $X^3$, $X^4$, $X^5$, $R^1$, $R^2$, $n^1$, $n^2$ and $n^3$ have the same definitions as described above, respectively)

Step 31

Compound (a-36) can be produced in the same manner as in the above-mentioned Step 2 using Compound (a-1) and Compound (a-35).

Compound (a-35) is obtained as a commercially available product or can be obtained by a known method [for example, Patent Literature (US2009/286816) or the like] or a modified method thereof.

Step 32

Compound (I-k) can be produced by treating Compound (a-36) in a solvent under a hydrogen atmosphere or in the presence of a hydrogen source in the presence of a catalyst and a base at a temperature between −20° C. and the boiling point of the solvent to be used at normal pressure or under increased pressure for 5 minutes to 72 hours.

Examples of the catalyst include palladium on carbon, palladium, palladium hydroxide, palladium acetate, palladium black, and the like, and these are used in an amount of preferably 0.01 to 50% by weight with respect to Compound (a-36).

Examples of the hydrogen source include formic acid, ammonium formate, sodium formate, cyclohexadiene, hydrazine, and the like, and these are used in an amount of preferably 2 equivalents to a large excess amount with respect to Compound (a-36).

Examples of the base include triethylamine, diisopropylethylamine, pyridine, N-methylphorpholine, and the like, and these are used in an amount of preferably 1 to 30 equivalents with respect to Compound (a-36).

Examples of the solvent include methanol, ethanol, toluene, ethyl acetate, acetonitrile, diethyl ether, THF, DME, 1,4-dioxane, DMF, DMA, NMP, acetic acid, water, and the like, and these are used alone or in admixture.

Production Process 8

Among Compounds (I), Compound (I-1) and Compound (I-m), in which $n^1$ is 0 and $R^1$ is optionally substituted aryl or an optionally substituted aromatic heterocyclic group, and the group is aryl substituted with carboxy or —CONR$^{8''}$R$^{9''}$ (wherein R$^{8''}$ and R$^{9''}$ may be the same or different, and each represents a hydrogen atom, C$_{1-10}$ alkyl, C$_{3-8}$ cycloalkyl, C$_{6-14}$ aryl, an aromatic heterocyclic group or C$_{7-16}$ aralkyl, or R$^{8''}$ and R$^{9''}$ are combined together with the adjacent nitrogen atom thereto to form a nitrogen-containing heterocyclic group) (the aryl may further has another substituent) or an aromatic heterocyclic group substituted with carboxy or —CONR$^{8''}$R$^{9''}$ (wherein R$^{8''}$ and R$^{9''}$ have the same definitions as described above, respectively) (the aromatic heterocyclic group may further has another substituent), can also be produced according to, for example, the following method.

[Chem. 22]

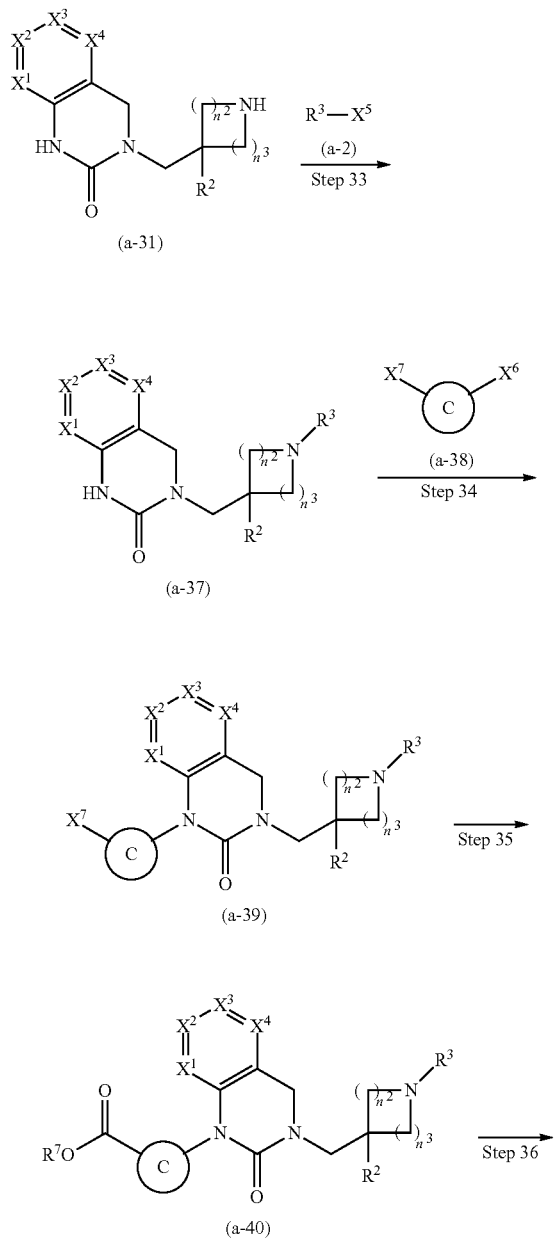

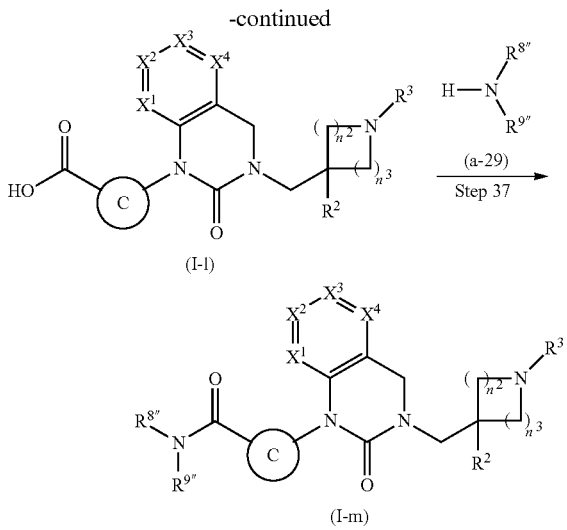

(wherein, X$^7$ represents a chlorine atom, a bromine atom, an iodine atom, methanesulfonyloxy, trifluoromethanesulfonyloxy, benzenesulfonyloxy, p-toluenesulfonyloxy, or the like, the ring C represents an aryl moiety of optionally substituted aryl (the aryl moiety may further has a substituent) or an aromatic heterocyclic group moiety of an optionally substituted aromatic heterocyclic group (the aromatic heterocyclic group moiety may further has a substituent) in the definition of R$^1$, and X$^1$, X$^2$, X$^3$, X$^4$, X$^5$, X$^6$, R$^2$, R$^3$, R$^{8''}$, R$^{9''}$, n$^2$ and n$^3$ have the same definitions as described above, respectively)

Step 33

Compound (a-37) can be produced in the same manner as in the above-mentioned Step 2 using Compound (a-31) and Compound (a-2).

Step 34

Compound (a-39) can be produced in the same manner as in the above-mentioned Step 7 using Compound (a-37) and Compound (a-38)

Compound (a-38) is obtained as a commercially available product or can be obtained by a known method [for example, Jikken Kagaku Koza, 5th Ed., vol. 13, p. 341, Maruzen Co., Ltd. (2003), or the like] or a modified method thereof.

Step 35

Compound (a-40) can be produced in the same manner as in the above-mentioned Step 24 using Compound (a-39).

Step 36

Compound (I-1) can be produced in the same manner as in the above-mentioned Step 25 using Compound (a-40).

Step 37

Compound (I-m) can be produced in the same manner as in the above-mentioned Step 26 using Compound (I-1) and Compound (a-29).

Production Process 9

Among Compounds (I), Compound (I-n), in which n$^1$ is 0 and R$^1$ is optionally substituted aryl or an optionally substituted aromatic heterocyclic group, and the group is aryl substituted with —CONH$_2$ (the aryl group may further has another substituent) or an aromatic heterocyclic group substituted with —CONH$_2$ (the aromatic heterocyclic group may further has another substituent), can also be produced according to, for example, the following method.

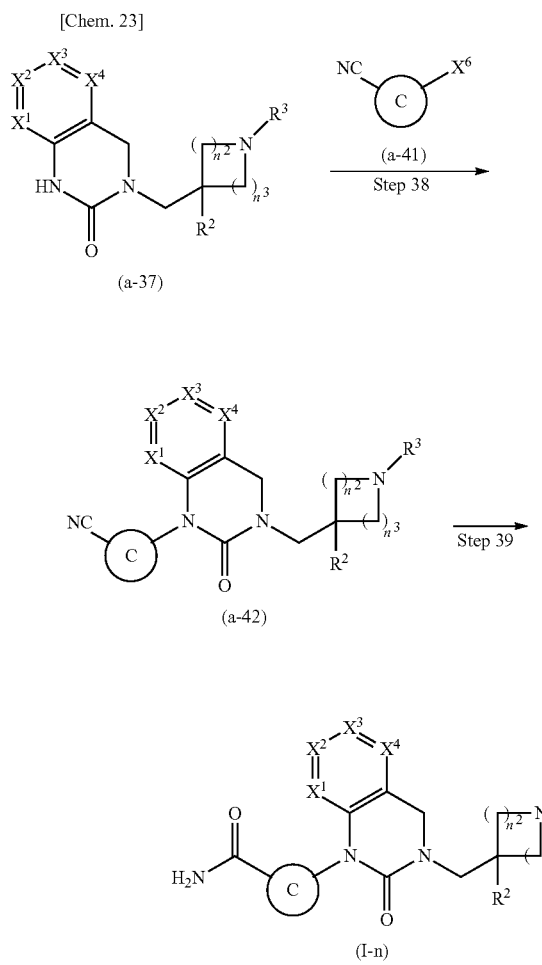

(wherein, the ring C, $X^1$, $X^2$, $X^3$, $X^4$, $X^6$, $R^2$, $R^3$, $n^2$ and $n^3$ have the same definitions as described above, respectively)

Step 38

Compound (a-42) can be produced in the same manner as in the above-mentioned Step 7 using Compound (a-37) and Compound (a-41).

Compound (a-41) is obtained as a commercially available product or can be obtained by a known method [for example, Jikken Kagaku Koza, 5th Ed., vol. 13, p. 341, Maruzen Co., Ltd. (2003), or the like] or a modified method thereof.

Step 39

Compound (I-n) can be produced in the same manner as in the above-mentioned Step 25 using Compound (a-42).

Production Process 10

Compound (IA) can be produced according to the above-mentioned production process 1 to 11. Also, among Compounds (IA), a compound in which $n^1$ is 0 and $R^1$ is a hydrogen atom can be produced by the method described in Chemical & Pharmaceutical Bulletin 1990, 38(6), 1591 or a modified method thereof.

The conversion of a functional group contained in $R^{1A}$, $R^{2A}$ or $R^{3A}$ in Compound (IA) and in $R^1$, $R^2$ or $R^3$ in Compound (I) can also be performed by a known method [for example, the method described in Comprehensive Organic Transformations 2nd edition, written by R. C. Larock, Vch Verlagsgesellschaft Mbh (1999), or the like] or a modified method thereof.

The intermediates and the target compounds in the above-mentioned respective production processes can be isolated and purified by being subjected to a separation and purification method conventionally used in the organic synthetic chemistry, for example, filtration, extraction, washing, drying, concentration, recrystallization, various types of chromatography, or the like. Also, the intermediates can be subjected to the subsequent reaction without being particularly purified.

Among Compounds (IA) and (I), some compounds may exist as a stereoisomer such as a geometric isomer or an optical isomer, a tautomer, or the like. The present invention encompasses all possible isomers and mixtures thereof including these isomers.

Part or all of the respective atoms in Compounds (IA) and (I) may be replaced by corresponding isotope atom(s), respectively, and the present invention also comprises such compounds replaced by isotope atom(s). For example, part or all of the hydrogen atom(s) in Compounds (IA) and (I) may be hydrogen atom(s) having an atomic weight of 2 (deuterium atom(s)).

Compounds in which part or all of the respective atom(s) in Compounds (IA) and (I) is/are replaced by corresponding isotope atom(s), respectively, can be produced in the same manner as in the above-mentioned respective production processes using commercially available building blocks. Also, the compounds in which part or all of the hydrogen atom(s) in Compounds (IA) and (I) is/are replaced by deuterium atom(s) can also be synthesized by, for example, 1) a method of deuterating a carboxylic acid and the like under basic conditions using deuterium peroxide (U.S. Pat. No. 3,849,458), 2) a method of deuterating an alcohol, a carboxylic acid, and the like using an iridium complex as a catalyst and also using heavy water as a deuterium source [Journal of the American Chemical Society 2002, 124(10), 2092], 3) a method of deuterating a fatty acid using palladium on carbon as a catalyst and also using only a deuterium gas as a deuterium source [LIPIDS 1974, 9(11), 913], 4) a method of deuterating acrylic acid, methyl acrylate, methacrylic acid, methyl methacrylate, and the like using a metal such as platinum, palladium, rhodium, ruthenium, iridium and the like as a catalyst and also using heavy water, or heavy water and a deuterium gas, as a deuterium source (JPH5-19536, JPS61-277648, and JPS61-275241), 5) a method of deuterating acrylic acid, methyl methacrylate, and the like using a catalyst such as palladium, nickel, copper, chromite copper and the like, and also using heavy water as a deuterium source (JPS63-198638), and the like.

In the case where a salt of Compound (IA) or (I) is desired to be obtained, when Compound (IA) or (I) is obtained in the form of a salt, the salt may be directly purified. Or, when Compound (IA) or (I) is obtained in a free form, Compound (IA) or (I) is dissolved or suspended in a suitable solvent, and an acid or a base is added thereto to form a salt, and then, the salt may be isolated and purified.

Further, Compounds (IA) and (I) and pharmaceutically acceptable salts thereof may exist in the form of adducts with water or any of various solvents, and the present invention also comprises these adducts.

Specific examples of Compounds (IA) and (I) obtained according to the present invention are shown in Table 1 to Table 5. However, the compounds of the present invention are not limited thereto.

TABLE 1

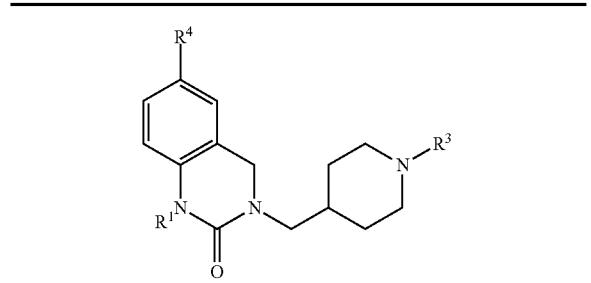

| Compound No. | R¹ | R³ | R⁴ |
|---|---|---|---|
| 1 | 2-carbamoylphenyl-CH₂- | 6,7-dimethoxyquinazolin-4-yl | H |
| 2 | tetrahydrofuran-2-yl-CH₂- | 6,7-dimethoxyquinazolin-4-yl | H |
| 3 | 2-cyanophenyl-CH₂- | [1,3]dioxolo[4,5-g]quinazolin-8-yl | H |
| 4 | 2-cyanophenyl-CH₂- | benzo[d][1,2,3]triazin-4-yl | H |
| 5 | 2-cyanophenyl-CH₂- | 6,7-dimethoxyquinazolin-4-yl | SO₂CH₃ |
| 6 | 3-cyanophenyl-CH₂- | 6,7-dimethoxyquinazolin-4-yl | H |

TABLE 1-continued

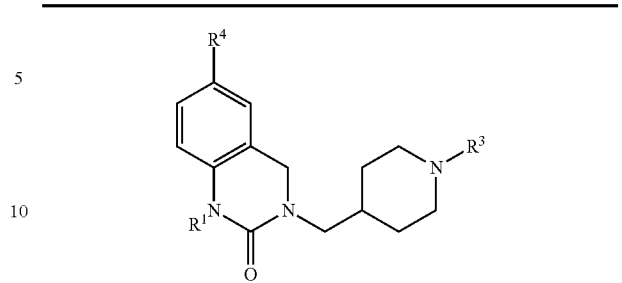

| Compound No. | R¹ | R³ | R⁴ |
|---|---|---|---|
| 7 | 2-fluoro-5-cyanophenyl- | 6,7-dimethoxyquinazolin-4-yl | H |
| 8 | 3-nitrophenyl- | 6,7-dimethoxyquinazolin-4-yl | H |
| 9 | 2-cyanopyridin-4-yl- | 6,7-dimethoxyquinazolin-4-yl | H |
| 10 | 4-cyanopyridin-2-yl- | 6,7-dimethoxyquinazolin-4-yl | H |
| 11 | 2-cyanopyrimidin-4-yl- | 6,7-dimethoxyquinazolin-4-yl | H |
| 12 | 3-cyano-2-oxo-1,2-dihydropyridin-5-yl- | 6,7-dimethoxyquinazolin-4-yl | H |
| 13 | 3-sulfamoylphenyl- | 6,7-dimethoxyquinazolin-4-yl | H |

TABLE 1-continued

[Structure: R⁴-substituted benzene fused to a 6-membered ring containing R¹-N, N-CH₂-piperidine-N-R³, with C=O]

| Compound No. | R¹ | R³ | R⁴ |
|---|---|---|---|
| 14 | 4-pyridyl with 2-C(O)NH₂ | 6,7-dimethoxyquinazolin-4-yl | H |
| 15 | 4-phenyl with 2-CN and HO₂C | 6,7-dimethoxyquinazolin-4-yl | H |
| 16 | tetrahydropyran-4-yl | 6,7-dimethoxyquinazolin-4-yl | H |

TABLE 2

| Compound No. | Structure |
|---|---|
| 17 | [Quinazolinone with 2-cyanopyridin-4-yl on N1, CH₂-azetidine-N-(6,7-dimethoxyquinazolin-4-yl)] |
| 18 | [Quinazolinone with 2-cyanopyridin-4-yl on N1, CH₂-(4-hydroxy)piperidine-N-(6,7-dimethoxyquinazolin-4-yl)] |
| 19 | [Quinazolinone with 2-cyanopyridin-4-yl on N1, with NH-piperidine-N-(6,7-dimethoxyquinazolin-4-yl) at the 3-position] |
| 20 | [Quinazolinedione with 3-cyanophenyl on N1, CH₂-piperidine-N-(6,7-dimethoxyquinazolin-4-yl)] |
| 21 | [Pyrido-fused uracil with 2-cyanopyridin-4-yl on N1, CH₂-piperidine-N-(6,7-dimethoxyquinazolin-4-yl)] |
| 22 | [Pyrido-fused uracil isomer with 2-cyanopyridin-4-yl on N1, CH₂-piperidine-N-(6,7-dimethoxyquinazolin-4-yl)] |

TABLE 3

[Core structure: X¹X²X³X⁴-fused ring with N-(3-cyano, Z²-substituted phenyl), CH₂-piperidine-N-R³, C=O]

| Compound No. | R³ | X¹X²X³X⁴ ring | Z² |
|---|---|---|---|
| 23 | pyrido[3,4-d]pyrimidin-4-yl | pyrimidine fused | 4-fluoropyridin-N |

TABLE 3-continued

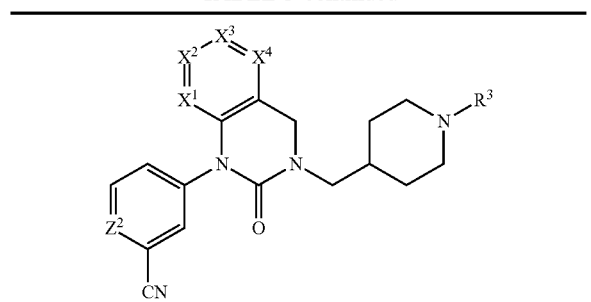

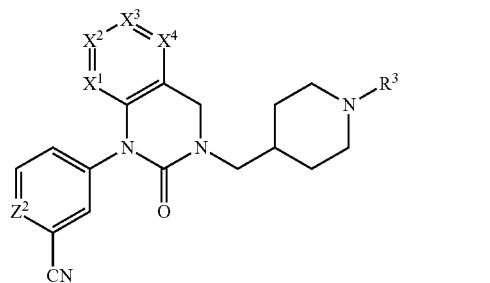

| Compound No. | R³ | X¹=X²−X³=X⁴ | Z² |
|---|---|---|---|
| 24 | 7,8-dimethoxyquinazolin-4-yl (OCH₃, OCH₃) | N=CH−N=CH | N |
| 25 | quinazoline-7-carboxylic acid-4-yl | CH=CH−CH=CH | CH |
| 26 | N-methylquinazoline-7-carboxamide-4-yl | CH=CH−CH=CH | CH |
| 27 | 7-(4-methylpiperazine-1-carbonyl)quinazolin-4-yl | CH=CH−CH=CH | N |
| 28 | quinazoline-7-carboxamide-4-yl | CH=CH−CH=CH | N |
| 29 | pyrido[3,4-d]pyrimidine N-oxide-4-yl | CH=CH−CH=CH | CH |
| 30 | imidazo[1,2-a]pyrazin-8-yl | CH=CH−CH=CH | N |
| 31 | 7H-pyrrolo[2,3-d]pyrimidin-4-yl | CH=CH−CH=CH | N |
| 32 | 5-methoxypyrimidin-4-yl | CH=CH−CH=CH | N |
| 33 | 6-aminopyrido[3,4-d]pyrimidin-4-yl | CH=CH−CH=CH | N |
| 34 | 6-oxo-5,6-dihydropyrido[3,4-d]pyrimidin-4-yl | CH=CH−CH=CH | N |
| 35 | 7-oxo-7,8-dihydro-6H-pyrimido[5,4-b][1,4]oxazin-4-yl | CH=CH−CH=CH | N |
| 36 | 8-oxo-7,8-dihydro-9H-purin-6-yl | CH=CH−CH=CH | N |
| 37 | 7-morpholinoquinazolin-4-yl | CH=CH−CH=CH | N |

TABLE 3-continued

[Structure: pyrimidinone core with X1-X4 ring, N-phenyl(Z2, CN), piperidine-N-R3]

| Compound No. | R3 | X1-X4 ring | Z2 |
|---|---|---|---|
| 38 | [1,2,4]triazolo[4,3-a]pyridin-3(2H)-one | CH-CH | N |

TABLE 4

[Structure: pyrimidinone core with X1-X4 ring, N-phenyl(Z2, CN), piperidine-N-R3]

| Compound No. | R3 | X1-X4 ring | Z2 |
|---|---|---|---|
| 39 | [1,2,4]triazolo[4,3-a]pyrazin-3(2H)-one | CH-CH | N |
| 40 | 2-fluoro-pyridine-3-carboxamide | CH-CH | N |
| 41 | 3-amino-pyrido[3,2-d]pyrimidine | CH-CH | N |

TABLE 4-continued

| Compound No. | R3 | X1-X4 ring | Z2 |
|---|---|---|---|
| 42 | pyrido[3,4-d]pyrimidin-4(3H)-one | CH-CH | N |
| 43 | 5H-pyrano[4,3-d]pyrimidine | CH-CH | CH |
| 44 | 6-acetyl-5,6,7,8-tetrahydropyrido[4,3-d]pyrimidine | CH-CH | CF |
| 45 | pyrido[3,4-d]pyrimidine-6-carboxamide | CH-CH | CF |
| 46 | pyrido[3,4-d]pyrimidine-6-carboxamide | CH-N | CF |
| 47 | pyrido[3,4-d]pyrimidin-4(3H)-one | CH-N | CF |

TABLE 5
| Compound No. | |
|---|---|
| 48 | 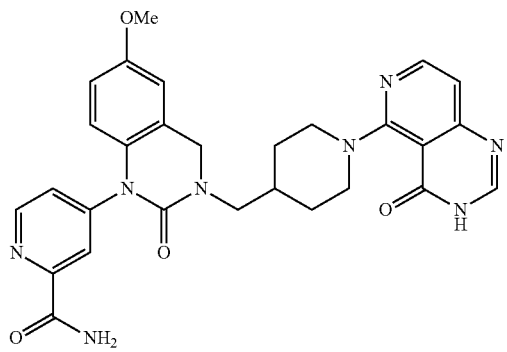 [SMILES: COc1ccc2c(c1)CN(CC1CCN(c3nccc4nc[nH]c(=O)c34)CC1)C(=O)N2c1ccnc(C(N)=O)c1] |
| 49 | 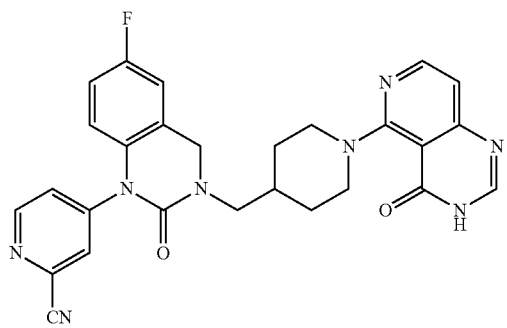 [SMILES: N#Cc1cc(N2C(=O)N(CC3CCN(c4nccc5nc[nH]c(=O)c45)CC3)Cc3cc(F)ccc32)ccn1] |
| 50 | 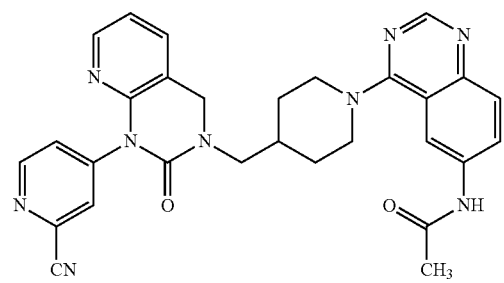 [SMILES: CC(=O)Nc1ccc2ncnc(N3CCC(CN4Cc5cccnc5N(c5ccnc(C#N)c5)C4=O)CC3)c2c1] |
| 51 | 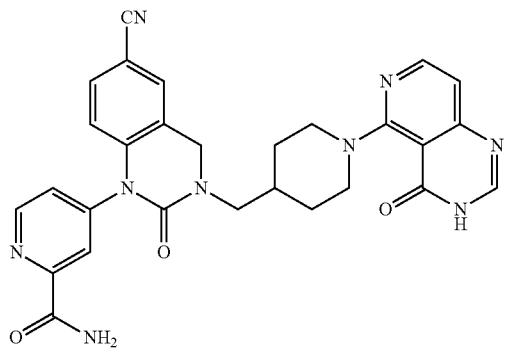 [SMILES: N#Cc1ccc2c(c1)CN(CC1CCN(c3nccc4nc[nH]c(=O)c34)CC1)C(=O)N2c1ccnc(C(N)=O)c1] |

TABLE 5-continued

| Compound No. | |
|---|---|
| 52 | 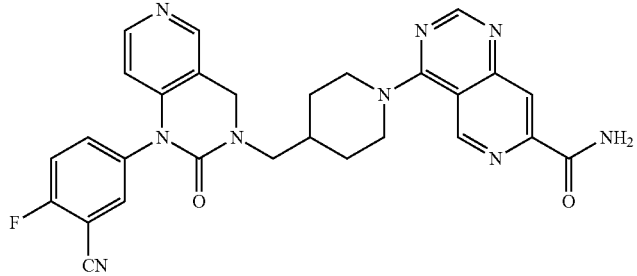 [SMILES: N#Cc1cc(N2C(=O)N(CC3CCN(c4ncnc5cc(C(N)=O)ncc45)CC3)Cc3cnccc32)ccc1F] |
| 53 | 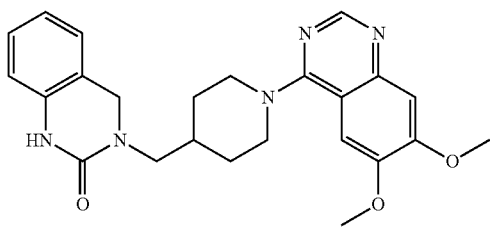 [SMILES: COc1cc2ncnc(N3CCC(CN4Cc5ccccc5NC4=O)CC3)c2cc1OC] |

Next, the pharmacological activity of representative Compound (I) will be specifically described by way of Test Examples.

Test Example 1: Inhibitory Activity Against T-Cell Factor (TCF)-Luciferase Reporter Using Wnt Pathway as Index The inhibitory activity of test compounds against Wnt pathway was evaluated by the following method.

A human colorectal adenocarcinoma cell line DLD-1 (Japanese Collection of Research Bioresources) was cultured in RPMI-1640 medium (Gibco/Life Technologies, Inc.) containing 10% fetal bovine serum (Gibco/Life Technologies, Inc.), 10 mmol/L of a 4-(2-hydroxyethyl)-1-piperazineethanesulfonic acid (HEPES) buffer solution (Gibco/Life Technologies, Inc.), 1 mmol/L of a sodium pyruvate solution (Gibco/Life Technologies, Inc.), 4.5 g/L of a D-(+)-glucose solution (Sigma-Aldrich, Inc.), 100 units/mL penicillin (Gibco/Life Technologies, Inc.) and 100 μg/mL of streptomycin (Gibco/Life Technologies, Inc.) under the conditions of 37° C. and 5% carbon dioxide gas. The DLD-1 cells were seeded in a 10 cm dish, and 20 μg of a luciferase gene plasmid pGL4.27 having a TCF responsive sequence inserted therein was transfected into the cells using 10 μL of Attractene (Qiagen, Inc.) according to the protocol attached to the product. A stably expressing cell line (DLD-1/TCF-Luc) was selected using 600 μg/μL of hygromycin B (Wako Pure Chemical Industries Ltd.). The DLD-1/TCF-Luc cells were detached with trypsin and seeded in a 384-well plate, and a test compound was added at different concentrations. After 18 hours, the luciferase activity was measured using Steady-Glo™ Luciferase Assay System (Promega, Inc.).

The inhibition ratio was obtained according to the following formula 1. The inhibition ratio (%) of the compound of the present invention at 1 μmol/L against the TCF-luciferase reporter using the Wnt pathway as an index is shown in Table 6.

[Math. 1]

Inhibition ratio (%)=100−{(luciferase activity when test compound was added)−(luciferase activity of blank)}/{(luciferase activity of control)−(luciferase activity of blank)}×100    Formula 1

TABLE 6

| Compound No. | Inhibition ratio (%) at 1 μmol/L | Compound No. | Inhibition ratio (%) at 1 μmol/L |
|---|---|---|---|
| 1 | 88 | 2 | 87 |
| 3 | 77 | 4 | 74 |
| 5 | 84 | 6 | 76 |
| 7 | 76 | 8 | 73 |
| 9 | 74 | 10 | 79 |
| 11 | 87 | 12 | 80 |
| 13 | 80 | 14 | 76 |
| 15 | 84 | 16 | 63 |
| 17 | 76 | 18 | 80 |
| 19 | 91 | 20 | 83 |
| 21 | 76 | 22 | 75 |
| 23 | 84 | 24 | 86 |
| 25 | 86 | 26 | 77 |
| 27 | 88 | 28 | 84 |
| 29 | 74 | 30 | 69 |
| 31 | 74 | 32 | 76 |
| 33 | 82 | 34 | 78 |
| 35 | 79 | 36 | 79 |
| 37 | 82 | 38 | 89 |
| 39 | 89 | 40 | 78 |
| 41 | 81 | 42 | 81 |
| 43 | 85 | 44 | 82 |
| 45 | 86 | 46 | 84 |
| 47 | 82 | 48 | 84 |
| 49 | 82 | 50 | 87 |
| 51 | 90 | 52 | 81 |

From the above results, it was shown that Compounds (IA) and (I) and pharmaceutically acceptable salts thereof inhibit Wnt signaling, and therefore are useful as a therapeutic and/or preventive agent for a disease associated with Wnt signaling, for example, cancer, pulmonary fibrosis, fibromatosis, osteoarthritis, and the like.

Test Example 2: Tankyrase-2 Enzyme Inhibition Test

The enzyme activity of tankyrase-2 was evaluated using Tankyrase-2 Chemiluminescent Assay Kit (BPS Bioscience, Inc., Catalog No. 80566). The Tankyrase-2 Chemiluminescent Assay Kit is a kit for evaluating the enzyme activity of tankyrase-2 using autoribosylation of glutathione-S-transferase (GST)-tankyrase-2 fusion protein as an index. All the experimental materials except for PBS (PBST) buffer containing phosphate-buffered saline (PBS) and 0.05% Tween 20 are all included in the kit. The GST-tankyrase-2 enzyme diluted with 50 µL of 1× tankyrase buffer was added to the wells of a 96-well plate coated with glutathione. After the plate was left to stand overnight at 4° C., the plate was washed 3 times with the PBST buffer. 150 µL of blocking buffer was added thereto, and the plate was left to stand at room temperature for 30 minutes to block the wells. The plate was washed 3 times with the PBST buffer. Before the ribosylation reaction, an assay mixture containing a biotinylated substrate and a test compound diluted with 1× tankyrase buffer were mixed, whereby a reaction mixture was prepared. In order to start the ribosylation reaction, 50 µL of the reaction mixture was added to the wells. In a blank well, 1× tankyrase buffer was added in place of the reaction mixture containing a biotinylated substrate. The plate was left to stand at 30° C. for 1 hour. After the reaction, the plate was washed 3 times with the PBST buffer. Streptavidin-horseradish peroxidase (HRP) was diluted to 50-fold with the blocking buffer. The diluted streptavidin-HRP was added to the wells, and the plate was left to stand at room temperature for 30 minutes. The plate was washed 3 times with the PBST buffer. Immediately before use, 50 µL of the HRP chemiluminescent substrate A and 50 µL of the HRP chemiluminescent substrate B were mixed and 100 µL of the resulting mixture was added to the wells. The chemiluminescence was measured using a chemiluminescence measuring apparatus. The inhibition ratio was obtained according to the following formula 2. The tankyrase-2 enzyme inhibitory activity of the compound of the present invention is shown in Table 7.

[Math. 2]

$$\text{Inhibition ratio (\%)} = 100 - \{(\text{chemiluminescence intensity when test compound was added}) - (\text{chemiluminescence intensity of blank})\} / \{(\text{chemiluminescence intensity of control}) - (\text{chemiluminescence intensity of blank})\} \times 100 \quad \text{Formula 2}$$

TABLE 7

| Compound No. | Inhibition ratio (%) at 1 µmol/L | Compound No. | Inhibition ratio (%) at 1 µmol/L |
| --- | --- | --- | --- |
| 1 | 91 | 2 | 91 |
| 5 | 94 | 7 | 95 |
| 8 | 90 | 9 | 91 |
| 12 | 88 | 13 | 89 |
| 15 | 92 | 16 | 71 |
| 18 | 79 | 21 | 93 |
| 22 | 98 | 24 | 92 |
| 25 | 81 | 29 | 87 |
| 30 | 92 | 32 | 94 |
| 34 | 87 | 35 | 88 |
| 36 | 88 | 37 | 87 |
| 38 | 94 | 40 | 93 |
| 41 | 92 | 44 | 93 |
| 47 | 80 | 48 | 93 |
| 50 | 82 | 53 | 100 |

From the above results, it was shown that Compounds (IA) and (I) and pharmaceutically acceptable salts thereof inhibit the tankyrase-2 enzyme. That is, it was shown that Compounds (IA) and (I) and pharmaceutically acceptable salts thereof inhibit Wnt signaling by inhibiting tankyrase, and therefore are useful as a therapeutic and/or preventive agent for a disease associated with Wnt signaling, for example, cancer, pulmonary fibrosis, fibromatosis, osteoarthritis, and the like.

Compounds (IA) and (I) and pharmaceutically acceptable salts thereof can be administered alone as they are, but are generally desirably provided as various pharmaceutical preparations. Also, such pharmaceutical preparations are used for animals and human beings.

The pharmaceutical preparation according to the present invention can contain, as an active ingredient, Compound (IA) or (I) or a pharmaceutically acceptable salt thereof alone or as a mixture with an active ingredient for any other treatment. Also, such a pharmaceutical preparation is prepared by mixing the active ingredient with one or more pharmaceutically acceptable carriers (for example, a diluent, a solvent, an excipient, and the like) and then subjecting the mixture to any method well known in the technical field of drug formulation study.

As the administration route, it is preferred to use the most effective route of administration in the treatment. Examples of the administration route include oral administration and parenteral administration such as intravenous administration or the like.

Examples of the administration form include a tablet, an injection, and the like.

A suitable administration form for the oral administration, for example, a tablet or the like can be prepared by using an excipient such as lactose and the like, a disintegrator such as starch and the like, a lubricant such as magnesium stearate and the like, a binder such as hydroxypropyl cellulose and the like, and the like.

A suitable administration form for the parenteral administration, for example, an injection or the like can be prepared by using a diluent or a solvent such as a salt solution, a glucose solution, or a mixed solution of a salt solution and a glucose solution, and the like, and the like.

The dose and the frequency of administration of Compound (IA) or (I) or a pharmaceutically acceptable salt thereof may vary depending on administration form, age and body weight of a patient, nature or seriousness of the symptom to be treated, and the like. However, in the oral administration, in general, a dose of 0.01 to 1000 mg, preferably, 0.05 to 100 mg, is administered to an adult patient once or several times a day. In the parenteral administration such as intravenous administration, a dose of 0.001 to 1000 mg, preferably, 0.01 to 100 mg, is administered to an adult patient once or several times a day. However, such dose and frequency of administration vary depending on the above-mentioned various conditions.

Hereinafter, the present invention will be more specifically described by way of Examples and Reference Examples, however, the scope of the present invention is not limited to these Examples.

Incidentally, the proton nuclear magnetic resonance spectrum ($^1$H NMR) used in the Examples and Reference Examples was measured at 270 MHz, 300 MHz or 400 MHz, and exchangeable protons may not be clearly observed depending on the compound and measurement conditions. Incidentally, the multiplicity of signals is expressed in conventional terms, and the term "br" indicates an apparent broad signal.

Also, each synthesized compound was named using ChemBioDraw Ultra ver. 12.0.

Reference Example 1

3-(Piperidin-4-ylmethyl)-3,4-dihydroquinazolin-2(1H)-one hydrochloride (Compound R1)

Step 1: After 2-nitrobenzaldehyde (5.60 g, 37.1 mmol) and tert-butyl 4-(aminomethyl)piperidine-1-carboxylate (8.00 g, 37.3 mmol) were stirred in methanol at room temperature for 1 hour, sodium cyanoborohydride (4.70 g, 74.8 mmol) was added thereto, and the resulting mixture was stirred overnight at room temperature. After the reaction mixture was concentrated under reduced pressure, water was added thereto, and the resulting mixture was extracted with ethyl acetate. The organic layer was washed with saturated brine, and then dried over anhydrous magnesium sulfate and concentrated under reduced pressure. The resulting residue was purified by silica gel column chromatography (a chloroform/methanol mixed solvent), whereby tert-butyl 4-[(2-nitrobenzylamino)methyl]-piperidine-1-carboxylate (5.00 g, yield: 40%) was obtained.

Step 2: Tert-butyl 4-[(2-nitrobenzylamino)methyl]-piperidine-1-carboxylate (10.0 g, 28.6 mmol) obtained in Step 1 was dissolved in methanol (100 mL), and palladium-carbon (10.0 wt %, 1.00 g) was added thereto, and the resulting mixture was stirred under a hydrogen gas (atmospheric pressure) atmosphere at room temperature for 12 hours. After completion of the reaction, the reaction mixture was treated with diatomaceous earth, and then, the solvent was evaporated under reduced pressure, whereby tert-butyl 4-[(2-aminobenzylamino)methyl]-piperidine-1-carboxylate (8.00 g, yield: 88%) was obtained.

Step 3: Tert-butyl 4-[(2-aminobenzylamino)methyl]-piperidine-1-carboxylate (10.6 g, 27.7 mmol) obtained in Step 2, N,N'-carbonyldiimidazole (11.2 g, 69.3 mmol) and triethylamine (8.11 mL, 58.2 mmol) were refluxed in acetonitrile (110 mL) for 2 hours. After the reaction mixture was cooled to room temperature, water was added thereto, and the deposited solid was collected by filtration, whereby tert-butyl 4-(2-oxo-1,4-dihydro-2H-quinazolin-3-ylmethyl)piperidine-1-carboxylate (8.63 g, yield: 93%) was obtained.

ESI-MS m/z: 346 (M+H)$^+$, $^1$H-NMR (300 MHz, CDCl$_3$, δ): 7.20-7.15 (m, 1H), 7.05-7.03 (m, 1H), 6.97-6.88 (m, 2H), 6.67 (d, J=7.2 Hz, 1H), 4.46 (s, 2H), 4.09 (brs, 2H), 3.31 (br s, 2H), 2.73-2.64 (m, 2H), 1.97-1.84 (m, 1H), 1.70-1.66 (m, 2H), 1.45 (s, 9H), 1.28-1.12 (m, 2H)

Step 4: To tert-butyl 4-(2-oxo-1,4-dihydro-2H-quinazolin-3-ylmethyl)piperidine-1-carboxylate (13.0 g, 37.6 mmol) obtained in Step 3, a hydrochloric acid-dioxane solution (4.00 mol/L, 150 mL) was added in an ice bath, and the resulting mixture was stirred at room temperature for 4 hours. The reaction mixture was concentrated under reduced pressure, whereby the title Compound R1 (10.5 g, yield: 99%) was obtained.

ESI-MS m/z: 246 (M+H)$^+$

Reference Example 2

2-{[2-Oxo-3-(piperidin-4-ylmethyl)-3,4-dihydroquinazolin-1(2H)-yl]methyl}benzonitrile hydrochloride (Compound R2)

Step 1: Tert-butyl 4-{[1-(2-cyanobenzyl)-2-oxo-1,2-dihydroquinazolin-3(4H)-yl]methyl}piperidine-1-carboxylate (2.27 g, 85%) was obtained in the same manner as in Step 1 of Example 1 using tert-butyl 4-(2-oxo-1,4-dihydro-2H-quinazolin-3-ylmethyl)piperidine-1-carboxylate obtained in Step 3 of Reference Example 1 and 2-cyanobenzyl bromide.

ESI-MS m/z: 461 (M+H)$^+$, $^1$H-NMR (400 MHz, CDCl$_3$, δ): 7.68 (d, J=7.8 Hz, 1H), 7.49 (t, J=7.3 Hz, 1H), 7.33 (t, J=7.3 Hz, 1H), 7.22 (d, J=7.8 Hz, 1H), 7.14-7.08 (m, 2H), 6.97 (t, J=7.3 Hz, 1H), 6.55 (d, J=7.8 Hz, 1H), 5.33 (s, 2H), 4.51 (s, 2H), 4.14-4.09 (br m, 2H), 3.43-3.35 (br m, 2H), 2.74-2.67 (br m, 2H), 1.97-1.90 (m, 1H), 1.74-1.67 (m, 2H), 1.45 (s, 9H), 1.26-1.19 (m, 2H)

Step 2: The title Compound R2 (1.79 g, 92%) was obtained in the same manner as in Step 4 of Reference Example 1 using tert-butyl 4-{[1-(2-cyanobenzyl)-2-oxo-1,2-dihydroquinazolin-3(4H)-yl]methyl}piperidine-1-carboxylate obtained in Step 1.

ESI-MS m/z: 361 (M+H)$^+$

Reference Example 3

5-Iodo-2-oxo-1-{[2-(trimethylsilyl)ethoxy]methyl}-1,2-dihydropyridine-3-carbonitrile (Compound R3)

Step 1: 2-Hydroxynicotinonitrile (1.00 g, 8.33 mmol), iodine (2.54 g, 9.99 mmol) and potassium carbonate (1.38 g, 9.99 mmol) were stirred overnight in DMF (10 mL) at room temperature. To the reaction mixture, water was added, and the resulting mixture was extracted with a chloroform/2-propanol mixed solvent. The organic layer was dried over anhydrous magnesium sulfate, and then concentrated under reduced pressure. To the resulting residue, (2-chloromethoxyethyl)trimethylsilane (SEM-Cl) (1.67 g, 10.0 mmol) and potassium hydroxide (560 mg, 10.0 mmol) were added, and the resulting mixture was stirred in THF (25.0 mL) at room temperature for 3 hours. To the reaction mixture, water was added, and the resulting mixture was extracted with ethyl acetate. The organic layer was washed with saturated brine, and then dried over anhydrous magnesium sulfate and concentrated under reduced pressure. The resulting residue was purified by silica gel column chromatography (an ethyl acetate/heptane mixed solvent), whereby the title Compound R3 (372 mg, yield: 12%) was obtained.

ESI-MS m/z: 377 (M+H)$^+$, $^1$H-NMR (300 MHz, CDCl$_3$, δ): 7.89 (d, J=2.6 Hz, 1H), 7.86 (d, J=2.6 Hz, 1H), 5.31 (s, 2H), 3.64 (t, J=8.3 Hz, 2H), 0.95 (t, J=8.3 Hz, 2H), −0.01 (s, 9H)

Reference Example 4

Tert-butyl 3-iodophenylsulfonyl{[2-(trimethylsilyl)ethoxy]methyl}carbamate (Compound R4)

Step 1: 3-Iodobenzenesulfonamide (100 mg, 0.353 mmol), di-tert-butyl dicarbonate (Boc$_2$O) (116 mg, 0.530 mmol), DMAP (8.63 mg, 0.071 mmol) and triethylamine (54.0 mg, 0,530 mmol) were stirred in dichloromethane (1.50 mL) at room temperature for 3 hours. To the reaction mixture, water was added, and the resulting mixture was extracted with chloroform. The organic layer was washed with saturated brine, and then dried over anhydrous magnesium sulfate and concentrated under reduced pressure. The resulting residue was purified by silica gel column chromatography (a methanol/chloroform mixed solvent), whereby tert-butyl 3-iodophenylsulfonylcarbamate (100 mg, yield: 74%) was obtained.

ESI-MS m/z: 384 (M+H)$^+$

Step 2: The title Compound R4 (120 mg, yield: 90%) was obtained in the same manner as in Step 1 of Example 14 using tert-butyl 3-iodophenylsulfonylcarbamate obtained in Step 1. $^1$H-NMR (300 MHz, CDCl$_3$, δ): 8.36-8.35 (m, 1H), 8.02-7.98 (m, 1H), 7.95-7.91 (m, 1H), 7.28-7.23 (m, 1H), 5.30 (s, 2H), 3.59-3.54 (m, 2H), 1.37 (s, 9H), 1.03-0.98 (m, 2H), 0.00 (s, 9H) ESI-MS m/z: 514 (M+H)$^+$ Reference Example 5

Tert-butyl 4-oxo-3,4-dihydroquinazoline-7-carboxylate (Compound R5)

4-Tert-butyl-1-methyl-1-aminoterephthalic acid (55 mg, 0.22 mmol) obtained by the method described in Journal of Medicinal Chemistry 1999, 42, 545 and formamidine acetate (46 mg, 0.44 mmol) were refluxed overnight in ethanol (2.0 ml). After the solvent was evaporated under reduced pressure, the resulting residue was purified by silica gel column chromatography (a chloroform/methanol mixed solvent), whereby the title Compound R5 (28 mg, yield: 51%) was obtained.

ESI-MS m/z: 247 (M+H)$^+$, $^1$H-NMR (300 MHz, CDCl$_3$, δ): 8.37 (s, 1H), 8.34 (d, J=8.4 Hz, 1H), 8.11-8.07 (m, 2H), 1.64 (s, 9H)

Reference Example 6

4-Chloro-5H-pyrido[4,5-b][1,4]oxazin-6(7H)-one (Compound R6)

Step 1: Methyl glycolate (488 mg, 5.4 mmol) was dissolved in DMF (20 mL), and in an ice bath, sodium hydride (about 60 wt %, 268 mg) was added thereto, and the resulting mixture was stirred for 30 minutes. Thereafter, a DMF solution (2.0 mL) of 4,6-dichloro-5-nitropyrimidine (1.0 g, 5.1 mmol) was added dropwise thereto, and the resulting mixture was stirred overnight at room temperature. To the reaction mixture, ice water was added, and then, the resulting mixture was extracted with ethyl acetate. The organic layer was washed with saturated brine and dried over anhydrous magnesium sulfate, and then, the solvent was evaporated under reduced pressure. The resulting residue was purified by silica gel column chromatography (a hexane/ethyl acetate mixed solvent), whereby methyl 2-(6-chloro-5-nitropyrimidin-4-yloxy)acetate (584 mg, 46%) was obtained.

$^1$H-NMR (400 MHz, CDCl$_3$ δ): 8.62 (s, 1H), 5.08 (s, 2H), 3.80 (s, 3H)

Step 2: Methyl 2-(6-chloro-5-nitropyrimidin-4-yloxy)acetate (0.58 g, 2.3 mmol) obtained in Step 1 and reduced iron (654 mg, 12 mmol) were heated in acetic acid (15 mL) at 80° C. for 6 hours. The reaction mixture was treated with diatomaceous earth, and a residue obtained by evaporating the solvent under reduced pressure was purified by silica gel column chromatography (a hexane/ethyl acetate mixed solvent), whereby the title Compound R6 (270 mg, yield: 62%) was obtained.

$^1$H-NMR (300 MHz, DMSO-d$_6$, δ): 11.0 (br s, 1H), 8.28 (s, 1H), 4.95 (s, 2H)

Reference Example 7

8-Chloro-[1,2,4]triazolo[4,3-a]pyrazin-3(2H)-one (Compound R7)

2-Chloro-3-hydrazinylpyrazine (710 mg, 0.49 mmol) obtained by the method described in WO2008/130951 was dissolved in acetonitrile (12 mL), and 1,1'-carbonyldiimidazole (1.6 g, 9.8 mmol) was added thereto, and then, the resulting mixture was stirred at room temperature for 4 hours. To the reaction mixture, water was added, and the deposited solid was collected by filtration, whereby the title Compound R7 (117 mg, yield: 14%) was obtained.

$^1$H-NMR (400 MHz, DMSO-d$_6$, δ): 13.2 (br s, 1H), 7.93 (d, J=4.0 Hz, 1H), 7.34 (d, J=4.0 Hz, 1H)

Reference Example 8

2,3-Difluoroisonicotinamide (Compound R8)

2,3-Difluoroisonicotinic acid (330 mg, 2.1 mmol), an ammonia-methanol solution (about 7.0 mol/L, 5.9 mL), O-(7-aza-1H-benzotriazol-1-yl)-N,N,N',N'-tetramethyluronium hexafluorophosphate (1.6 g, 4.2 mmol) and diisopropylethylamine (1.4 mL) were stirred in DMF (3.0 mL) at room temperature for 5 hours. To the reaction mixture, water was added, and the resulting mixture was extracted with ethyl acetate. The organic layer was washed with saturated brine and dried over anhydrous magnesium sulfate. A residue obtained by concentrating the solvent under reduced pressure was purified by silica gel column chromatography (a chloroform/methanol mixed solvent), whereby the title Compound R8 (239 mg, yield: 73%) was obtained.

$^1$H-NMR (400 MHz, CDCl$_3$, δ): 8.11 (d, J=6.8 Hz, 1H), 7.82-7.77 (m, 1H), 6.59 (br s, 1H), 6.24 (br s, 1H)

Reference Example 9

8-Chloropyrido[3,4-d]pyrimidin-4(3H)-one (Compound R9)

3-Amino-2-chloroisonicotinamide (170 mg, 0.99 mmol) obtained by the method described in Journal of Heterocyclic Chemistry, 2001, 38, 99 was stirred in ethyl triethyl orthoformate (3.0 mL) at 150° C. for 6 hours. The reaction mixture was concentrated under reduced pressure, and a diethyl ether/ethyl acetate (1/1) mixed solvent was added thereto, and the resulting solid was collected by filtration, whereby the title Compound R9 (148 mg, yield: 82%) was obtained.

$^1$H-NMR (300 MHz, DMSO-d$_6$, δ): 12.8 (br s, 1H), 8.42 (d, J=5.1 Hz, 1H), 8.30 (s, 1H), 7.95 (d, J=5.1 Hz, 1H)

Reference Example 10

7,8-Dihydro-3H-pyrano[4,3-d]pyrimidin-4(5H)-one (Compound R10)

Ethyl 4-oxotetrahydro-2H-pyran-3-carboxylate (500 mg, 2.9 mmol) obtained by the method described in US2011/

82138, formamidine acetate (300 mg, 2.9 mmol), and sodium methoxide (500 mg, 9.3 mmol) were refluxed in methanol (20 mL) for 6 hours. To the reaction mixture, water was added, and then, the resulting mixture was extracted with ethyl acetate. The organic layer was washed with saturated brine and dried over anhydrous magnesium sulfate, and then, the solvent was evaporated under reduced pressure, whereby the title Compound R10 (200 mg, yield: 45%) was obtained.

ESI-MS m/z: 153 (M+H)$^+$

Reference Example 11

4,7-Dichloropyrido[4,3-d]pyrimidine (Compound R11)

Step 1: Methyl 4-amino-6-chloronicotinate (15 g, 80 mmol) obtained by the method described in US2012/184562 and sodium hydroxide (13 g, 322 mmol) were stirred in a mixed solution of methanol (100 mL) and water (50 mL) at room temperature for 12 hours. The reaction mixture was adjusted to pH 6 with a 6.0 mol/L aqueous hydrochloric acid solution, and the resulting solid was collected by filtration, whereby 4-amino-6-chloronicotinic acid (8.0 g, yield: 58%) was obtained.

$^1$H-NMR (300 MHz, DMSO-$d_6$, δ): 8.47 (s, 1H), 7.52 (br s, 2H), 6.75 (s, 1H)

Step 2: 4-Amino-6-chloronicotinic acid (7.0 g, 41 mmol) obtained in Step 1 was stirred in thionyl chloride (100 mL) at 80° C. for 12 hours. The reaction mixture was concentrated under reduced pressure, whereby crude 4-amino-6-chloronicotinoyl chloride was obtained. This compound was used in the subsequent reaction without particularly performing further purification.

Step 3: The crude 4-amino-6-chloronicotinoyl chloride obtained in Step 2 was stirred in an aqueous ammonia solution (about 28%, 70 mL) at room temperature for 4 hours. The reaction mixture was extracted with ethyl acetate, and then, the organic layer was washed with saturated brine and dried over anhydrous magnesium sulfate. After the solvent was evaporated under reduced pressure, the resulting residue was purified by silica gel column chromatography using a (dichloromethane/methanol) mixed solvent, whereby 4-amino-6-chloronicotinamide (4.5 g, yield: 72%) was obtained.

$^1$H-NMR (300 MHz, DMSO-$d_6$, δ): 8.37 (s, 1H), 7.97 (br s, 1H), 7.51 (br s, 2H), 7.24 (br s, 1H), 6.65 (s, 1H)

Step 4: 4-Amino-6-chloronicotinamide (4.5 g, 25 mmol) obtained in Step 3 was stirred in trimethyl orthoformate (20 mL) at 150° C. for 5 hours. The reaction mixture was cooled to 0° C., and the resulting solid was collected by filtration, whereby 7-chloropyrido[4,3-d]pyrimidin-4(3H)-one (3.2 g, yield: 70%) was obtained.

$^1$H-NMR (300 MHz, DMSO-$d_6$, δ): 12.8 (br s, 1H), 9.10 (s, 1H), 8.34 (s, 1H), 7.73 (s, 1H)

Step 5: 7-chloropyrido[4,3-d]pyrimidin-4(3H)-one (2.0 g, 11 mmol) obtained in Step 4 and N,N-dimethylaniline (0.1 mL) was refluxed in phosphorus oxychloride (60 mL) for 15 hours. After the reaction mixture was diluted with dichloromethane, ice water was added thereto, and the resulting mixture was extracted. After the organic layer was dried over anhydrous magnesium sulfate, the solvent was evaporated under reduced pressure, whereby the crude title Compound R11 (1.7 g) was obtained. This compound was used in the subsequent reaction without particularly performing further purification.

Reference Example 12

3-{[1-(6,7-Dimethoxyquinazolin-4-yl)piperidin-4-yl]methyl}-3,4-dihydroquinazolin-2(1H)-one (Compound 53)

The title Compound 53 was synthesized according to the method described in Chemical & Pharmaceutical Bulletin 1990, 38(6), 1591.

Example 1

2-[(3-{[1-(6,7-Dimethoxyquinazolin-4-yl)piperidin-4-yl]methyl}-2-oxo-3,4-dihydroquinazolin-1(2H)-yl) methyl]benzamide (Compound 1)

Step 1: 3-{[1-(6,7-Dimethoxyquinazolin-4-yl)piperidin-4-yl]methyl}-3,4-dihydroquinazolin-2(1H)-one (300 mg, 0.69 mmol) obtained by the method described in Chemical & Pharmaceutical Bulletin 1990, 38(6), 1591 was dissolved in DMF (3.0 mL), and sodium hydride (about 60 wt %, 33 mg) and methyl 2-(bromomethyl)-benzoate (190 mg, 0.83 mmol) were sequentially added thereto in an ice bath. After the resulting mixture was stirred at room temperature for 2 hours, a saturated aqueous sodium bicarbonate solution was added to the reaction mixture, and the resulting mixture was extracted with ethyl acetate. The organic layer was washed with saturated brine, and then dried over anhydrous magnesium sulfate and concentrated under reduced pressure. The resulting residue was purified by silica gel column chromatography (a chloroform/methanol mixed solvent), whereby methyl 2-[(3-{[1-(6,7-dimethoxyquinazolin-4-yl)piperidin-4-yl]methyl}-2-oxo-3,4-dihydroquinazolin-1 (2H)-yl)methyl]benzoate (355 mg, yield: 88%) was obtained.

ESI-MS m/z: 582 (M+H)$^+$, $^1$H-NMR (400 MHz, CDCl$_3$, δ): 8.66 (s, 1H), 8.04 (d, J=7.8 Hz, 1H), 7.41-7.36 (m, 1H), 7.32-7.27 (m, 2H), 7.15-7.06 (m, 4H), 6.99-6.94 (m, 1H), 6.57 (d, J=8.8 Hz, 1H), 5.52 (s, 2H), 4.57 (s, 2H), 4.22-4.15 (br m, 2H), 4.02 (s, 3H), 3.97 (s, 3H), 3.93 (s, 3H), 3.50 (d, J=7.8 Hz, 2H), 3.12-3.02 (m, 2H), 2.18-2.08 (m, 1H), 1.96-1.87 (br m, 2H), 1.66-1.55 (br m, 2H)

Step 2: Methyl 2-[3-{[1-(6,7-dimethoxyquinazolin-4-yl) piperidin-4-yl]methyl}-2-oxo-3,4-dihydroquinazolin-1 (2H)-yl)methyl]benzoate (100 mg, 0.17 mmol) obtained in Step 1 and lithium hydroxide monohydrate (12 mg, 0.52 mmol) were stirred in an ethanol (0.50 mL)/water (0.50 mL) mixed solvent at room temperature for 2 hours. To the reaction mixture, 3.0 mol/L hydrochloric acid was added under ice cooling, and the deposited solid was collected by filtration and dried under reduced pressure, whereby 2-[(3-{[1-(6,7-dimethoxyquinazolin-4-yl)piperidin-4-yl]methyl}-2-oxo-3,4-dihydroquinazolin-1(2H)-yl)methyl]benzoic acid (90 mg, yield: 92%) was obtained.

$^1$H-NMR (400 MHz, DMSO-$d_6$, δ): 13.16 (br s, 1H), 8.70 (s, 1H), 7.96 (d, J=6.8 Hz, 1H), 7.47-7.42 (m, 1H), 7.36-7.32 (m, 1H), 7.30-7.18 (m, 3H), 7.13-7.08 (m, 1H), 7.02-6.94 (m, 2H), 6.51 (d, J=7.8 Hz, 1H), 5.38 (s, 2H), 4.70-4.50 (m, 4H), 3.97 (s, 3H), 3.92 (s, 3H), 3.48-3.36 (m, 4H), 2.26-2.19 (m, 1H), 1.92-1.84 (m, 2H), 1.49-1.39 (m, 2H)

Step 3: 2-[(3-{[1-(6,7-Dimethoxyquinazolin-4-yl)piperidin-4-yl]methyl}-2-oxo-3,4-dihydroquinazolin-1(2H)-yl) methyl]benzoic acid (40 mg, 0.07 mmol) obtained in Step 2, EDC hydrochloride (20 mg, 0.11 mmol), HOBt.H$_2$O (16 mg, 0.11 mmol) and an aqueous ammonia solution (about 28%, 0.04 mL) were stirred in DMF (1.0 mL) at room temperature for 3 hours. To the reaction mixture, a saturated aqueous sodium bicarbonate solution was added, and the resulting mixture was extracted with ethyl acetate. The organic layer was washed with saturated brine, and then dried over anhydrous magnesium sulfate and concentrated under reduced pressure. The resulting residue was purified by silica gel column chromatography (a chloroform/methanol mixed solvent), whereby the title Compound 1 (35 mg, yield: 88%) was obtained.

ESI-MS m/z: 567 (M+H)$^+$, $^1$H-NMR (300 MHz, CDCl$_3$, δ): 8.65 (s, 1H), 7.58-7.53 (m, 1H), 7.33-7.28 (m, 1H), 7.28-7.24 (m, 2H), 7.23 (s, 1H), 7.20-7.16 (m, 1H), 7.11-7.09 (m, 1H), 7.07 (s, 1H), 7.01-6.97 (m, 1H), 6.84 (d, J=7.7 Hz, 1H), 6.65 (br s, 1H), 5.72 (br s, 1H), 5.34 (s, 2H), 4.53 (s, 2H), 4.21-4.11 (br m, 2H), 4.02 (s, 3H), 3.97 (s, 3H), 3.45 (d, J=7.3 Hz, 2H), 3.11-3.00 (m, 2H), 2.13-2.04 (m, 1H), 1.90-1.85 (m, 2H), 1.55-1.50 (m, 2H)

Example 2

3-{[1-(6,7-Dimethoxyquinazolin-4-yl)piperidin-4-yl]methyl}-1-[(tetrahydrofuran-2-yl)methyl]-3,4-dihydroquinazolin-2(1H)-one (Compound 2)

The title Compound 2 (95 mg, yield: 40%) was obtained in the same manner as in Example 1 using 2-(bromomethyl)tetrahydrofuran.

ESI-MS m/z: 518 (M+H)$^+$, $^1$H-NMR (300 MHz, CDCl$_3$, δ): 8.64 (s, 1H), 7.26-7.23 (m, 2H), 7.12-6.95 (m, 4H), 4.50 (d, J=14 Hz, 1H), 4.35 (d, J=14 Hz, 1H), 4.26-4.11 (m, 5H), 4.02 (s, 3H), 3.98 (s, 3H), 3.95-3.84 (m, 2H), 3.79-3.71 (m, 1H), 3.51-3.34 (m, 1H), 3.09-2.98 (m, 2H), 2.10-1.50 (m, 9H)

Example 3

2-[(3-{[1-([1,3]Dioxo[4,5-g]quinazolin-8-yl)piperidin-4-yl]methyl}-2-oxo-3,4-dihydroquinazolin-1(2H)-yl)methyl]benzo nitrile (Compound 3)

[1,3]Dioxo[4,5-g]quinazolin-8(7H)-one (24 mg, 0.13 mmol) obtained by the method described in Journal of Medicinal Chemistry, 2010, 53, 8089, BOP (84 mg, 0.19 mmol) and DBU (58 mg, 0.38 mmol) were stirred in DMF (1.0 mL) at room temperature for 1 hour. Thereafter, Compound R2 (50 mg, 0.18 mmol) obtained in Reference Example 2 was added thereto, and the resulting mixture was stirred at 80° C. for 2 hours. To the reaction mixture, a saturated aqueous sodium bicarbonate solution was added, and the resulting mixture was extracted with ethyl acetate. The organic layer was washed with saturated brine, and then dried over anhydrous magnesium sulfate and concentrated under reduced pressure. The resulting residue was purified by silica gel column chromatography (a chloroform/methanol mixed solvent), whereby the title Compound 3 (26 mg, yield: 39%) was obtained.

ESI-MS m/z: 533 (M+H)$^+$, $^1$H-NMR (400 MHz, CDCl$_3$, δ): 8.63 (s, 1H), 7.69 (d, J=6.8 Hz, 1H), 7.52-7.47 (m, 1H), 7.36-7.32 (m, 1H), 7.26-7.23 (m, 1H), 7.20 (s, 1H), 7.16-7.10 (m, 3H), 7.01-6.97 (m, 1H), 6.57 (d, J=7.8 Hz, 1H), 6.11 (s, 2H), 5.36 (s, 2H), 4.57 (s, 2H), 4.14-4.09 (br m, 2H), 3.50 (d, J=6.8 Hz, 2H), 3.06-2.99 (m, 2H), 2.14-2.07 (m, 1H), 1.94-1.88 (m, 2H), 1.65-1.61 (m, 2H)

Example 4

2-[(3-{[1-(Benzo[d][1,2,3]triazin-4-yl)piperidin-4-yl]methyl}-2-oxo-3,4-dihydroquinazolin-1(2H)-yl)methyl]benzonitrile (Compound 4)

The title Compound 4 (18 mg, yield: 29%) was obtained in the same manner as in Example 3 using Compound R2 and benzo[d][1,2,3]triazin-4(3H)-one.

ESI-MS m/z: 490 (M+H)$^+$, $^1$H-NMR (300 MHz, CDCl$_3$, δ): 8.26 (d, J=8.1 Hz, 1H), 7.94-7.87 (m, 2H), 7.77-7.67 (m, 2H), 7.54-7.47 (m, 1H), 7.37-7.24 (m, 2H), 7.16-7.10 (m, 2H), 7.02-6.96 (m, 1H), 6.58 (d, J=8.1 Hz, 1H), 5.35 (s, 2H), 4.57-4.54 (m, 4H), 3.50 (d, J=7.3 Hz, 2H), 3.34-3.23 (m, 2H), 2.25-2.18 (m, 1H), 2.02-1.94 (m, 2H), 1.72-1.59 (m, 2H)

Example 5

2-[(3-{[1-(6,7-Dimethoxyquinazolin-4-yl)piperidin-4-yl]methyl}-6-(methylsulfonyl)-2-oxo-3,4-dihydroquinazolin-1(2H)-yl)methyl]benzonitrile (Compound 5)

Step 1: To a THF solution (10.0 mL) of 5-(methylsulfanyl)-2-nitrobenzoic acid (800 mg, 3.75 mmol), a borane-dimethyl sulfide complex (1.14 g, 15.0 mmol) was added at room temperature, and the resulting mixture was refluxed for 1.5 hours. The reaction mixture was cooled to 0° C., and hydrochloric acid (1.00 mol/L, 10.0 mL) was added thereto, and the resulting mixture was extracted with ethyl acetate. The organic layer was washed with saturated brine, and then dried over anhydrous magnesium sulfate. A residue obtained by evaporating the solvent under reduced pressure was dissolved in chloroform (20.0 mL) and DMF (1.00 mL), and manganese dioxide (6.00 g, 69.0 mmol) was added thereto, and the resulting mixture was stirred overnight at room temperature. The reaction mixture was treated with diatomaceous earth, and the solvent was evaporated under reduced pressure, thereby obtaining crude 5-(methylthio)-2-nitrobenzaldehyde. By using this crude compound, tert-butyl 4-{[6-(methylthio)-2-oxo-1,2-dihydroquinazolin-3(4H)-yl]methyl}piperidine-1-carboxylate (850 mg, yield: 58%) was obtained in the same manner as in Reference Example 1.

ESI-MS m/z: 392 (M+H)$^+$

Step 2: Tert-butyl 4-{[6-(methylthio)-2-oxo-1,2-dihydroquinazolin-3(4H)-yl]methyl}piperidine-1-carboxylate (400 mg, 1.02 mmol) obtained in Step 1 was dissolved in dichloromethane (10.0 mL), and a saturated aqueous sodium bicarbonate solution (10.0 mL) and meta-chloroperoxybenzoic acid (about 70 wt %, 630 mg) were sequentially added thereto in an ice bath, and the resulting mixture was stirred at room temperature for 2 hours. To the reaction mixture, a saturated aqueous sodium bicarbonate solution was added, and the organic layer was separated and the aqueous layer was extracted with chloroform. The organic layers were combined and washed with saturated brine, and then dried over anhydrous magnesium sulfate. The solvent was evaporated under reduced pressure, and the resulting residue was purified by silica gel column chromatography (a chloroform/methanol mixed solvent), whereby tert-butyl 4-{[6-(methylsulfonyl)-2-oxo-1,2-dihydroquinazolin-3(4H)-yl]methyl}piperidine-1-carboxylate (433 mg, quantitative yield) was obtained.

ESI-MS m/z: 424 (M+H)$^+$

Step 3: Tert-butyl 4-{[6-(methylsulfonyl)-2-oxo-1,2-dihydroquinazolin-3(4H)-yl]methyl}piperidine-1-carboxylate (200 mg, 0.47 mmol) obtained in Step 2 was dissolved in ethyl acetate (3.0 mL), and a hydrochloric acid-ethyl acetate solution (4.0 mol/L, 3.5 mL) was added thereto in an ice bath. After the resulting mixture was stirred at room temperature for 2 hours, the solvent was evaporated under reduced pressure. To the resulting residue, 4-chloro-6,7-dimethoxyquinazoline (117 mg, 0.52 mmol) and diisopropylethylamine (183 mg, 1.4 mmol) were added, and the resulting mixture was refluxed in 2-propanol (5.0 mL) for 2 hours. To the reaction mixture, a saturated aqueous sodium bicarbonate solution was added, and the resulting mixture was extracted with chloroform. The organic layer was washed with saturated brine and dried over anhydrous magnesium sulfate, and then, the solvent was concentrated under reduced pressure. The resulting residue was purified by silica gel column chromatography (a chloroform/methanol mixed solvent), whereby 3-{[1-(6,7-dimethoxyquinazolin-4-yl)piperidin-4-yl]methyl}-6-(methylsulfonyl)-3,4-dihydroquinazolin-2 (1H)-one (116 mg, yield: 48%) was obtained.

ESI-MS m/z: 512 (M+H)$^+$

Step 4: The title Compound 5 (23 mg, yield: 24%) was obtained in the same manner as in Example 1 using 3-{[1-(6,7-dimethoxyquinazolin-4-yl)piperidin-4-yl]methyl}-6-(methylsulfonyl)-3,4-dihydroquinazolin-2(1H)-one obtained in Step 3.

ESI-MS m/z: 627 (M+H)$^+$, $^1$H-NMR (300 MHz, CDCl$_3$, δ): 8.66 (s, 1H), 7.72-7.69 (m, 3H), 7.55-7.50 (m, 1H), 7.41-7.36 (m, 1H), 7.26-7.22 (m, 2H), 7.09 (s, 1H), 6.73-6.70 (m, 1H), 5.39 (s, 2H), 4.62 (s, 2H), 4.25-4.20 (m, 2H), 4.03 (s, 3H), 3.99 (s, 3H), 3.52 (d, J=7.2 Hz, 2H), 3.15-3.07 (m, 2H), 3.03 (s, 3H), 2.24-2.11 (m, 1H), 1.94-1.90 (m, 2H), 1.66-1.55 (m, 2H)

Example 6

3-(3-{[1-(6,7-Dimethoxyquinazolin-4-yl)piperidin-4-yl]methyl}-2-oxo-3,4-dihydroquinazolin-1(2H)-yl) benzonitrile (Compound 6)

Step 1: 3-{[1-(6,7-dimethoxyquinazolin-4-yl)piperidin-4-yl]methyl}-3,4-dihydroquinazolin-2(1H)-one (50 mg, 0.12 mmol) obtained by the method described in Chemical & Pharmaceutical Bulletin 1990, 38(6), 1591, copper(I) iodide (22 mg, 0.12 mmol), trans-1,2-cyclohexanediamine (13 mg, 0.12 mmol), 3-iodobenzonitrile (53 mg, 0.23 mmol) and tripotassium phosphate (49 mg, 0.23 mmol) were stirred in 1,4-dioxane (1.0 mL) at 100° C. for 5 hours. To the reaction mixture, a saturated aqueous sodium bicarbonate solution was added, and the resulting mixture was extracted with ethyl acetate. The organic layer was treated with diatomaceous earth and concentrated under reduced pressure. The resulting residue was purified by silica gel column chromatography (a chloroform/methanol mixed solvent), whereby the title Compound 6 (51 mg, yield: 82%) was obtained.

ESI-MS m/z: 535 (M+H)$^+$, $^1$H-NMR (300 MHz, CDCl$_3$, δ): 8.66 (s, 1H), 7.73-7.59 (m, 4H), 7.24 (s, 1H), 7.16-7.00 (m, 4H), 6.17 (d, J=8.4 Hz, 1H), 4.62 (s, 2H), 4.24-4.14 (br m, 2H), 4.02 (s, 3H), 3.98 (s, 3H), 3.47 (d, J=7.3 Hz, 2H), 3.10-3.06 (br m, 2H), 2.18-2.10 (m, 1H), 1.93-1.90 (m, 2H), 1.62-1.54 (m, 2H)

Example 7

5-(3-{[1-(6,7-Dimethoxyquinazolin-4-yl)piperidin-4-yl]methyl}-2-oxo-3,4-dihydroquinazolin-1(2H)-yl)-2-fluorobenzonitrile (Compound 7)

The title Compound 7 (40 mg, yield: 63%) was obtained in the same manner as in Example 6 using 2-fluoro-5-iodobenzonitrile.

ESI-MS m/z: 553 (M+H)$^+$, $^1$H-NMR (300 MHz, CDCl$_3$, δ): 8.67 (s, 1H), 7.66-7.57 (m, 2H), 7.39-7.31 (m, 1H), 7.24 (s, 1H), 7.16-7.01 (m, 4H), 6.19 (d, J=8.4 Hz, 1H), 4.61 (s, 2H), 4.21-4.17 (m, 2H), 4.02 (s, 3H), 3.98 (s, 3H), 3.46 (d, J=7.0 Hz, 2H), 3.12-3.05 (m, 2H), 2.14-2.09 (m, 1H), 1.93-1.89 (m, 2H), 1.65-1.52 (m, 2H)

Example 8

3-{[1-(6,7-Dimethoxyquinazolin-4-yl)piperidin-4-yl]methyl}-1-(3-nitrophenyl)-3,4-dihydroquinazolin-2 (1H)-one (Compound 8)

The title Compound 8 (40 mg, yield: 63%) was obtained in the same manner as in Example 6 using 1-iodo-3-nitrobenzene.

ESI-MS m/z: 555 (M+H)$^+$, $^1$H-NMR (300 MHz, CDCl$_3$, δ): 8.67 (s, 1H), 8.32-8.27 (m, 1H), 8.26-8.23 (m, 1H), 7.74-7.66 (m, 2H), 7.26-7.24 (m, 1H), 7.17-7.01 (m, 4H), 6.20 (d, J=8.1 Hz, 1H), 4.63 (s, 2H), 4.24-4.15 (m, 2H), 4.02 (s, 3H), 3.98 (s, 3H), 3.48 (d, J=7.0 Hz, 2H), 3.15-3.03 (m, 2H), 2.20-2.08 (m, 1H), 1.97-1.88 (m, 2H), 1.66-1.49 (m, 2H)

Example 9

4-(3-{[1-(6,7-Dimethoxyquinazolin-4-yl)piperidin-4-yl]methyl}-2-oxo-3,4-dihydroquinazolin-1(2H)-yl) picolinonitrile (Compound 9)

The title Compound 9 (29 mg, yield: 47%) was obtained in the same manner as in Example 6 using 4-iodopicolinonitrile.

ESI-MS m/z: 536 (M+H)$^+$, $^1$H-NMR (300 MHz, CDCl$_3$, δ): 8.80 (d, J=5.2 Hz, 1H), 8.66 (s, 1H), 7.84 (d, J=1.9 Hz, 1H), 7.66 (dd, J=5.2, 1.9 Hz, 1H), 7.24-7.07 (m, 5H), 6.39 (d, J=8.1 Hz, 1H), 4.59 (s, 2H), 4.23-4.15 (br m, 2H), 4.02 (s, 3H), 3.99 (d, J=3.3 Hz, 3H), 3.47 (d, J=7.0 Hz, 2H), 3.13-3.03 (m, 2H), 2.19-2.05 (m, 1H), 1.94-1.85 (m, 2H), 1.66-1.49 (m, 2H)

Example 10

2-(3-{[1-(6,7-Dimethoxyquinazolin-4-yl)piperidin-4-yl]methyl}-2-oxo-3,4-dihydroquinazolin-1(2H)-yl) isonicotinonitrile (Compound 10)

The title Compound 10 (580 mg, yield: 94%) was obtained in the same manner as in Example 6 using 2-iodoisonicotinonitrile.

ESI-MS m/z: 536 (M+H)$^+$, $^1$H-NMR (400 MHz, CDCl$_3$, δ): 8.78 (d, J=4.9 Hz, 1H), 8.66 (s, 1H), 7.86 (s, 1H), 7.55 (d, J=4.9 Hz, 1H), 7.25 (s, 1H), 7.17-7.03 (m, 4H), 6.27 (d, J=7.8 Hz, 1H), 4.62 (s, 2H), 4.24-4.14 (m, 2H), 4.02 (s, 3H), 3.98 (s, 3H), 3.48 (d, J=7.8 Hz, 2H), 3.12-3.03 (m, 2H), 2.20-2.08 (m, 1H), 1.97-1.85 (m, 2H), 1.67-1.52 (m, 2H)

Example 11

4-(3-{[1-(6,7-Dimethoxyquinazolin-4-yl)piperidin-4-yl]methyl}-2-oxo-3,4-dihydroquinazolin-1(2H)-yl) pyrimidine-2-carbonitrile (Compound 11)

Step 1: The title Compound 11 (8.0 mg, yield: 13%) was obtained in the same manner as in Example 6 using 3-{[1-(6,7-dimethoxyquinazolin-4-yl)piperidin-4-yl]methyl}-3,4-dihydroquinazolin-2(1H)-one obtained by the method described in Chemical & Pharmaceutical Bulletin 1990, 38 (6), 1591 and 4-bromopyrimidine-2-carbonitrile.

ESI-MS m/z: 537 (M+H)$^+$, $^1$H-NMR (400 MHz, CDCl$_3$, δ): 8.77 (d, J=5.9 Hz, 1H), 8.66 (s, 1H), 8.19 (d, J=5.9 Hz,

1H), 7.31-7.21 (m, 4H), 7.14 (d, J=7.8 Hz, 1H), 7.07 (s, 1H), 4.49 (s, 2H), 4.22-4.14 (m, 2H), 4.02 (s, 3H), 3.98 (s, 3H), 3.50 (d, J=7.8 Hz, 2H), 3.12-3.01 (m, 2H), 2.13-2.03 (m, 1H), 1.89-1.79 (m, 2H), 1.64-1.52 (m, 2H)

Example 12

5-(3-{[1-(6,7-Dimethoxyquinazolin-4-yl)piperidin-4-yl]methyl}-2-oxo-3,4-dihydroquinazolin-1(2H)-yl)-2-oxo-1,2-dihydropyridine-3-carbonitrile (Compound 12)

Step 1: 5-(3-{[1-(6,7-Dimethoxyquinazolin-4-yl)piperidin-4-yl]methyl}-2-oxo-3,4-dihydroquinazolin-1(2H)-yl)-2-oxo-1-{[2-(trimethylsilyl)ethoxy]methyl}1,2-dihydropyridine-3-carbonitrile (80 mg, yield: 51%) was obtained in the same manner as in Example 6 using Compound R3 obtained in Reference Example 3.
ESI-MS m/z: 682 (M+H)$^+$ Step 2: 5-(3-{[1-(6,7-Dimethoxyquinazolin-4-yl)piperidin-4-yl]methyl}-2-oxo-3,4-dihydroquinazolin-1(2H)-yl)-2-oxo-1-{[2-(trimethylsilyl)ethoxy]methyl}1,2-dihydropyridine-3-carbonitrile (80 mg, 0.12 mmol) obtained in Step 1 and trifluoroacetic acid (740 mg, 6.5 mmol) were stirred in dichloromethane (1.0 mL) for 5 hours under ice cooling. To the reaction mixture, a saturated aqueous sodium bicarbonate solution was added, and the resulting mixture was extracted with chloroform. The organic layer was washed with saturated brine, and then dried over anhydrous magnesium sulfate and concentrated under reduced pressure. The resulting residue was purified by silica gel column chromatography (a methanol/chloroform mixed solvent), whereby the title Compound 12 (20 mg, yield: 31%) was obtained.
ESI-MS m/z: 552 (M+H)$^+$, $^1$H-NMR (300 MHz, CDCl$_3$, δ): 8.66 (s, 1H), 7.93 (d, J=2.7 Hz, 1H), 7.79 (d, J=2.7 Hz, 1H), 7.25 (s, 1H), 7.21-7.14 (m, 2H), 7.10-7.04 (m, 2H), 6.44 (d, J=8.1 Hz, 1H), 4.58 (s, 2H), 4.24-4.16 (m, 2H), 4.02 (s, 3H), 3.99 (s, 3H), 3.46 (d, J=7.3 Hz, 2H), 3.15-3.04 (m, 2H), 2.18-2.09 (m, 1H), 1.94-1.85 (m, 2H), 1.66-1.51 (m, 2H)

Example 13

3-(3-{[1-(6,7-Dimethoxyquinazolin-4-yl)piperidin-4-yl]methyl}-2-oxo-3,4-dihydroquinazolin-1(2H)-yl)benzenesulfonamide (Compound 13)

Step 1: Tert-butyl 3-(3-{[1-(6,7-dimethoxyquinazolin-4-yl)piperidin-4-yl]methyl}-2-oxo-3,4-dihydroquinazolin-1(2H)-yl)phenylsulfonyl{[2-(trimethylsilyl)ethoxy]methyl}carbamate (98 mg, yield: 86%) was obtained in the same manner as in Example 6 using Compound R4 obtained in Reference Example 4.
ESI-MS m/z: 820 (M+H)$^+$, $^1$H-NMR (300 MHz, CDCl$_3$, δ): 8.66 (s, 1H), 8.08-8.04 (m, 1H), 7.99-7.97 (m, 1H), 7.66-7.62 (m, 2H), 7.24 (s, 1H), 7.14-6.99 (m, 4H), 6.18-6.14 (m, 1H), 5.28 (s, 2H), 4.59 (s, 2H), 4.21-4.11 (m, 2H), 4.02 (s, 3H), 3.98 (s, 3H), 3.61-3.55 (m, 2H), 3.46 (d, J=7.0 Hz, 2H), 3.13-3.03 (m, 2H), 2.16-2.06 (m, 1H), 1.95-1.87 (m, 2H), 1.65-1.53 (m, 2H), 1.37-1.28 (m, 9H), 0.90-0.85 (m, 2H), −0.03 (s, 9H)

Step 2: The title Compound 13 (25 mg, yield: 37%) was obtained in the same manner as in Step 2 of Example 12 using tert-butyl 3-(3-{[1-(6,7-dimethoxyquinazolin-4-yl)piperidin-4-yl]methyl}-2-oxo-3,4-dihydroquinazolin-1(2H)-yl)phenylsulfonyl{[2-(trimethylsilyl)ethoxy]methyl}carbamate obtained in Step 1.
ESI-MS m/z: 589 (M+H)$^+$, $^1$H-NMR (300 MHz, CDCl$_3$, δ): 8.64 (s, 1H), 7.96-7.90 (m, 2H), 7.65-7.59 (m, 1H), 7.56-7.52 (m, 1H), 7.24 (s, 1H), 7.14-6.97 (m, 4H), 6.20-6.15 (m, 1H), 5.16 (br s, 2H), 4.61 (s, 2H), 4.22-4.13 (m, 2H), 4.01 (s, 3H), 3.97 (s, 3H), 3.45 (d, J=7.3 Hz, 2H), 3.13-3.03 (m, 2H), 2.18-2.07 (m, 1H), 1.94-1.85 (m, 2H), 1.64-1.49 (m, 2H)

Example 14

4-(3-{[1-(6,7-Dimethoxyquinazolin-4-yl)piperidin-4-yl]methyl}-2-oxo-3,4-dihydroquinazolin-1(2H)-yl)picolinamide (Compound 14)

Step 1: Ethyl 4-(3-{[1-(6,7-dimethoxyquinazolin-4-yl)piperidin-4-yl]methyl}-2-oxo-3,4-dihydroquinazolin-1(2H)-yl)picolinate (235 mg, yield: 70%) was obtained in the same manner as in Example 6 using ethyl 4-iodopicolinate.
ESI-MS m/z: 555 (M+H)$^+$, $^1$H-NMR (300 MHz, CDCl$_3$, δ): 8.89 (d, J=5.1 Hz, 1H), 8.67 (s, 1H), 8.17 (s, 1H), 7.59 (d, J=5.1 Hz, 1H), 7.28-7.03 (m, 5H), 6.31 (d, J=8.1 Hz, 1H), 4.61 (s, 2H), 4.49 (q, J=7.1 Hz, 2H), 4.25-4.14 (m, 2H), 4.02 (s, 3H), 3.98 (s, 3H), 3.48 (d, J=7.3 Hz, 2H), 3.14-3.01 (m, 2H), 2.20-2.06 (m, 1H), 1.97-1.85 (m, 2H), 1.63-1.55 (m, 2H), 1.44 (t, J=7.1 Hz, 3H)

Step 2: The title Compound 14 (40 mg, yield: 80%) was obtained in the same manner as in Example 1 using ethyl 4-(3-{[1-(6,7-dimethoxyquinazolin-4-yl)piperidin-4-yl]methyl}-2-oxo-3,4-dihydroquinazolin-1(2H)-yl)picolinate obtained in Step 1.
ESI-MS m/z: 554 (M+H)$^+$, $^1$H-NMR (300 MHz, CDCl$_3$, δ): 8.71 (d, J=5.1 Hz, 1H), 8.66 (s, 1H), 8.19 (d, J=2.0 Hz, 1H), 7.86 (br s, 1H), 7.62 (dd, J=5.1, 2.0 Hz, 1H), 7.23 (s, 1H), 7.17-7.01 (m, 4H), 6.32 (d, J=8.1 Hz, 1H), 5.71 (br s, 1H), 4.59 (s, 2H), 4.23-4.14 (m, 2H), 4.02 (s, 3H), 3.99 (s, 3H), 3.47 (d, J=7.3 Hz, 2H), 3.15-3.04 (m, 2H), 2.19-2.06 (m, 1H), 1.96-1.85 (m, 2H), 1.66-1.51 (m, 2H)

Example 15

2-Cyano-4-(3-{[1-(6,7-dimethoxyquinazolin-4-yl)piperidin-4-yl]methyl}-2-oxo-3,4-dihydroquinazolin-1(2H)-yl)benzoic acid (Compound 15)

Step 1: 2-Bromo-5-(3-{[1-(6,7-dimethoxyquinazolin-4-yl)piperidin-4-yl]methyl}-2-oxo-3,4-dihydroquinazolin-1(2H)-yl)benzonitrile (630 mg, yield: 89%) was obtained in the same manner as in Example 6 using 2-bromo-5-iodobenzonitrile.
ESI-MS m/z: 613 (M+H)$^+$, $^1$H-NMR (300 MHz, CDCl$_3$, δ): 8.66 (s, 1H), 7.81 (d, J=8.4 Hz, 1H), 7.68 (d, J=2.6 Hz, 1H), 7.47 (dd, J=8.4, 2.6 Hz, 1H), 7.23 (s, 1H), 7.16-7.04 (m, 4H), 6.22 (d, J=8.1 Hz, 1H), 4.60 (s, 2H), 4.21-4.16 (m, 2H), 4.02 (s, 3H), 3.98 (s, 3H), 3.46 (d, J=7.0 Hz, 2H), 3.13-3.03 (m, 2H), 2.17-2.07 (m, 1H), 1.94-1.87 (m, 2H), 1.61-1.54 (m, 2H)

Step 2: 2-Bromo-5-(3-{[1-(6,7-dimethoxyquinazolin-4-yl)piperidin-4-yl]methyl}-2-oxo-3,4-dihydroquinazolin-1(2H)-yl)benzonitrile (200 mg, 0.33 mmol) obtained in Step 1, palladium acetate (7.3 mg, 0.03 mmol), 1,3-bis(diphenylphosphino)propane (DPPP) (130 mg, 0.03 mmol), potassium carbonate (90 mg, 0.65 mmol) and 1-propanol (3.0 mL) were stirred in DMF (1.0 mL) under a carbon monoxide atmosphere (atmospheric pressure) at 80° C. for 4 hours. To the reaction mixture, a saturated aqueous sodium bicarbonate solution was added, and the resulting mixture was treated with diatomaceous earth, and then, the filtrate was extracted with ethyl acetate. The organic layer was washed with saturated brine, and then dried over anhydrous magnesium sulfate and concentrated under reduced pressure. The resulting residue was purified by silica gel column chromatography (an ethyl acetate/heptane mixed solvent), whereby propyl 2-cyano-4-(3-{[1-(6,7-dimethoxyquinazolin-4-yl)piperidin-4-yl]methyl}-2-oxo-3,4-dihydroquinazolin-1(2H)-yl)benzoate (175 mg, yield: 86%) was obtained.

ESI-MS m/z: 621 (M+H)$^+$, $^1$H-NMR (300 MHz, CDCl$_3$, δ): 8.65 (s, 1H), 8.28-8.25 (m, 1H), 7.84-7.82 (m, 1H), 7.73-7.69 (m, 1H), 7.23 (s, 1H), 7.18-7.02 (m, 4H), 6.23-6.20 (m, 1H), 4.61 (s, 2H), 4.41 (t, J=6.6 Hz, 2H), 4.22-4.15 (m, 2H), 4.02 (s, 3H), 3.98 (s, 3H), 3.49-3.44 (m, 2H), 3.13-3.03 (m, 2H), 2.18-2.08 (m, 1H), 1.94-1.83 (m, 2H), 1.64-1.53 (m, 2H), 1.28-1.24 (m, 2H), 1.07 (t, J=7.5 Hz, 3H)

Step 3: The title Compound 15 (24 mg, yield: 16%) was obtained in the same manner as in Step 2 of Example 1 using propyl 2-cyano-4-(3-{[1-(6,7-dimethoxyquinazolin-4-yl)piperidin-4-yl]methyl}-2-oxo-3,4-dihydroquinazolin-1 (2H)-yl)benzoate obtained in Step 2.

ESI-MS m/z: 579 (M+H)$^+$, $^1$H-NMR (300 MHz, DMSO-d$_6$, δ): 8.59 (s, 1H), 8.30 (s, 1H), 8.20 (d, J=8.1 Hz, 1H), 8.01 (d, J=1.8 Hz, 1H), 7.77 (dd, J=8.4, 2.2 Hz, 1H), 7.28-7.15 (m, 3H), 7.13-6.98 (m, 2H), 6.16 (d, J=8.1 Hz, 1H), 4.62 (s, 2H), 4.41-4.30 (m, 2H), 3.94 (s, 3H), 3.89 (s, 3H), 3.40-3.19 (m, 4H), 2.16-2.13 (m, 1H), 1.86-1.82 (m, 2H), 1.43-1.39 (m, 2H)

Example 16

3-{[1-(6,7-Dimethoxyquinazolin-4-yl)piperidin-4-yl]methyl}-1-(tetrahydro-2H-pyran-4-yl)-3,4-dihydroquinazolin-2(1H)-one (Compound 16)

Step 1: Tert-butyl 4-[(2-aminobenzylamino)methyl]-piperidine-1-carboxylate (1.0 g, 3.1 mmol) obtained in Step 2 of Reference Example 1 was dissolved in methanol (50 mL), and in an ice bath, tetrahydro-4H-pyran-4-one (627 mg, 6.3 mmol) and sodium borohydride (481 mg, 12 mmol) were added thereto, and the resulting mixture was stirred for 2 hours, and thereafter further stirred at room temperature for 2 hours. The reaction mixture was diluted with water, and then extracted with ethyl acetate. The organic layer was washed with saturated brine and dried over anhydrous magnesium sulfate. A residue obtained by evaporating the solvent under reduced pressure was purified by silica gel column chromatography (a chloroform/methanol mixed solvent), whereby crude tert-butyl 4-{[2-(tetrahydro-2H-pyran-4-ylamino)benzylamide]methyl}piperidine-1-carboxylate was obtained. This compound was dissolved in dioxane (50 mL), and 1,1'-carbonyldiimidazole (0.4 g, 2.5 mmol) was added thereto, and the resulting mixture was stirred at 100° C. for 2 days. To the reaction mixture, water was added, and the resulting mixture was extracted with ethyl acetate. Then, the organic layer was washed with saturated brine and dried over anhydrous magnesium sulfate. After the solvent was evaporated under reduced pressure, the resulting residue was purified by preparative reverse-phase HPLC (an acetonitrile/water mixed solvent), whereby tert-butyl 4-{[2-oxo-1-(tetrahydro-2H-pyran-4-yl)-1,2-dihydroquinazolin-3(4H)-yl]methyl}piperidine-1-carboxylate (50 mg, yield: 4%) was obtained.

ESI-MS m/z: 430 (M+H)$^+$

Step 2: The title Compound 16 (10 mg, yield: 8%) was obtained in the same manner as in Step 3 of Example 5 using tert-butyl 4-{[2-oxo-1-(tetrahydro-2H-pyran-4-yl)-1,2-dihydroquinazolin-3(4H)-yl]methyl}piperidine-1-carboxylate obtained in Step 1.

ESI-MS m/z: 518 (M+H)$^+$, $^1$H-NMR (300 MHz, CDCl$_3$, δ): 8.65 (s, 1H), 7.36-7.26 (m, 2H), 7.19-7.06 (m, 4H), 4.29 (s, 2H), 4.28-4.17 (m, 3H), 4.17-4.07 (m, 2H), 4.03 (s, 3H), 3.90 (s, 3H), 3.60-3.45 (m, 2H), 3.40 (d, J=7.2 Hz, 2H), 3.16-3.05 (m, 2H), 2.86-2.72 (m, 2H), 2.17-1.96 (m, 1H), 1.93-1.72 (m, 4H), 1.65-1.42 (m, 2H)

Example 17

4-(3-{[1-(6,7-Dimethoxyquinazolin-4-yl)azetidin-3-yl]methyl}-2-oxo-3,4-dihydroquinazolin-1(2H)-yl)picolinonitrile (Compound 17)

The title Compound 17 (12 mg, yield: 13%) was obtained in the same manner as in Step 3 of Example 5 after performing a treatment according to Reference Example 1 using 2-nitrobenzaldehyde and tert-butyl 3-(aminomethyl)azetidine-1-carboxylate.

ESI-MS m/z: 508 (M+H)$^+$, $^1$H-NMR (400 MHz, CDCl$_3$, δ): 8.81 (d, J=4.8 Hz, 1H), 8.51 (s, 1H), 7.81-7.80 (m, 1H), 7.64-7.63 (m, 1H), 7.23-7.09 (m, 5H), 6.37 (d, J=8.0 Hz, 1H), 4.68-4.61 (s, 4H), 4.36-4.32 (m, 2H), 4.01 (s, 3H), 3.94 (s, 3H), 3.84 (d, J=8.0 Hz, 2H), 3.32-3.23 (m, 1H)

Example 18

4-(3-{[1-(6,7-Dimethoxyquinazolin-4-yl)-4-hydroxypiperidin-4-yl]methyl}-2-oxo-3,4-dihydroquinazolin-1(2H)-yl)picolinonitrile (Compound 18)

Step 1: Tert-butyl 4-(aminomethyl)-4-hydroxypiperidine-1-carboxylate (3.1 g, 13 mmol) obtained by the method described in WO2005/000837 was dissolved in methanol (150 mL), and 2-nitrobenzaldehyde (2.0 g, 13 mmol) and sodium cyanoborohydride (1.3 g, 26 mmol) were added thereto, and the resulting mixture was stirred at room temperature for 12 hours. After the reaction mixture was concentrated under reduced pressure, water was added thereto, and the resulting mixture was extracted with ethyl acetate. The organic layer was washed with saturated brine, and then dried over anhydrous magnesium sulfate. A residue obtained by evaporating the solvent under reduced pressure was purified by silica gel column chromatography (a hexane/ethyl acetate mixed solvent), whereby tert-butyl 4-hydroxy-4-[(2-nitrobenzylamino)methyl]piperidine-1-carboxylate (2.2 g, yield: 40%) was obtained.

$^1$H-NMR (400 MHz, CDCl$_3$, δ): 7.97 (dd, J=8.0, 0.8 Hz, 1H), 7.64-7.45 (m, 3H), 5.32 (s, 1H), 4.10 (s, 2H), 3.86 (br s, 2H), 3.18 (t, J=12 Hz, 2H), 2.59 (s, 2H), 1.55-1.40 (m, 13H)

Step 2: The title Compound 18 (14 mg, yield: 17%) was obtained by performing the same treatments as in Reference Example 1, Step 3 of Example 5 and Example 6 sequentially using tert-butyl 4-hydroxy-4-[(2-nitrobenzylamino)methyl]piperidine-1-carboxylate obtained in Step 1.

ESI-MS m/z: 552 (M+H)$^+$, $^1$H-NMR (400 MHz, DMSO-d$_6$, δ): 8.89 (s, 1H), 8.53 (s, 1H), 8.22 (d, J=7.6 Hz, 1H), 7.42-7.34 (m, 4H), 7.22 (s, 1H), 7.10 (s, 1H), 7.06 (d, J=3.2 Hz, 1H), 6.80 (dd, J=7.6, 3.2 Hz, 1H), 4.39 (s, 2H), 3.92 (s, 3H), 3.90 (s, 3H), 3.77-3.72 (m, 2H), 3.51-3.49 (m, 2H), 3.26 (s, 2H), 1.89 (br s, 4H)

Example 19

4-{3-[1-(6,7-Dimethoxyquinazolin-4-yl)piperidin-4-ylamino]-2-oxo-3,4-dihydroquinolin-1(2H)-yl}picolinonitrile (Compound 19)

Step 1: 3-Amino-3,4-dihydroquinolin-2(1H)-one hydrochloride (490 mg, 2.5 mmol) obtained by the method described in WO2004/98589, tert-butyl 4-oxopiperidine-1-carboxylate (590 mg, 3.0 mmol), triacetoxy sodium borohydride (1.6 g, 7.4 mmol), triethylamine (300 mg, 3.0 mmol) and acetic acid (0.1 mL) were stirred overnight in 1,2-dichloroethane (20 mL) at room temperature. To the reaction mixture, a saturated aqueous sodium bicarbonate solution was added, and the organic layer was treated with diatomaceous earth. After the solvent was evaporated under reduced pressure, the resulting residue was purified by silica gel column chromatography (a chloroform/methanol mixed solvent), whereby tert-butyl 4-(2-oxo-1,2,3,4-tetrahydroquinolin-3-ylamino)piperidine-1-carboxylate (626 mg, yield: 74%) was obtained.

ESI-MS m/z: 346 (M+H)$^+$

Step 2: Tert-butyl 4-(2-oxo-1,2,3,4-tetrahydroquinolin-3-ylamino)piperidine-1-carboxylate (0.64 g, 1.9 mmol) obtained in Step 1 and diisopropylethylamine (599 mg, 4.6 mmol) were dissolved in tetrahydrofuran (7.0 mL), and trifluoroacetic anhydride (778 mg, 3.7 mmol) was added thereto at 0° C. After the resulting mixture was stirred at room temperature for 30 minutes, a saturated aqueous sodium bicarbonate solution was added to the reaction mixture, and the resulting mixture was extracted with ethyl acetate. The organic layer was washed with saturated brine, and then dried over anhydrous magnesium sulfate, and the solvent was concentrated under reduced pressure. The resulting residue was purified by silica gel column chromatography (a chloroform/methanol mixed solvent), whereby tert-butyl 4-[2,2,2-trifluoro-N-(2-oxo-1,2,3,4-tetrahydroquinolin-3-yl)acetamide]piperidine-1-carboxylate (644 mg, yield: 79%) was obtained.

ESI-MS m/z: 442 (M+H)$^+$

Step 3: N-[1-(6,7-dimethoxyquinazolin-4-yl)piperidin-4-yl]-2,2,2-trifluoro-N-(2-oxo-1,2,3,4-tetrahydroquinolin-3-yl)acetamide (226 mg, yield: 98%) was obtained in the same manner as in Step 3 of Example 5 using tert-butyl 4-[2,2,2-trifluoro-N-(2-oxo-1,2,3,4-tetrahydroquinolin-3-yl)acetamide]piperidine-1-carboxylate (192 mg, 0.43 mmol) obtained in Step 2.

ESI-MS m/z: 530 (M+H)$^+$

Step 4: N-[1-(6,7-dimethoxyquinazolin-4-yl)piperidin-4-yl]-2,2,2-trifluoro-N-(2-oxo-1,2,3,4-tetrahydroquinolin-3-yl)acetamide (226 mg, 0.427 mmol) obtained in Step 3 and lithium hydroxide monohydrate (36 mg, 0.85 mmol) were stirred overnight in a methanol/water mixed solvent (1/1, 4.0 mL) at 60° C. After the reaction mixture was concentrated under reduced pressure, water was added thereto, and the resulting mixture was extracted with ethyl acetate. The organic layer was washed with saturated brine, and then dried over anhydrous magnesium sulfate, and the solvent was evaporated under reduced pressure.

The resulting residue was purified by preparative thin-layer chromatography (a chloroform/methanol mixed solvent), whereby 3-[1-(6,7-dimethoxyquinazolin-4-yl)piperidin-4-ylamino]-3,4-dihydroquinolin-2(1H)-one (132 mg, yield: 71%) was obtained.

ESI-MS m/z: 434 (M+H)$^+$

Step 5: The title Compound 19 (12 mg, yield: 19%) was obtained in the same manner as in Example 6 using 3-[1-(6,7-dimethoxyquinazolin-4-yl)piperidin-4-ylamino]-3,4-dihydroquinolin-2(1H)-one obtained in Step 4 and 4-iodopicolinonitrile.

ESI-MS m/z: 536 (M+H)$^+$, $^1$H-NMR (400 MHz, CDCl$_3$, δ): 8.83 (d, J=6.0 Hz, 1H), 8.67 (s, 1H), 7.70-7.69 (m, 1H), 7.53-7.51 (m, 1H), 7.34-7.32 (m, 1H), 7.27 (s, 1H), 7.21-7.14 (m, 2H), 7.10 (s, 1H), 6.50 (d, J=11 Hz, 1H), 4.17-4.11 (m, 2H), 4.03 (s, 3H), 3.99 (s, 3H), 3.77 (dd, J=13, 6.0 Hz, 1H), 3.22-3.01 (m, 5H), 1.73-1.67 (m, 2H), 1.28-1.24 (m, 2H)

Example 20

3-(3-{[1-(6,7-Dimethoxyquinazolin-4-yl)piperidin-4-yl]methyl}-2,4-dioxo-3,4-dihydroquinazolin-1(2H)-yl)benzonitrile (Compound 20)

Step 1: Isatoic anhydride (5.0 g, 31 mmol) was dissolved in 1,4-dioxane (40 mL), and tert-butyl 4-(aminomethyl)piperidine-1-carboxylate (6.6 g, 31 mmol) and diisopropylethylamine (8.3 g, 64 mmol) were added thereto, and the resulting mixture was stirred at 80° C. for 2 hours. After the reaction mixture was concentrated under reduced pressure, water was added thereto, and the resulting mixture was extracted with ethyl acetate. The organic layer was washed with saturated brine, and then dried over anhydrous magnesium sulfate, and the solvent was evaporated under reduced pressure, whereby tert-butyl 4-[(2-aminobenzamide)methyl]piperidine-1-carboxylate (10.2 g, quantitative yield) was obtained.

$^1$H-NMR (300 MHz, CDCl$_3$, δ): 7.32-7.29 (m, 1H), 7.23-7.17 (m, 1H), 6.69-6.60 (m, 2H), 6.27 (br s, 1H), 5.50 (br s, 2H), 4.15-4.08 (m, 2H), 3.32-3.27 (m, 2H), 2.73-2.64 (m, 2H), 1.76-1.70 (m, 3H), 1.20-1.10 (m, 2H)

Step 2: Tert-butyl 4-[(2-aminobenzamide)methyl]piperidine-1-carboxylate (500 mg, 1.5 mmol) obtained in Step 1 was dissolved in 1,2-dichloroethane (4.0 mL), and diisopropylethylamine (388 mg, 3.0 mmol) and DMAP (9.2 mg, 0.08 mmol) were added thereto. After the resulting mixture was cooled to 0° C., ethyl chloroformate (195 mg, 1.8 mmol) was added thereto, and then, the resulting mixture was stirred at room temperature for 1 hour. To the reaction mixture, a saturated aqueous sodium bicarbonate solution was added, and the resulting mixture was extracted with chloroform. The organic layer was washed with saturated brine and dried over anhydrous magnesium sulfate, and then, the solvent was evaporated under reduced pressure. The resulting residue was purified by silica gel column chromatography (a hexane/ethyl acetate mixed solvent), whereby tert-butyl 4-{[2-(ethoxycarbonylamino)benzamide]methyl}piperidine-1-carboxylate (577 mg, yield: 95%) was obtained.

$^1$H-NMR (300 MHz, CDCl$_3$, δ): 10.4 (br s, 1H), 8.36 (dd, J=8.4, 0.9 Hz, 1H), 7.49-7.40 (m, 2H), 7.04-6.98 (m, 1H), 6.36-6.34 (m, 1H), 4.21 (q, J=7.2 Hz, 2H), 4.17-4.09 (m, 2H), 3.33 (br s, 2H), 2.74-2.66 (m, 2H), 1.75-1.71 (m, 3H), 1.46 (s, 9H), 1.31 (t, J=7.2 Hz, 3H), 1.21-1.11 (m, 2H)

Step 3: Tert-butyl 4-{[2-(ethoxycarbonylamino)benzamide]methyl}piperidine-1-carboxylate (0.47 g, 1.2 mmol) obtained in Step 2 and potassium hydroxide (390 mg, 7.0 mmol) were refluxed in ethanol (12 mL) for 30 minutes. To the reaction mixture, water was added, and the resulting mixture was cooled to 0° C., and then neutralized with dilute hydrochloric acid. Then, the resulting solid was collected by filtration, whereby tert-butyl 4-[(2,4-dioxo-1,2-dihydroquinazolin-3(4H)-yl)methyl]piperidine-1-carboxylate (343 mg, yield: 82%) was obtained.

¹H-NMR (400 MHz, CDCl₃, δ): 9.00 (br s, 1H), 8.13 (d, J=7.6 Hz, 1H), 7.65-7.60 (m, 1H), 7.25-7.23 (m, 1H), 7.06-7.04 (m, 1H), 4.13-4.10 (m, 2H), 4.00 (d, J=6.8 Hz, 2H), 2.70-2.64 (m, 2H), 2.04 (br s, 1H), 1.67-1.62 (m, 2H), 1.45 (s, 9H), 1.39-1.27 (m, 2H)

Step 4: 3-{[1-(6,7-Dimethoxyquinazolin-4-yl)piperidin-4-yl]methyl}quinazoline-2,4(1H,3H)-dione (414 mg, yield: 98%) was obtained in the same manner as in Step 3 of Example 5 using tert-butyl 4-[(2,4-dioxo-1,2-dihydroquinazolin-3(4H)-yl)methyl]piperidine-1-carboxylate obtained in Step 3.

¹H-NMR (400 MHz, CDCl₃, δ): 9.57 (br s, 1H), 8.66 (s, 1H), 8.15 (d, J=7.6 Hz, 1H), 7.65-7.61 (m, 1H), 7.28-7.24 (m, 2H), 7.10-7.09 (m, 2H), 4.20-4.11 (m, 4H), 4.02 (s, 3H), 3.99 (s, 3H), 3.07-3.01 (m, 2H), 2.24 (br s, 1H), 1.91-1.88 (m, 2H), 1.74-1.65 (m, 2H)

Step 5: 3-{[1-(6,7-Dimethoxyquinazolin-4-yl)piperidin-4-yl]methyl}quinazoline-2,4(1H,3H)-dione (30 mg, 0.07 mmol) obtained in Step 4, 3-cyanophenylboronic acid (39 mg, 0.27 mmol), copper(II) acetate (49 mg, 0.27 mmol) and triethylamine (27 mg, 0.27 mmol) were mixed and stirred in dichloromethane (1.5 mL) at room temperature for 5 hours, and thereafter further stirred overnight at 35° C. The reaction mixture was treated with diatomaceous earth, and the solvent was evaporated under reduced pressure. Then, the resulting residue was purified by preparative thin-layer chromatography (a chloroform/methanol mixed solvent), whereby the title Compound 20 (18 mg, yield: 48%) was obtained.

ESI-MS m/z: 549 (M+H)⁺, ¹H-NMR (300 MHz, CDCl₃, δ): 8.64 (s, 1H), 8.29 (dd, J=7.5, 1.5 Hz, 1H), 7.88-7.84 (m, 1H), 7.78-7.73 (m, 1H), 7.70-7.69 (m, 1H), 7.65-7.62 (m, 1H), 7.56-7.50 (m, 1H), 7.34-7.27 (m, 2H), 7.18-7.10 (m, 1H), 6.50 (d, J=8.1 Hz, 1H), 4.23-4.13 (m, 4H), 4.00 (s, 3H), 3.99 (s, 3H), 3.10-3.02 (m, 2H), 2.24 (br s, 1H), 1.92-1.88 (m, 2H), 1.75-1.62 (m, 2H)

Example 21

4-(3-{[1-(6,7-Dimethoxyquinazolin-4-yl)piperidin-4-yl]methyl}-2-oxo-3,4-dihydropyrido[3,4-d]pyrimidin-1(2H)-yl)picolinonitrile (Compound 21)

The title Compound 21 (62 mg, yield: 60%) was obtained by performing the same treatments as in Reference Example 1, Step 3 of Example 5 and Example 6 sequentially using 3-aminoisonicotinaldehyde.

ESI-MS m/z: 537 (M+H)⁺, ¹H-NMR (300 MHz, CDCl₃, δ): 8.85 (d, J=5.4 Hz, 1H), 8.66 (s, 1H), 8.36 (d, J=4.8 Hz, 1H), 7.85-7.84 (m, 1H), 7.76 (s, 1H), 7.65-7.62 (m, 1H), 7.24 (s, 1H), 7.14 (d, J=4.8 Hz, 1H), 7.08 (s, 1H), 4.63 (s, 2H), 4.22-4.18 (m, 2H), 4.02 (s, 3H), 3.98 (s, 3H), 3.48 (d, J=7.5 Hz, 2H), 3.13-3.05 (m, 2H), 2.16-2.08 (m, 1H), 1.90-1.86 (m, 2H), 1.65-1.53 (m, 2H)

Example 22

4-(3-{[1-(6,7-Dimethoxyquinazolin-4-yl)piperidin-4-yl]methyl}-2-oxo-3,4-dihydropyrido[2,3-d]pyrimidin-1(2H)-yl)picolinonitrile (Compound 22)

Step 1: Ethyl (3-formylpyridin-2-yl)carbamate (150 mg, 0.77 mmol) obtained by the method described in US2007/259850 and tert-butyl 4-(aminomethyl)piperidine-1-carboxylate (182 mg, 0.85 mmol) were stirred in methanol (2.0 mL) at 60° C. for 2 hours. After the reaction mixture was cooled to room temperature, sodium borohydride (35 mg, 0.93 mmol) was added thereto, and the resulting mixture was stirred for 40 minutes. Toluene (3.0 mL) and acetic acid (0.5 mL) were added thereto, and the resulting mixture was stirred at 110° C. for 3 hours. To the reaction mixture, water was added, and the resulting mixture was extracted with ethyl acetate. The organic layer was washed with saturated brine and dried over anhydrous magnesium sulfate, and then, the solvent was evaporated under reduced pressure. The resulting residue was purified by silica gel column chromatography (a hexane/ethyl acetate mixed solvent), whereby tert-butyl 4-[(2-oxo-1,2-dihydropyrido[2,3-d]pyrimidin-3(4H)-yl)methyl]piperidine-1-carboxylate (246 mg, yield: 92%) was obtained.

¹H-NMR (400 MHz, DMSO-d₆, δ): 9.58 (s, 1H), 8.07 (d, J=4.0 Hz, 1H), 7.49 (d, J=8.0 Hz, 1H), 6.92-6.89 (m, 1H), 4.44 (s, 2H), 3.93-3.90 (m, 2H), 3.20 (d, J=7.6 Hz, 2H), 2.67 (br s, 2H), 1.89 (br s, 1H), 1.58-1.56 (m, 2H), 1.39-1.37 (m, 11H)

Step 2: The title Compound 22 (45 mg, yield: 61%) was obtained by performing the same treatments as in Step 3 of Example 5 and Example 6 sequentially using tert-butyl 4-[(2-oxo-1,2-dihydropyrido[2,3-d]pyrimidin-3(4H)-yl)methyl]piperidine-1-carboxylate obtained in Step 1.

ESI-MS m/z: 537 (M+H)⁺, ¹H-NMR (400 MHz, CDCl₃, δ): 8.79 (d, J=6.0 Hz, 1H), 8.66 (s, 1H), 8.18-8.11 (m, 1H), 7.76 (d, J=2.0 Hz, 1H), 7.57 (dd, J=6.0, 2.0 Hz, 1H), 7.51-7.49 (m, 1H), 7.24-7.23 (m, 1H), 7.08-7.00 (m, 2H), 4.62 (s, 2H), 4.22-4.19 (m, 2H), 4.02 (s, 3H), 3.95 (s, 3H), 3.49 (d, J=7.6 Hz, 2H), 3.12-3.07 (m, 2H), 2.14 (br s, 1H), 1.92-1.89 (m, 2H), 1.64-1.55 (m, 2H)

Example 23

4-(6-Fluoro-2-oxo-3-{[1-(pyrido[3,4-d]pyrimidin-4-yl)piperidin-4-yl]methyl}-3,4-dihydropyrido[2,3-d]pyrimidin-1(2H)-yl)picolinonitrile (Compound 23)

Step 1: Tert-butyl 4-[(6-fluoro-2-oxo-1,2-dihydropyrido[2,3-d]pyrimidin-3(4H)-yl)methyl]piperidine-1-carboxylate (876 mg, yield: 63%) was obtained in the same manner as in Reference Example 1 using 2-amino-5-fluoronicotinaldehyde.

ESI-MS m/z: 365 (M+H)⁺

Step 2: Tert-butyl 4-{[1-(2-cyanopyridin-4-yl)-6-fluoro-2-oxo-1,2-dihydropyrido[2,3-d]pyrimidin-3(4H)-yl]methyl}piperidine-1-carboxylate (588 mg, quantitative yield) was obtained in the same manner as in Example 6 using tert-butyl 4-[(6-fluoro-2-oxo-1,2-dihydropyrido[2,3-d]pyrimidin-3(4H)-yl)methyl]piperidine-1-carboxylate obtained in Step 1 and 4-iodopicolinonitrile.

ESI-MS m/z: 467 (M+H)⁺

Step 3: The title Compound (34 mg, yield: 17%) was obtained in the same manner as in Step 3 of Example 5 using tert-butyl 4-{[1-(2-cyanopyridin-4-yl)-6-fluoro-2-oxo-1,2-dihydropyrido[2,3-d]pyrimidin-3(4H)-yl]methyl}piperidine-1-carboxylate obtained in Step 2 and 4-chloropyrido[3,4-d]pyrimidine obtained by the method described in US2006/199804.

ESI-MS m/z: 496 (M+H)⁺, ¹H-NMR (300 MHz, CDCl₃, δ): 9.31 (s, 1H), 8.80-8.77 (m, 2H), 8.56 (d, J=5.9 Hz, 1H), 7.98 (d, J=2.7 Hz, 1H), 7.73 (t, J=1.1 Hz, 1H), 7.61 (dd, J=5.9, 0.9 Hz, 1H), 7.55 (dd, J=5.4, 2.3 Hz, 1H), 7.29 (dd, J=7.5, 2.9 Hz, 1H), 4.63 (s, 2H), 4.50 (d, J=14 Hz, 2H), 3.48 (d, J=7.2 Hz, 2H), 3.25-3.18 (m, 2H), 2.25-2.17 (m, 1H), 1.94 (t, J=6.6 Hz, 2H), 1.57 (m, 2H)

Example 24

4-(3-{[1-(6,7-Dimethoxyquinazolin-4-yl)piperidin-4-yl]methyl}-2-oxo-3,4-dihydropteridin-1(2H)-yl)picolinonitrile (Compound 24)

The title Compound 24 (60 mg, yield: 84%) was obtained by performing the same treatments as in Reference Example 1, Step 3 of Example 5 and Example 6 sequentially using 3-aminopyrazine-2-carboxaldehyde.

ESI-MS m/z: 538 (M+H)$^+$, $^1$H-NMR (300 MHz, CDCl$_3$, δ): 8.82 (d, J=5.1 Hz, 1H), 8.66 (s, 1H), 8.24 (d, J=2.4 Hz, 1H), 8.07 (d, J=2.4 Hz, 1H), 7.73 (d, J=2.1 Hz, 1H), 7.55 (dd, J=5.1, 2.1 Hz, 1H), 7.25 (s, 1H), 7.08 (s, 1H), 4.79 (s, 2H), 4.23-4.18 (m, 2H), 4.02 (s, 3H), 3.99 (s, 3H), 3.54 (d, J=7.2 Hz, 2H), 3.13-3.05 (m, 2H), 2.16 (br s, 1H), 1.94-1.90 (m, 2H), 1.68-1.56 (m, 2H)

Example 25

4-(4-{[1-(3-Cyanophenyl)-2-oxo-1,2-dihydroquinazolin-3(4H)-yl]methyl}piperidin-1-yl)quinazoline-7-carboxylic acid (Compound 25)

Step 1: 3-{[1-(7-Bromoquinazolin-4-yl)piperidin-4-yl]methyl}-3,4-dihydroquinazolin-2(1H)-one (9.0 g, yield: 54%) was obtained in the same manner as in Step 3 of Example 5 using Compound R1 obtained in Reference Example 1 and 7-bromo-4-chloroquinazoline.

ESI-MS m/z: 452 (M+H)$^+$

Step 2: 3-(3-{[1-(7-Bromoquinazolin-4-yl)piperidin-4-yl]methyl}-2-oxo-3,4-dihydroquinazolin-1(2H)-yl)benzonitrile (0.6 g, yield: 60%) was obtained in the same manner as in Example 6 using 3-{[1-(7-bromoquinazolin-4-yl)piperidin-4-yl]methyl}-3,4-dihydroquinazolin-2(1H)-one obtained in Step 1 and 3-iodobenzonitrile.

ESI-MS m/z: 553 (M+H)$^+$

Step 3: Propyl 4-(4-{[1-(3-cyanophenyl)-2-oxo-1,2-dihydroquinazolin-3(4H)-yl]methyl}piperidin-1-yl)quinazoline-7-carboxylate (1.6 g, yield: 50%) was obtained in the same manner as in Step 2 of Example 15 using 3-(3-{[1-(7-bromoquinazolin-4-yl)piperidin-4-yl]methyl}-2-oxo-3,4-dihydroquinazolin-1(2H)-yl)benzonitrile obtained in Step 2.

ESI-MS m/z: 561 (M+H)$^+$

Step 4: The title Compound 25 (1.0 g, yield: 68%) was obtained in the same manner as in Step 2 of Example 1 using propyl 4-(4-{[1-(3-cyanophenyl)-2-oxo-1,2-dihydroquinazolin-3(4H)-yl]methyl}piperidin-1-yl)quinazoline-7-carboxylate obtained in Step 3.

ESI-MS m/z: 519 (M+H)$^+$, $^1$H-NMR (400 MHz, CDCl$_3$, δ): 9.03 (s, 1H), 8.91 (s, 1H), 8.23 (d, J=6.0 Hz, 1H), 7.87 (d, J=6.6 Hz, 1H), 7.80-7.62 (m, 4H), 7.21-7.09 (m, 2H), 7.09-6.99 (m, 1H), 6.21 (d, J=6.0 Hz, 1H), 4.65 (s, 2H), 4.63 (d, J=10 Hz, 2H), 3.49 (d, J=1.6 Hz, 2H), 3.37-3.27 (m, 2H), 2.39-2.13 (m, 1H), 2.08-1.91 (m, 2H), 1.81-1.61 (m, 2H)

Example 26

4-(4-{[1-(3-Cyanophenyl)-2-oxo-1,2-dihydroquinazolin-3(4H)-yl]methyl}piperidin-1-yl)-N-methylquinazoline-7-carboxamido (Compound 26)

The title Compound 26 (36 mg, yield: 23%) was obtained in the same manner as in Step 3 of Example 1 using Compound 25 obtained in Example 25 and methylamine.

ESI-MS m/z: 532 (M+H)$^+$, $^1$H-NMR (300 MHz, CDCl$_3$, δ): 8.73 (s, 1H), 8.15 (s, 1H), 7.93 (s, 2H), 7.79-7.62 (m, 4H), 7.17-7.01 (m, 3H), 6.41 (br s, 1H), 6.19 (d, J=4.5 Hz, 1H), 4.63 (s, 2H), 4.47 (d, J=13 Hz, 2H), 3.48 (d, J=7.2 Hz, 2H), 3.26-3.11 (m, 2H), 3.09 (d, J=4.8 Hz, 3H), 2.25-2.07 (m, 1H), 2.04-1.85 (m, 2H), 1.68-1.41 (m, 2H)

Example 27

4-[3-({1-[7-(4-Methylpiperazine-1-carbonyl)quinazolin-4-yl]piperidin-4-yl}methyl)-2-oxo-3,4-dihydroquinazolin-1(2H)-yl]picolinonitrile (Compound 27)

Step 1: Tert-butyl 4-{[1-(2-cyanopyridin-4-yl)-2-oxo-1,2-dihydroquinazolin-3(4H)-yl]methyl}piperidine-1-carboxylate (578 mg, yield: 74%) was obtained in the same manner as in Example 6 using tert-butyl 4-(2-oxo-1,4-dihydro-2H-quinazolin-3-ylmethyl)piperidine-1-carboxylate obtained in Step 3 of Reference Example 1 and 4-iodopicolinonitrile.

ESI-MS m/z: 448 (M+H)$^+$

Step 2: 4-[2-Oxo-3-(piperidin-4-ylmethyl)-3,4-dihydroquinazolin-1(2H)-yl]picolinonitrile dihydrochloride (94 mg, quantitative yield) was obtained in the same manner as in Step 4 of Reference Example 1 using tert-butyl 4-{[1-(2-cyanopyridin-4-yl)-2-oxo-1,2-dihydroquinazolin-3(4H)-yl]methyl}piperidine-1-carboxylate obtained in Step 1.

ESI-MS m/z: 348 (M+H)$^+$

Step 3: Tert-butyl 4-(4-{[1-(2-cyanopyridin-4-yl)-2-oxo-1,2-dihydroquinazolin-3(4H)-yl]methyl}piperidin-1-yl)quinazoline-7-carboxylate (22 mg, yield: 6.4%) was obtained in the same manner as in Example 3 using 4-[2-oxo-3-(piperidin-4-ylmethyl)-3,4-dihydroquinazolin-1 (2H)-yl]picolinonitrile dihydrochloride obtained in Step 2 and Compound R5 obtained in Reference Example 5.

ESI-MS m/z: 576 (M+H)$^+$, $^1$H-NMR (300 MHz, CDCl$_3$, δ): 8.80 (d, J=5.1 Hz, 1H), 8.75 (s, 1H), 8.49 (d, J=1.8 Hz, 1H), 7.98 (dd, J=8.6, 1.6 Hz, 1H), 7.87 (d, J=8.8 Hz, 1H), 7.84 (d, J=1.8 Hz, 1H), 7.66 (dd, J=5.3, 2.0 Hz, 1H), 7.14 (dq, J=5.3, 18 Hz, 3H), 6.38 (d, J=8.4 Hz, 1H), 4.59 (s, 2H), 4.39 (d, J=13 Hz, 2H), 3.47 (d, J=7.3 Hz, 2H), 3.15 (t, J=12 Hz, 2H), 2.16 (dt, J=4.6, 14 Hz, 1H), 1.91 (d, J=11 Hz, 2H), 1.68-1.51 (m, 11H)

Step 4: After tert-butyl 4-(4-{[1-(2-cyanopyridin-4-yl)-2-oxo-1,2-dihydroquinazolin-3(4H)-yl]methyl}piperidin-1-yl)quinazoline-7-carboxylate (22 mg, 0.038 mmol) obtained in Step 3 was stirred in a trifluoroacetic acid (0.18 mL)/dichloromethane (0.20 mL) mixed solvent at room temperature for 1.5 hours, the solvent was evaporated under reduced pressure. By using the resulting residue and 1-methylpiperazine, the title Compound 27 (7.4 mg, yield: 32%) was obtained in the same manner as in Step 3 of Example 1.

ESI-MS m/z: 602 (M+H)$^+$, $^1$H-NMR (300 MHz, CDCl$_3$, δ): 8.81 (d, J=5.0 Hz, 1H), 8.73 (s, 1H), 7.90 (d, J=8.6 Hz, 1H), 7.84 (d, J=1.4 Hz, 2H), 7.65 (dd, J=5.2, 2.0 Hz, 1H), 7.47 (dd, J=8.6, 1.4 Hz, 1H), 7.20-7.09 (m, 3H), 6.38 (d, J=8.2 Hz, 1H), 4.60 (s, 2H), 4.39 (d, J=13 Hz, 2H), 3.86 (br s, 2H), 3.92-3.76 (m, 4H), 3.15 (t, J=12 Hz, 2H), 2.54 (br s, 2H), 2.43-2.30 (m, 5H), 2.21-2.11 (m, 1H), 1.91 (d, J=11.3 Hz, 2H), 1.58 (dd, J=21, 12 Hz, 2H)

Example 28

4-(4-{[1-(2-Cyanopyridin-4-yl)-2-oxo-1,2-dihydroquinazolin-3(4H)-yl]methyl}piperidin-1-yl)quinazoline-7-carboxamido (Compound 28)

The title Compound 28 (19 mg, yield: 43%) was obtained in the same manner as in Step 4 of Example 27 using tert-butyl 4-(4-{[1-(2-cyanopyridin-4-yl)-2-oxo-1,2-dihydroquinazolin-3(4H)-yl]methyl}piperidin-1-yl)quinazoline-7-carboxylate obtained in Step 3 of Example 27 and ammonium chloride.

ESI-MS m/z: 519 (M+H)$^+$, $^1$H-NMR (400 MHz, DMSO-d$_6$, δ): 8.88 (d, J=5.6 Hz, 1H), 8.64 (s, 1H), 8.29 (d, J=1.6 Hz, 2H), 8.20 (d, J=1.6 Hz, 1H), 8.02-8.00 (m, 1H), 7.94-7.91 (m, 1H), 7.82 (dd, J=5.2, 2.0 Hz, 1H), 7.64 (s, 1H), 7.30 (d, J=7.6 Hz, 1H), 7.15-7.06 (m, 2H), 6.36 (d, J=7.2 Hz, 1H), 4.64 (s, 2H), 4.35-4.32 (m, 2H), 3.39-3.33 (m, 2H), 3.21-3.15 (m, 2H), 2.16 (br s, 1H), 1.83-1.80 (m, 2H), 1.48-1.43 (m, 2H)

Example 29

4-(4-{[1-(3-Cyanophenyl)-2-oxo-1,2-dihydroquinazolin-3(4H)-yl]methyl}piperidin-1-yl)pyrido[3,4-d]pyrimidine-7-oxide (Compound 29)

Step 1: 3-{[1-(Pyrido[3,4-d]pyrimidin-4-yl)piperidin-4-yl]methyl}-3,4-dihydroquinazolin-2(1H)-one (83 mg, yield: 48%) was obtained in the same manner as in Example 3 using Compound R1 and 4-hydroxypyrido[3,4-d]pyrimidine.

ESI-MS m/z: 375 (M+H)$^+$

Step 2: 3-{[1-(Pyrido[3,4-d]pyrimidin-4-yl)piperidin-4-yl]methyl}-3,4-dihydroquinazolin-2(1H)-one (598 mg, 1.6 mmol) obtained in Step 1 was dissolved in dichloromethane (10 mL), and meta-chloroperoxybenzoic acid (about 70 wt %, 394 mg) was added thereto, and the resulting mixture was stirred at 0° C. for 1 hour. To the reaction mixture, a saturated aqueous sodium bicarbonate solution was added, and the resulting mixture was extracted with chloroform. The organic layer was washed with saturated brine, and then dried over anhydrous magnesium sulfate and concentrated under reduced pressure. The resulting residue was purified by preparative reverse-phase HPLC (an acetonitrile/water mixed solvent), whereby 4-{4-[(2-oxo-1,2-dihydroquinazolin-3(4H)-yl)methyl]piperidin-1-yl}pyrido[3,4-d]pyrimidine-7-oxide (133 mg, yield: 21%) was obtained.

ESI-MS m/z: 391 (M+H)$^+$

Step 3: The title Compound 29 (32 mg, yield: 21%) was obtained in the same manner as in Example 6 using 4-{4-[(2-oxo-1,2-dihydroquinazolin-3(4H)-yl)methyl]piperidin-1-yl}pyrido[3,4-d]pyrimidine-7-oxide obtained in Step 2.

ESI-MS m/z: 492 (M+H)$^+$, $^1$H-NMR (300 MHz, CDCl$_3$, δ): 8.70 (d, J=1.8 Hz, 1H), 8.66 (s, 1H), 8.08-8.05 (m, 1H), 7.66-7.59 (m, 5H), 7.15-7.00 (m, 3H), 6.18 (d, J=8.1 Hz, 1H), 4.61 (s, 2H), 4.43-4.39 (m, 2H), 3.46 (d, J=7.5 Hz, 2H), 3.26-3.19 (m, 2H), 2.25-2.18 (m, 1H), 1.97-1.94 (m, 2H), 1.64-1.47 (m, 2H)

Example 30

4-(3-{[1-(Imidazo[1,2-a]pyrazin-8-yl)piperidin-4-yl]methyl}-2-oxo-3,4-dihydroquinazolin-1(2H)-yl)picolinonitrile (Compound 30)

The title Compound 30 (12 mg, yield: 19%) was obtained in the same manner as in Example 5 using 4-[2-oxo-3-(piperidin-4-ylmethyl)-3,4-dihydroquinazolin-1(2H)-yl]picolinonitrile dihydrochloride obtained in Step 2 of Example 27 and 8-chloroimidazo[1,2-a]pyrazine.

ESI-MS m/z: 465 (M+H)$^+$, $^1$H-NMR (300 MHz, CDCl$_3$, δ): 8.80-8.78 (m, 1H), 7.84-7.83 (m, 1H), 7.67-7.65 (m, 1H), 7.53 (d, J=1.5 Hz, 1H), 7.48-7.47 (m, 2H), 7.33 (d, J=4.8 Hz, 1H), 7.19-7.07 (m, 3H), 6.40-6.36 (m, 1H), 5.48-5.43 (m, 2H), 4.56 (s, 2H), 3.39 (d, J=6.9 Hz, 2H), 3.10-3.00 (m, 2H), 2.17-2.10 (m, 1H), 1.88-1.85 (m, 2H), 1.52-1.38 (m, 2H)

Example 31

4-(3-{[1-(7H-pyrrolo[2,3-d]pyrimidin-4-yl)piperidin-4-yl]methyl}-2-oxo-3,4-dihydroquinazolin-1(2H)-yl)picolinonitrile (Compound 31)

Step 1: 4-(2-Oxo-3-{[1-(7-{[2-(trimethylsilyl)ethoxy]methyl}-7H-pyrrolo[2,3-d]pyrimidin-4-yl)piperidin-4-yl]methyl}-3,4-dihydroquinazolin-1(2H)-yl)picolinonitrile (63 mg, yield: 67%) was obtained in the same manner as in Example 5 using 4-[2-oxo-3-(piperidin-4-ylmethyl)-3,4-dihydroquinazolin-1(2H)-yl]picolinonitrile dihydrochloride obtained in Step 2 of Example 27 and 4-chloro-7-{[2-(trimethylsilyl)ethoxy]methyl}-7H-pyrrolo[2,3-d]pyrimidine obtained by the method described in Organic Letters 2009, 11, 1999.

$^1$H-NMR (300 MHz, CDCl$_3$, δ): 8.86-8.84 (m, 1H), 8.40 (s, 1H), 7.89 (dd, J=2.4, 0.9 Hz, 1H), 7.71 (dd, J=5.4, 2.4 Hz, 1H), 7.25-7.13 (m, 4H), 6.57 (d, J=3.6 Hz, 1H), 6.45-6.42 (m, 1H), 5.63 (s, 2H), 4.86-4.82 (m, 2H), 4.62 (s, 2H), 3.61-3.55 (m, 2H), 3.45 (d, J=6.9 Hz, 2H), 3.20-3.11 (m, 2H), 2.30-2.17 (m, 1H), 1.94-1.91 (m, 2H), 1.54-1.41 (m, 2H), 0.99-0.91 (m, 2H), −0.05 (s, 9H)

Step 2: The title Compound 31 (25 mg, yield: 64%) was obtained in the same manner as in Step 2 of Example 12 using 4-(2-oxo-3-{[1-(7-{[2-(trimethylsilyl)ethoxy]methyl}-7H-pyrrolo[2,3-d]pyrimidin-4-yl)piperidin-4-yl]methyl}-3,4-dihydroquinazolin-1(2H)-yl)picolinonitrile obtained in Step 1.

ESI-MS m/z: 465 (M+H)$^+$, $^1$H-NMR (300 MHz, CDCl$_3$, δ): 10.0 (br s, 1H), 8.80 (d, J=5.7 Hz, 1H), 8.32 (s, 1H), 7.84-7.83 (m, 1H), 7.67-7.64 (m, 1H), 7.19-7.05 (m, 4H), 6.50 (d, J=3.3 Hz, 1H), 6.40-6.37 (m, 1H), 4.84-4.79 (m, 2H), 4.57 (s, 2H), 3.40 (d, J=6.9 Hz, 2H), 3.16-3.08 (m, 2H), 2.25-2.12 (m, 1H), 1.90-1.86 (m, 2H), 1.49-1.36 (m, 2H)

Example 32

4-(3-{[1-(5-Methoxypyrimidin-4-yl)piperidin-4-yl]methyl}-2-oxo-3,4-dihydroquinazolin-1(2H)-yl)picolinonitrile (Compound 32)

Step 1: 3-{[1-(6-Chloro-5-methoxypyrimidin-4-yl)piperidin-4-yl]methyl}-3,4-dihydroquinazolin-2(1H)-one (504 mg, yield: 73%) was obtained in the same manner as in Example 5 using 4-[2-oxo-3-(piperidin-4-ylmethyl)-3,4-dihydroquinazolin-1(2H)-yl]picolinonitrile dihydrochloride obtained in Step 2 of Example 27 and 4,6-dichloro-5-methoxypyrimidine.

ESI-MS m/z: 388 (M+H)$^+$

Step 2: 3-{[1-(6-Chloro-5-methoxypyrimidin-4-yl)piperidin-4-yl]methyl}-3,4-dihydroquinazolin-2(1H)-one (100 mg, 0.26 mmol) obtained in Step 1, palladium-carbon (10 wt %, 27 mg) and triethylamine (52 mg, 0.52 mmol) were mixed and stirred in ethyl acetate (3.0 mL) under a hydrogen atmosphere (atmospheric pressure) at room temperature for 3 hours. The reaction mixture was treated with diatomaceous earth, and the solvent was evaporated under reduced pressure. To the resulting residue, diethyl ether was added, and the resulting solid was collected by filtration, whereby 3-{[1-(5-methoxypyrimidin-4-yl)piperidin-4-yl]methyl}-3,4-dihydroquinazolin-2(1H)-one (82 mg, yield: 90%) was obtained.

ESI-MS m/z: 354 (M+H)$^+$

Step 3: The title Compound 32 (72 mg, yield: 86%) was obtained in the same manner as in Example 6 using 3-{[1-(5-methoxypyrimidin-4-yl)piperidin-4-yl]methyl}-3,4-dihydroquinazolin-2(1H)-one obtained in Step 2 and 4-iodopicolinonitrile.

ESI-MS m/z: 456 (M+H)$^+$, $^1$H-NMR (400 MHz, CDCl$_3$, δ): 8.79 (d, J=5.6 Hz, 1H), 8.32 (s, 1H), 7.88-7.83 (m, 2H), 7.66-7.64 (m, 1H), 7.19-7.08 (m, 3H), 6.38 (d, J=7.6 Hz, 1H), 4.59-4.56 (m, 4H), 3.85 (s, 3H), 3.39 (d, J=6.8 Hz, 2H), 2.91-2.85 (m, 2H), 2.09-2.04 (m, 1H), 1.81-1.78 (m, 2H), 1.45-1.31 (m, 2H)

Example 33

4-(3-{[1-(6-Aminopyrimido[3,4-d]pyrimidin-4-yl) piperidin-4-yl]methyl}-2-oxo-3,4-dihydroquinazolin-1(2H)-yl)picolinonitrile (Compound 33)

Step 1: Compound R1 (841 mg, 3.0 mmol), 4,6-dichloropyrido[3,4-d]pyrimidine (716 mg, 3.6 mmol) obtained by the method described in Bioorganic & Medicinal Chemistry Letters, 2001, 11, 1401, and diisopropylethylamine (2.3 g, 18 mmol) were stirred in 2-propanol (8.0 mL) at 100° C. for 6 hours. To the reaction mixture, a saturated aqueous sodium bicarbonate solution was added, and the resulting mixture was extracted with ethyl acetate. The organic layer was washed with saturated brine, and then dried over anhydrous magnesium sulfate and concentrated under reduced pressure. The resulting residue was purified by silica gel column chromatography (a chloroform/methanol mixed solvent), whereby 3-[1-(6-chloropyrimido[3,4-d]pyrimidin-4-yl)piperidin-4-yl methyl]-3,4-dihydroquinazolin-2(1H)-one (600 mg, yield: 49%) was obtained.

ESI-MS m/z: 409 (M+H)$^+$, $^1$H-NMR (300 MHz, CDCl$_3$, δ): 9.09 (s, 1H), 8.73 (s, 1H), 7.66 (s, 1H), 7.58 (br s, 1H), 7.21-7.15 (m, 1H), 7.07-7.02 (m, 1H), 6.98-6.93 (m, 1H), 6.74-6.70 (m, 1H), 4.51 (s, 2H), 4.49-4.41 (m, 2H), 3.44 (d, J=7.7 Hz, 2H), 3.27-3.18 (m, 2H), 2.22-2.11 (m, 1H), 1.98-1.89 (m, 2H), 1.63-1.49 (m, 2H)

Step 2: 4-(3-{[1-(6-Chloropyrimido[3,4-d]pyrimidin-4-yl)piperidin-4-yl]methyl}-2-oxo-3,4-dihydroquinazolin-1(2H)-yl)picolinonitrile (370 mg, yield: 74%) was obtained in the same manner as in Example 6 using 3-[1-(6-chloropyrimido[3,4-d]pyrimidin-4-yl)piperidin-4-yl methyl]-3,4-dihydroquinazolin-2(1H)-one obtained in Step 1 and 4-iodopicolinonitrile.

ESI-MS m/z: 511 (M+H)$^+$, $^1$H-NMR (300 MHz, CDCl$_3$, δ): 9.10 (s, 1H), 8.81 (d, J=5.9 Hz, 1H), 8.74 (s, 1H), 7.84-7.83 (m, 1H), 7.67-7.64 (m, 2H), 7.21-7.09 (m, 3H), 6.41-6.37 (m, 1H), 4.59 (s, 2H), 4.48-4.43 (m, 2H), 3.46 (d, J=7.3 Hz, 2H), 3.27-3.18 (m, 2H), 2.24-2.16 (m, 1H), 1.98-1.90 (m, 2H), 1.61-1.48 (m, 2H)

Step 3: 4-(3-{[1-(6-Chloropyrimido[3,4-d]pyrimidin-4-yl)piperidin-4-yl]methyl}-2-oxo-3,4-dihydroquinazolin-1(2H)-yl)picolinonitrile (300 mg, 0.59 mmol) obtained in Step 2, Tris(dibenzylideneacetone)dipalladium(0) (Pd$_2$dba$_3$) (27 mg, 0.03 mmol), 4,5-bis(diphenylphosphino)-9, 9-dimethylxanthene (Xantphos) (68 mg, 0.12 mmol), cesium carbonate (268 mg, 0.82 mmol) and benzophenone imine (128 mg, 0.71 mmol) were stirred in a 1,4-dioxane (3.0 mL)/toluene (3.0 mL) mixed solvent at 100° C. for 6 hours. To the reaction mixture, a saturated aqueous sodium bicarbonate solution was added, and the resulting mixture was extracted with chloroform. The organic layer was washed with saturated brine, and then dried over anhydrous magnesium sulfate and concentrated under reduced pressure. The resulting residue was purified by silica gel column chromatography (a chloroform/methanol mixed solvent), whereby crude 4-[3-({1-[6-(diphenylmethyleneamino)pyrimido[3,4-d]pyrimidin-4-yl]piperidin-4-yl}methyl)-2-oxo-3,4-dihydroquinazolin-1(2H)-yl]picolinonitrile (44 mg) was obtained.

Step 4: To a THF solution (0.5 mL) of the crude 4-[3-({1-[6-(diphenylmethyleneamino)pyrimido[3,4-d]pyrimidin-4-yl]piperidin-4-yl}methyl)-2-oxo-3,4-dihydroquinazolin-1(2H)-yl]picolinonitrile (40 mg) obtained in Step 3, concentrated hydrochloric acid (12 mol/L, 0.02 mL) was added, and the resulting mixture was stirred at room temperature for 1 hour. To the reaction mixture, a saturated aqueous sodium bicarbonate solution was added, and the resulting mixture was extracted with chloroform. The organic layer was washed with saturated brine, and then dried over anhydrous magnesium sulfate and concentrated under reduced pressure. The resulting residue was purified by preparative thin-layer chromatography (a chloroform/methanol mixed solvent), whereby the title Compound 33 (8.4 mg, yield: 3%) was obtained.

ESI-MS m/z: 492 (M+H)$^+$, $^1$H-NMR (300 MHz, CDCl$_3$, δ): 8.92 (s, 1H), 8.81 (d, J=4.9 Hz, 1H), 8.56 (s, 1H), 7.84 (s, 1H), 7.69-7.62 (m, 1H), 7.23-7.09 (m, 3H), 6.65 (s, 1H), 6.38 (d, J=7.8 Hz, 1H), 4.67-4.56 (m, 4H), 4.36-4.27 (m, 2H), 3.50-3.45 (m, 2H), 3.11-3.01 (m, 2H), 2.19-2.08 (m, 1H), 1.94-1.85 (m, 2H), 1.63-1.50 (m, 2H)

Example 34

4-(2-Oxo-3-{[1-(4-oxo-3,4-dihydropyrido[4,3-d] pyrimidin-5-yl)piperidin-4-yl]methyl}-3,4-dihydroquinazolin-1(2H)-yl)picolinonitrile (Compound 34)

4-[2-Oxo-3-(piperidin-4-ylmethyl)-3,4-dihydroquinazolin-1(2H)-yl]picolinonitrile dihydrochloride (61 mg, 0.15 mmol) obtained in Step 2 of Example 27, 5-chloropyrido[4,3-d]pyrimidin-4(3H)-one (58 mg, 0.32 mmol) obtained by the method described in Synthesis, 2010, 42, 30, and diisopropylethylamine (827 mg, 0.64 mmol) were mixed and stirred in NMP (2.0 mL) at 150° C. for 1 hour using a microwave reactor (manufactured by CEM Corporation) at 300 W. After the solvent was evaporated under reduced pressure, the resulting residue was purified by silica gel column chromatography (a chloroform/methanol mixed solvent), whereby the title Compound 34 (67 mg, yield: 86%) was obtained.

ESI-MS m/z: 493 (M+H)$^+$, $^1$H-NMR (300 MHz, CDCl$_3$, δ): 10.7 (br s, 1H), 8.80 (d, J=5.4 Hz, 1H), 8.33 (d, J=5.1 Hz, 1H), 8.08 (s, 1H), 7.86-7.85 (m, 1H), 7.68 (d, J=2.1, 5.1 Hz, 1H), 7.22-7.07 (m, 3H), 6.96 (d, J=5.1 Hz, 1H), 6.38 (d, J=7.8 Hz, 1H), 4.58 (s, 2H), 4.03-3.99 (m, 2H), 3.45 (d, J=7.2 Hz, 2H), 3.04-2.96 (m, 2H), 2.06 (br s, 1H), 1.84-1.80 (m, 2H), 1.69-1.61 (m, 2H)

Example 35

4-(2-Oxo-3-{[1-(6-oxo-6,7-dihydro-5H-pyrimido[4, 5-b][1,4]oxazin-4-yl)piperidin-4-yl]methyl}-3,4-dihydroquinazolin-1(2H)-yl)picolinonitrile (Compound 35)

The title Compound 35 (21 mg, yield: 19%) was obtained in the same manner as in Example 5 using Compound R6 obtained in Reference Example 6.

ESI-MS m/z: 497 (M+H)$^+$, $^1$H-NMR (300 MHz, CDCl$_3$, δ): 8.81-8.79 (m, 1H), 8.26 (s, 1H), 7.83 (s, 1H), 7.66-7.65 (m, 1H), 7.34 (br s, 1H), 7.20-7.10 (m, 3H), 6.38 (d, J=7.5

Hz, 1H), 4.83 (s, 2H), 4.57 (s, 2H), 3.76-3.72 (m, 2H), 3.44-3.42 (m, 2H), 3.00-2.93 (m, 2H), 2.02 (br s, 1H), 1.89-1.85 (m, 2H), 1.58-1.46 (m, 2H)

Example 36

4-(2-Oxo-1-{[1-(8-oxo-8,9-dihydro-7H-purin-6-yl)piperidin-4-yl]methyl}-3,4-dihydroquinazolin-1(2H)-yl)picolinonitrile (Compound 36)

The title Compound 36 (67 mg, yield: 63%) was obtained in the same manner as in Example 34 using 6-chloro-7H-purin-8 (9H)-one (84 mg, 0.49 mmol) obtained by the method described in WO2007/125315.

ESI-MS m/z: 482 (M+H)$^+$, $^1$H-NMR (300 MHz, DMSO-d$_6$, δ): 11.4 (s, 1H), 10.7 (s, 1H), 8.86 (d, J=5.4 Hz, 1H), 8.18-8.17 (m, 1H), 8.06 (s, 1H), 7.19-7.79 (m, 1H), 7.28 (d, J=6.9 Hz, 1H), 7.17-7.05 (m, 2H), 6.35 (d, J=7.8 Hz, 1H), 4.60 (s, 2H), 4.23-4.19 (d, J=13 Hz, 2H), 3.32-3.30 (m, 2H), 2.93-2.85 (m, 2H), 2.01 (br s, 1H), 1.71-1.67 (m, 2H), 1.24-1.16 (m, 2H)

Example 37

4-(3-{[1-(7-Morpholinoquinazolin-4-yl)piperidin-4-yl]methyl}-2-oxo-3,4-dihydroquinazolin-1(2H)-yl)picolinonitrile (Compound 37)

Step 1: 4-(3-{[1-(7-Bromoquinazolin-4-yl)piperidin-4-yl]methyl}-2-oxo-3,4-dihydroquinazolin-1 (2H)-yl)picolinonitrile (200 mg, yield: 67%) was obtained in the same manner as in Example 5 using 7-bromo-4-chloroquinazoline.

ESI-MS m/z: 554 (M+H)$^+$

Step 2: 4-(3-{[1-(7-Bromoquinazolin-4-yl)piperidin-4-yl]methyl}-2-oxo-3,4-dihydroquinazolin-1(2H)-yl)picolinonitrile (200 mg, 0.36 mmol) obtained in Step 1, morpholine (63 mg, 0.72 mmol), Tris(dibenzylideneacetone)dipalladium (0)-chloroform adduct (Pd$_2$dba$_3$·CHCl$_3$) (37 mg, 0.04 mmol), Xantphos (21 mg, 0.04 mmol) and cesium carbonate (235 mg, 0.72 mmol) were stirred overnight in 1,4-dioxane (10 mL) at 100° C. The reaction mixture was cooled to room temperature, and then diluted with water and extracted with ethyl acetate. The organic layer was washed with saturated brine, and then dried over anhydrous magnesium sulfate, and the solvent was evaporated under reduced pressure. The resulting residue was purified by preparative reverse-phase HPLC (an acetonitrile/water mixed solvent), whereby the title Compound 37 (50 mg, yield: 24%) was obtained.

ESI-MS m/z: 561 (M+H)$^+$, $^1$H-NMR (400 MHz, DMSO-d$_6$, δ): 8.87 (d, J=5.2 Hz, 1H), 8.45 (s, 1H), 8.20 (d, J=1.6 Hz, 1H), 7.83-7.75 (m, 2H), 7.30 (d, J=5.1 Hz, 2H), 7.15-7.08 (m, 2H), 6.99 (d, J=2.4 Hz, 1H), 6.36 (d, J=8.0 Hz, 1H), 4.64 (s, 2H), 4.22-4.19 (m, 2H), 3.77 (t, J=4.8 Hz, 4H), 3.38-3.33 (m, 6H), 3.10-3.04 (m, 2H), 2.08 (br s, 1H), 1.80-1.78 (m, 2H), 1.45-1.37 (m, 2H)

Example 38

4-(2-Oxo-3-{[1-(3-oxo-2,3-dihydro-[1,2,4]triazolo[4,3-a]pyridin-5-yl)piperidin-4-yl]methyl}-3,4-dihydroquinazolin-1(2H)-yl)picolinonitrile (Compound 38)

The title Compound 38 (50 mg, yield: 47%) was obtained in the same manner as in Example 34 using 5-bromo-[1,2,4]triazolo[4,3-a]pyridin-3(2H)-one obtained by the method described in WO2005/85226.

ESI-MS m/z: 481 (M+H)$^+$, $^1$H-NMR (400 MHz, CDCl$_3$, δ): 8.78 (d, J=6.0 Hz, 1H), 7.85-7.83 (m, 2H), 7.64 (dd, J=6.0, 2.0 Hz, 1H), 7.18-7.07 (m, 4H), 6.44 (d, J=8.4 Hz, 1H), 6.36 (d, J=8.0 Hz, 1H), 4.55 (s, 2H), 4.44-4.41 (m, 2H), 3.38-3.36 (m, 2H), 2.96-2.91 (m, 2H), 2.09 (br s, 1H), 1.82-1.79 (m, 2H), 1.34-1.26 (m, 2H)

Example 39

4-(2-Oxo-3-{[1-(3-oxo-2,3-dihydro-[1,2,4]triazolo[4,3-a]pyrazin-8-yl)piperidin-4-yl]methyl}-3,4-dihydroquinazolin-1(2H)-yl)picolinonitrile (Compound 39)

The title Compound 39 (50 mg, yield: 46%) was obtained in the same manner as in Example 34 using Compound R7 obtained in Reference Example 7.

ESI-MS m/z: 482 (M+H)$^+$, $^1$H-NMR (400 MHz, CDCl$_3$, δ): 11.0 (br s, 1H), 8.79 (d, J=5.4 Hz, 1H), 7.83 (d, J=1.8 Hz, 1H), 7.65 (dd, J=5.4, 1.8 Hz, 1H), 7.19-7.08 (m, 5H), 6.38 (d, J=9.8 Hz, 1H), 5.17-5.13 (m, 2H), 4.56 (s, 2H), 3.39 (d, J=7.2 Hz, 2H), 3.06-2.99 (m, 2H), 2.13 (br s, 1H), 1.87-1.83 (m, 2H), 1.46-1.32 (m, 2H)

Example 40

3-(4-{[1-(2-Cyanopyridin-4-yl)-2-oxo-1,2-dihydroquinazolin-3(4H)-yl]methyl}piperidin-1-yl)-2-fluoroisonicotinamide (Compound 40)

The title Compound 40 (50 mg, yield: 46%) was obtained in the same manner as in Example 34 using Compound R8 obtained in Reference Example 8.

ESI-MS m/z: 486 (M+H)$^+$, $^1$H-NMR (270 MHz, CDCl$_3$, δ): 8.79 (d, J=5.1 Hz, 1H), 8.07 (d, J=5.1 Hz, 1H), 7.83 (d, J=1.9 Hz, 1H), 7.65 (dd, J=5.1, 1.9 Hz, 1H), 7.31-7.27 (m, 1H), 7.19-7.07 (m, 3H), 6.49 (br s, 1H), 6.38 (d, J=8.1 Hz, 1H), 5.92 (br s, 1H), 4.57 (s, 2H), 4.05-4.00 (m, 2H), 3.42 (d, J=8.1 Hz, 2H), 2.95-2.87 (m, 2H), 2.03 (br s, 1H), 1.84-1.80 (m, 2H), 1.55-1.50 (m, 2H)

Example 41

4-(3-{[1-(7-Aminopyrido[3,2-d]pyrimidin-4-yl)piperidin-4-yl]methyl}-2-oxo-3,4-dihydroquinazolin-1(2H)-yl)picolinonitrile (Compound 41)

Step 1: 4-(3-{[1-(7-Bromopyrido[3,2-d]pyrimidin-4-yl)piperidin-4-yl]methyl}-2-oxo-3,4-dihydroquinazolin-1(2H)-yl)picolinonitrile (89 mg, yield: 90%) was obtained in the same manner as in Step 1 of Example 37 using 7-bromo-4-chloropyrido[3,2-d]pyrimidine.

ESI-MS m/z: 555 (M+H)$^+$

Step 2: Tert-butyl 4-(4-{[1-(2-cyanopyridin-4-yl)-4-oxo-1,2-dihydroquinazolin-3(4H)-yl]methyl}piperidin-1-yl)pyrido[3,2-d]pyrimidin-7-ylcarbamate (87 mg, yield: 92%) was obtained in the same manner as in Step 3 of Example 33 using 4-(3-{[1-(7-bromopyrido[3,2-d]pyrimidin-4-yl)piperidin-4-yl]methyl}-2-oxo-3,4-dihydroquinazolin-1(2H)-yl)picolinonitrile obtained in Step 1 and tert-butyl carbamate.

ESI-MS m/z: 555 (M+H)$^+$

Step 3: The title Compound 41 (20 mg, yield: 28%) was obtained in the same manner as in Step 4 of Example 33 using tert-butyl 4-(4-{[1-(2-cyanopyridin-4-yl)-4-oxo-1,2-dihydroquinazolin-3(4H)-yl]methyl}piperidin-1-yl)pyrido[3,2-d]pyrimidin-7-ylcarbamate obtained in Step 2.

ESI-MS m/z: 492 (M+H)+, 1H-NMR (300 MHz, CDCl3, δ): 8.79 (d, J=5.4 Hz, 1H), 8.44 (s, 1H), 8.20 (d, J=2.4 Hz, 1H), 7.84 (d, J=1.5 Hz, 1H), 7.65 (dd, J=5.1, 1.8 Hz, 1H), 7.19-7.07 (m, 4H), 6.38 (d, J=7.5 Hz, 1H), 5.62-5.58 (m, 2H), 4.57 (s, 2H), 4.23 (br s, 2H), 3.40 (d, J=6.9 Hz, 2H), 3.17-3.10 (m, 2H), 2.19 (br s, 1H), 1.89-1.84 (m, 2H), 1.52-1.42 (m, 2H)

Example 42

4-(2-Oxo-3-{[1-(4-oxo-3,4-dihydropyrido[3,4-d]pyrimidin-8-yl)piperidin-4-yl]methyl}-3,4-dihydroquinazolin-1(2H)-yl)picolinonitrile (Compound 42)

The title Compound 42 (13 mg, yield: 25%) was obtained in the same manner as in Example 34.
ESI-MS m/z: 493 (M+H)+, 1H-NMR (400 MHz, CDCl3, δ): 11.5 (br s, 1H), 8.79 (d, J=4.8 Hz, 1H), 8.25 (d, J=5.1 Hz, 1H), 8.05 (s, 1H), 7.85 (d, J=1.5 Hz, 1H), 7.65 (dd, J=5.7, 1.8 Hz, 1H), 7.46 (d, J=5.1 Hz, 1H), 7.19-7.07 (m, 3H), 6.38 (d, J=7.5 Hz, 1H), 4.63-4.59 (m, 4H), 3.43 (d, J=7.5 Hz, 2H), 3.04-2.96 (m, 2H), 2.07 (br s, 1H), 1.86-1.82 (m, 2H), 1.70-1.57 (m, 2H)

Example 43

3-(3-{[1-(7,8-Dihydro-5H-pyrano[4,3-d]pyrimidin-4-yl)piperidin-4-yl]methyl}-2-oxo-3,4-dihydroquinazolin-1(2H)-yl)benzonitrile (Compound 43)

Step 1: 3-{[1-(7,8-Dihydro-5H-pyrano[4,3-d]pyrimidin-4-yl)piperidin-4-yl]methyl}-3,4-dihydroquinazolin-2(1H)-one (40 mg, yield: 11%) was obtained in the same manner as in Example 3 using Compound R1 obtained in Reference Example 1 and Compound R10 obtained in Reference Example 10.
ESI-MS m/z: 380 (M+H)+, 1H-NMR (400 MHz, CDCl3, δ): 8.57 (s, 1H), 7.20 (d, J=8.0 Hz, 1H), 7.07 (d, J=8.0 Hz, 1H), 7.00-6.90 (m, 1H), 6.85 (s, 1H), 6.69 (d, J=8.0 Hz, 1H), 4.56 (s, 2H), 4.51 (s, 2H), 4.08 (t, J=6.0 Hz, 2H), 3.79 (d, J=13 Hz, 2H), 3.50 (d, J=7.2 Hz, 2H), 3.00-2.85 (m, 4H), 2.10-1.95 (m, 1H), 1.80-1.70 (m, 2H), 1.50-1.35 (m, 2H)
Step 2: The title Compound 43 (26 mg, yield: 26%) was obtained in the same manner as in Example 6 using 3-{[1-(7,8-dihydro-5H-pyrano[4,3-d]pyrimidin-4-yl)piperidin-4-yl]methyl}-3,4-dihydroquinazolin-2(1H)-one obtained in Step 1 and 3-iodobenzonitrile.
ESI-MS m/z: 481 (M+H)+, 1H-NMR (400 MHz, DMSO-d6, δ): 8.44 (s, 1H), 7.96-7.86 (m, 2H), 7.73 (t, J=7.8 Hz, 1H), 7.70-7.63 (m, 1H), 7.25 (d, J=7.2 Hz, 1H), 7.12-7.06 (m, 1H), 7.05-6.95 (m, 1H), 6.07 (d, J=8.0 Hz, 1H), 4.61 (s, 2H), 4.52 (s, 2H), 3.97 (t, J=6.2 Hz, 2H), 3.76 (d, J=13 Hz, 2H), 3.41-3.20 (m, 2H), 2.88 (t, J=12 Hz, 2H), 2.77 (t, J=6.0 Hz, 2H), 2.11-1.92 (m, 1H), 1.79-1.45 (m, 2H), 1.36-1.19 (m, 2H)

Example 44

5-(3-{[1-(6-Acetyl-5,6,7,8-tetrahydropyrido[4,3-d]pyrimidin-4-yl)piperidin-4-yl]methyl}-2-oxo-3,4-dihydroquinazolin-1(2H)-yl)-2-fluorobenzonitrile (Compound 44)

Step 1: Tert-butyl 4-(4-{[2-oxo-1,2-dihydroquinazolin-3(4H)-yl]methyl}piperidin-1-yl)-7,8-dihydropyrido[4,3-d]pyrimidine-6(5H)-carboxylate (150 mg, yield: 59%) was obtained in the same manner as in Example 3 using Compound R1 obtained in Reference Example 1 and tert-butyl 4-oxo-3,5,7,8-tetrahydro-5H-pyrido[4,3-d]pyrimidine-6-carboxylate obtained by the method described in WO2010/066684.
ESI-MS m/z: 479 (M+H)+, 1H-NMR (300 MHz, CDCl3, δ): 8.57 (s, 1H), 7.20 (t, J=7.5 Hz, 1H), 7.08-6.93 (m, 2H), 6.80 (s, 1H), 6.69 (d, J=8.1 Hz, 1H), 4.51 (s, 2H), 4.44 (s, 2H), 3.89-3.85 (m, 2H), 3.74 (br s, 2H), 3.39-3.34 (m, 2H), 2.95 (br s, 4H), 2.07 (br s, 1H), 1.88-1.84 (m, 2H), 1.50 (br s, 11H)
Step 2: Tert-butyl 4-(4-{[2-oxo-1,2-dihydroquinazolin-3(4H)-yl]methyl}piperidin-1-yl)-7,8-dihydropyrido[4,3-d]pyrimidine-6(5H)-carboxylate (800 mg, 1.7 mmol) obtained in Step 1 was stirred in hydrochloric acid-dioxane (4.0 mol/L, 20 mL) at room temperature for 2 hours. Then, the solvent was evaporated under reduced pressure, whereby crude 3-{[1-(5,6,7,8-tetrahydropyrido[4,3-d]pyrimidin-4-yl)piperidin-4-yl]methyl}-3,4-dihydroquinazolin-2 (1H)-one hydrochloride (600 mg) was obtained. This compound was used in the subsequent reaction without particularly performing further purification.
Step 3: The crude 3-{[1-(5,6,7,8-tetrahydropyrido[4,3-d]pyrimidin-4-yl)piperidin-4-yl]methyl}-3,4-dihydroquinazolin-2 (1H)-one hydrochloride (100 mg) obtained in Step 2, acetyl chloride (25 mg, 0.25 mmol) and triethylamine (40 mg, 0.4 mmol) were stirred in dichloromethane (5.0 mL) at room temperature for 5 hours. To the reaction mixture, water was added, and the resulting mixture was extracted with dichloromethane. The organic layer was washed with saturated brine and dried over anhydrous magnesium sulfate. After the solvent was evaporated under reduced pressure, the resulting residue was purified by preparative reverse-phase HPLC (an acetonitrile/water mixed solvent), whereby 3-{[1-(6-acetyl-5,6,7,8-tetrahydropyrido[4,3-d]pyrimidin-4-yl)piperidin-4-yl]methyl}-3,4-dihydroquinazolin-2(H)-one (20 mg, yield: 19%) was obtained.
ESI-MS m/z: 421 (M+H)+, 1H-NMR (400 MHz, CDCl3, δ): 8.56 (s, 1H), 7.22-7.18 (m, 1H), 7.09-7.07 (m, 1H), 7.02-6.96 (m, 1H), 6.69 (br s, 2H), 4.58 (s, 2H), 4.43 (s, 2H), 3.93-3.86 (m, 2H), 3.80-3.73 (m, 2H), 3.44-3.36 (m, 2H), 2.98-2.93 (m, 4H), 2.19 (s, 3H), 2.08 (br s, 1H), 1.86-1.83 (m, 2H), 1.53-1.44 (m, 2H)
Step 4: The title Compound 44 (44 mg, yield: 34%) was obtained in the same manner as in Example 6 using 3-{[1-(6-acetyl-5,6,7,8-tetrahydropyrido[4,3-d]pyrimidin-4-yl)piperidin-4-yl]methyl}-3,4-dihydroquinazolin-2(1H)-one obtained in Step 3 and 2-fluoro-5-iodobenzonitrile.
ESI-MS m/z: 540 (M+H)+, 1H-NMR (400 MHz, DMSO-d6, δ): 8.46 (s, 1H), 8.03-8.02 (m, 1H), 7.81-7.65 (m, 2H), 7.25 (d, J=7.2 Hz, 1H), 7.10 (t, J=7.6 Hz, 1H), 7.01 (t, J=7.2 Hz, 1H), 6.14 (d, J=8.0 Hz, 1H), 4.70 (s, 2H), 4.62-4.45 (m, 2H), 3.81-3.74 (m, 4H), 3.32 (br s, 2H), 2.93-2.87 (m, 4H), 2.07-2.04 (m, 4H), 1.91-1.84 (m, 2H), 1.38-1.24 (m, 2H)

Example 45

4-(4-{[1-(3-Cyano-4-fluorophenyl)-2-oxo-1,2-dihydroquinazolin-3(4H)-yl]methyl}piperidin-1-yl)pyrido[3,4-d]pyrimidine-6-carboxamido (Compound 45)

Step 1: Tert-butyl 4-{[1-(3-cyano-4-fluorophenyl)-2-oxo-1,2-dihydroquinazolin-3(4H)-yl]methyl}piperidine-1-carboxylate (400 mg, yield: 61%) was obtained in the same manner as in Example 6 using Compound R1 obtained in Reference Example 1 and 2-fluoro-5-iodobenzonitrile.
ESI-MS m/z: 465 (M+H)+

Step 2: 5-(3-{[1-(6-Chloropyrido[3,4-d]pyrimidin-4-yl)piperidin-4-yl]methyl}-2-oxo-3,4-dihydroquinazolin-1(2H)-yl)-2-fluorobenzonitrile (100 mg, yield: 30%) was obtained in the same manner as in Example 3 using tert-butyl 4-{[1-(3-cyano-4-fluorophenyl)-2-oxo-1,2-dihydroquinazolin-3(4H)-yl]methyl}piperidine-1-carboxylate obtained in Step 1 and 6-chloropyrido[3,4-d]pyrimidin-4(3H)-one obtained by the method described in WO2005/16926.

ESI-MS m/z: 528 (M+H)+

Step 3: Propyl 4-(4-{[1-(3-cyano-4-fluorophenyl)-2-oxo-1,2-dihydroquinazolin-3(4H)-yl]methyl}piperidin-1-yl)pyrido[3,4-d]pyrimidine-6-carboxylate (150 mg, yield: 53%) was obtained in the same manner as in Step 2 of Example 15 using 5-(3-{[1-(6-chloropyrido[3,4-d]pyrimidin-4-yl)piperidin-4-yl]methyl}-2-oxo-3,4-dihydroquinazolin-1(2H)-yl)-2-fluorobenzonitrile obtained in Step 2.

Step 4: 4-(4-{[1-(3-Cyano-4-fluorophenyl)-2-oxo-1,2-dihydroquinazolin-3(4H)-yl]methyl}piperidin-1-yl)pyrido[3,4-d]pyrimidine-6-carboxylic acid (1.0 mg, yield: 1%) was obtained in the same manner as in Step 3 of Example 15 using propyl 4-(4-{[1-(3-cyano-4-fluorophenyl)-2-oxo-1,2-dihydroquinazolin-3(4H)-yl]methyl}piperidin-1-yl)pyrido[3,4-d]pyrimidine-6-carboxylate obtained in Step 3.

ESI-MS m/z: 538 (M+H)+

Step 5: 4-(4-{[1-(3-Cyano-4-fluorophenyl)-2-oxo-1,2-dihydroquinazolin-3(4H)-yl]methyl}piperidin-1-yl)pyrido[3,4-d]pyrimidine-6-carboxylic acid (20 mg, 0.04 mmol) obtained in Step 4 was mixed with ammonium chloride (6.0 mg, 0.12 mmol), HATU (21 mg, 0.06 mmol), and diisopropylethylamine (14 mg, 0.12 mmol) in THF (4.0 mL) and the resulting mixture was stirred at room temperature for 15 hours. The reaction mixture was concentrated under reduced pressure, and the resulting residue was purified by preparative reverse-phase HPLC (an acetonitrile/water mixed solvent), whereby the title Compound 45 (11 mg, 54%) was obtained.

ESI-MS m/z: 537 (M+H)+, 1H-NMR (400 MHz, DMSO-$d_6$, δ): 9.15 (s, 1H), 8.73 (s, 1H), 8.46 (s, 1H), 8.26 (s, 1H), 8.04-8.02 (m, 1H), 7.81-7.66 (m, 3H), 7.27 (d, J=7.6 Hz, 1H), 7.13-7.10 (m, 1H), 7.04-7.01 (m, 1H), 6.15 (d, J=8.0 Hz, 1H), 4.65 (s, 2H), 4.50 (d, J=13 Hz, 2H), 3.45-3.20 (m, 4H), 2.20 (br s, 1H), 1.89-1.86 (m, 2H), 1.51-1.29 (m, 2H)

Example 46

4-(4-{[1-(3-Cyano-4-fluorophenyl)-2-oxo-1,2-dihydropyrido[3,2-d]pyrimidin-3(4H)-yl]methyl}piperidin-1-yl)pyrido[3,4-d]pyrimidine-6-carboxamido (Compound 46)

Step 1: Tert-butyl 4-[(2-oxo-1,2-dihydropyrido[3,2-d]pyrimidin-3(4H)-yl)methyl]piperidine-1-carboxylate (2.0 g, yield: 62%) was obtained in the same manner as in Reference Example 1 using 3-aminopicolinaldehyde.

ESI-MS m/z: 347 (M+H)+

Step 2: Tert-butyl 4-{[1-(3-cyano-4-fluorophenyl)-2-oxo-1,2-dihydropyrido[3,2-d]pyrimidin-3(4H)-yl]methyl}piperidine-1-carboxylate (400 mg, yield: 54%) was obtained in the same manner as in Example 6 using tert-butyl 4-[(2-oxo-1,2-dihydropyrido[3,2-d]pyrimidin-3(4H)-yl)methyl]piperidine-1-carboxylate obtained in Step 1 and 2-fluoro-5-iodobenzonitrile.

ESI-MS m/z: 466 (M+H)+

Step 3: The title Compound (13 mg, yield: 71%) was obtained in the same manner as in Example 45 using tert-butyl 4-{[1-(3-cyano-4-fluorophenyl)-2-oxo-1,2-dihydropyrido[3,2-d]pyrimidin-3(4H)-yl]methyl}piperidine-1-carboxylate obtained in Step 2.

ESI-MS m/z: 538 (M+H)+, 1H-NMR (400 MHz, DMSO-$d_6$, δ): 9.14 (s, 1H), 8.72 (s, 1H), 8.46 (s, 1H), 8.26 (s, 1H), 8.17 (dd, J=4.8, 1.2 Hz, 1H), 8.06 (dd, J=6.0, 2.8 Hz, 1H), 7.89-7.65 (m, 2H), 7.70 (t, J=9.0 Hz, 1H), 7.15 (dd, J=8.4, 3.6 Hz, 1H), 6.59 (d, J=8.4 Hz, 1H), 4.73 (s, 2H), 4.50 (d, J=13 Hz, 2H), 3.49-3.20 (m, 4H), 2.35-2.13 (m, 1H), 1.89 (d, J=11 Hz, 2H), 1.53-1.30 (m, 2H)

Example 47

2-Fluoro-5-(2-oxo-3-{[1-(4-oxo-3,4-dihydropyrido[4,3-d]pyrimidin-5-yl)piperidin-4-yl]methyl}-3,4-dihydropyrido[2,3-d]pyrimidin-1(2H)-yl)benzonitrile (Compound 47)

Step 1: Tert-butyl 4-{[1-(3-cyano-4-fluorophenyl)-2-oxo-1,2-dihydropyrido[2,3-d]pyrimidin-3(4H)-yl]methyl}piperidine-1-carboxylate (350 mg, yield: 52%) was obtained in the same manner as in Example 6 using tert-butyl 4-[(2-oxo-1,2-dihydropyrido[2,3-d]pyrimidin-3(4H)-yl)methyl]piperidine-1-carboxylate obtained in Step 1 of Example 22 and 2-fluoro-5-iodobenzonitrile.

ESI-MS m/z: 466 (M+H)+

Step 2: The title Compound 47 (40 mg, yield: 56%) was obtained in the same manner as in Example 34 using tert-butyl 4-{[1-(3-cyano-4-fluorophenyl)-2-oxo-1,2-dihydropyrido[2,3-d]pyrimidin-3(4H)-yl]methyl}piperidine-1-carboxylate obtained in Step 1 and 5-chloropyrido[4,3-d]pyrimidin-4(3H)-one.

ESI-MS m/z: 511 (M+H)+, 1H-NMR (400 MHz, DMSO-$d_6$, δ): 12.1 (s, 1H), 8.23 (d, J=5.2 Hz, 1H), 8.11 (s, 1H), 8.03 (d, J=5.2 Hz, 1H), 7.94 (dd, J=6.0, 2.4 Hz, 1H), 7.74-7.66 (m, 2H), 7.61 (t, J=8.8 Hz, 1H) 7.04 (dd, J=8.0, 4.8 Hz, 1H), 6.82 (d, J=5.2 Hz, 1H), 4.64 (s, 2H), 3.90-3.87 (m, 2H), 3.35-3.33 (m, 2H), 2.87 (t, J=8.4 Hz, 2H), 1.99 (br s, 1H), 1.73-1.70 (m, 2H), 1.43-1.38 (m, 2H)

Example 48

4-(6-Methoxy-2-oxo-3-{[1-(4-oxo-3,4-dihydropyrido[4,3-d]pyrimidin-5-yl)piperidin-4-yl]methyl}-3,4-dihydroquinazolin-1(2H)-yl)picolinamide (Compound 48)

Step 1: Tert-butyl 4-[(6-methoxy-2-oxo-1,2-dihydroquinazolin-3(4H)-yl)methyl]piperidine-1-carboxylate (1.5 g, yield: 73%) was obtained in the same manner as in Reference Example 1 using 5-methoxy-2-nitrobenzaldehyde.

ESI-MS m/z: 376 (M+H)+, 1H-NMR (400 MHz, DMSO-$d_6$, δ): 8.97 (s, 1H), 6.75-6.69 (m, 3H), 4.38 (s, 2H), 3.93-3.90 (m, 2H), 3.90 (s, 3H), 3.18 (d, J=7.2 Hz, 2H), 2.68 (br s, 2H), 1.84 (br s, 1H), 1.58-1.55 (m, 2H), 1.39 (s, 9H), 1.07-1.00 (m, 2H)

Step 2: Tert-butyl 4-{[1-(2-cyanopyridin-4-yl)-6-methoxy-2-oxo-1,2-dihydroquinazolin-3(4H)-yl]methyl}piperidine-1-carboxylate (580 mg, yield: 76%) was obtained in the same manner as in Example 6 using tert-butyl 4-[(6-methoxy-2-oxo-1,2-dihydroquinazolin-3(4H)-yl)methyl]piperidine-1-carboxylate obtained in Step 1 and 4-iodopyridine-2-carbonitrile.

ESI-MS m/z: 478 (M+H)+

Step 3: 4-(6-Methoxy-2-oxo-3-{[1-(4-oxo-3,4-dihydropyrido[4,3-d]pyrimidin-5-yl)piperidin-4-yl]methyl}-3,4-dihydroquinazolin-1(2H)-yl)picolinonitrile (300 mg, yield: 47%) was obtained in the same manner as in Example 36 after performing a treatment in the same manner as in Step 4 of Reference Example 1 using tert-butyl 4-{[1-(2-cyanopyridin-4-yl)-6-methoxy-2-oxo-1,2-dihydroquinazolin-3(4H)-yl]methyl}piperidine-1-carboxylate obtained in Step 2.

ESI-MS m/z: 523 (M+H)$^+$, $^1$H-NMR (400 MHz, DMSO-d$_6$, δ): 12.1 (s, 1H), 8.82 (d, J=5.2 Hz, 1H), 8.22 (d, J=5.2 Hz, 1H), 8.17 (s, 1H), 8.11 (s, 1H), 7.80 (d, J=5.2 Hz, 1H), 6.91 (s, 1H), 6.82 (d, J=5.2 Hz, 1H), 6.75-6.73 (m, 1H), 6.39-6.37 (m, 1H), 4.57 (s, 2H), 3.89-3.77 (m, 2H), 3.73 (s, 3H), 3.34-3.32 (m, 2H), 2.89-2.83 (m, 2H), 1.96 (br s, 1H), 1.67-1.66 (m, 2H), 1.43-1.34 (m, 2H)

Step 4: 4-(6-Methoxy-2-oxo-3-{[1-(4-oxo-3,4-dihydropyrido[4,3-d]pyrimidin-5-yl)piperidin-4-yl]methyl}-3,4-dihydroquinazolin-1(2H)-yl)picolinonitrile (80 mg, 0.15 mmol) obtained in Step 3 and lithium hydroxide monohydrate (14 mg, 0.33 mmol) were stirred in a tetrahydrofuran-water mixed solvent (1/1, 3.0 mL) at room temperature for 15 hours. The reaction mixture was concentrated under reduced pressure, and the resulting residue was purified by preparative reverse-phase HPLC, whereby the title Compound 48 (34 mg, yield: 40%) was obtained.

ESI-MS m/z: 541 (M+H)$^+$, $^1$H-NMR (400 MHz, DMSO-d$_6$+D$_2$O, δ): 8.73 (d, J=5.2 Hz, 1H), 8.32-8.17 (m, 2H), 8.08 (s, 1H), 7.94 (s, 1H), 7.74-7.69 (m, 1H), 7.62 (d, J=4.4 Hz, 1H), 7.06 (s, 1H), 6.90 (s, 1H), 6.82 (d, J=5.6 Hz, 1H), 6.76-6.66 (m, 1H), 6.21 (d, J=8.4 Hz, 1H), 4.56 (s, 2H), 3.83 (d, J=13 Hz, 2H), 3.67 (s, 3H), 3.31 (d, J=7.2 Hz, 2H), 2.92-2.80 (m, 2H), 2.05-1.82 (m, 1H), 1.76-1.58 (m, 2H), 1.45-1.27 (m, 2H)

Example 49

4-(6-Fluoro-2-oxo-3-{[1-(4-oxo-3,4-dihydropyrido[4,3-d]pyrimidin-5-yl)piperidin-4-yl]methyl}-3,4-dihydroquinazolin-1(2H)-yl)picolinonitrile (Compound 49)

Step 1: Tert-butyl 4-[(6-fluoro-2-oxo-1,2-dihydroquinazolin-3(4H)-yl)methyl]piperidine-1-carboxylate (720 mg, yield: 73%) was obtained in the same manner as in Reference Example 1 using 5-fluoro-2-nitrobenzaldehyde.

ESI-MS m/z: 364 (M+H)$^+$

Step 2: Tert-butyl 4-{[1-(2-cyanopyridin-4-yl)-6-fluoro-2-oxo-1,2,3,4-tetrahydroquinazolin-3-yl]methyl}piperidine-1-carboxylate (500 mg, yield: 78%) was obtained in the same manner as in Example 6 using tert-butyl 4-[(6-fluoro-2-oxo-1,2-dihydroquinazolin-3(4H)-yl)methyl]piperidine-1-carboxylate obtained in Step 1 and 4-iodopicolinonitrile.

ESI-MS m/z: 466 (M+H)$^+$

Step 3: The title Compound 49 (80 mg, yield: 54%) was obtained in the same manner as in Example 34 after performing a treatment in the same manner as in Step 4 of Reference Example 1 using tert-butyl 4-{[1-(2-cyanopyridin-4-yl)-6-fluoro-2-oxo-1,2,3,4-tetrahydroquinazolin-3-yl]methyl}piperidine-1-carboxylate obtained in Step 2.

ESI-MS m/z: 511 (M+H)$^+$, $^1$H-NMR (300 MHz, DMSO-d$_6$, δ): 9.87 (br s, 1H), 8.86 (d, J=5.1 Hz, 1H), 8.27-8.14 (m, 2H), 8.11 (s, 1H), 7.85-7.77 (m, 1H), 7.25-7.15 (m, 1H), 7.04-6.91 (m, 1H), 6.81 (d, J=5.4 Hz, 1H), 6.46-6.34 (m, 1H), 4.61 (s, 2H), 3.87 (d, J=13 Hz, 2H), 3.45-3.21 (m, 2H), 2.86 (t, J=12 Hz, 2H), 2.08-1.82 (m, 1H), 1.78-1.61 (m, 2H), 1.51-1.29 (m, 2H)

Example 50

N-[4-(4-{[1-(2-Cyanopyridin-4-yl)-2-oxo-1,2-dihydropyrido[2,3-d]pyrimidin-3(4H)-yl]methyl}piperidin-1-yl) quinazolin-6-yl]acetamide (Compound 50)

Step 1: Tert-butyl 4-[(2-oxo-1,2-dihydropyrido[2,3-d]pyrimidin-3(4H)-yl)methyl]piperidine-1-carboxylate (2.0 g, 5.8 mmol) obtained in Step 1 of Example 22, 4-iodopicolinonitrile (2.0 g, 8.7 mmol), copper(I) oxide (3.4 g, 24 mmol) and tripotassium phosphate (2.6 g, 12 mmol) were stirred in DMA (20 mL) at 120° C. for 7 hours. The reaction mixture was diluted with dichloromethane and extracted by adding water thereto. The organic layer was washed with saturated brine and dried over anhydrous magnesium sulfate, and then, the solvent was evaporated under reduced pressure. The resulting residue was purified by silica gel column chromatography (a dichloromethane/methanol mixed solvent), whereby tert-butyl 4-{[1-(2-cyanopyridin-4-yl)-2-oxo-1,2-dihydropyrido[2,3-d]pyrimidin-3(4H)-yl]methyl}piperidine-1-carboxylate (1.6 g, yield: 61%) was obtained.

$^1$H-NMR (300 MHz, DMSO-d$_6$, δ): 8.83 (d, J=5.4 Hz, 1H), 8.12 (d, J=1.5 Hz, 1H), 8.05 (dd, J=5.4, 1.5 Hz, 1H), 7.75 (dd, J=5.4, 2.1 Hz, 1H), 7.69 (d, J=7.2 Hz, 1H), 7.09 (dd, J=7.2, 2.1 Hz, 1H), 4.62 (s, 2H), 4.10-3.80 (m, 2H), 3.45-3.15 (m, 2H), 2.90-2.50 (m, 2H), 2.00-1.75 (m, 1H), 1.70-1.50 (m, 2H), 1.38 (s, 9H), 1.15-0.90 (m, 2H)

Step 2: 4-(3-{[1-(6-Bromoquinazolin-4-yl)piperidin-4-yl]methyl}-2-oxo-3,4-dihydropyrido[2,3-d]pyrimidin-1(2H)-yl)picolinonitrile (100 mg, yield: 76%) was obtained in the same manner as in Step 3 of Example 5 using tert-butyl 4-{[1-(2-cyanopyridin-4-yl)-2-oxo-1,2-dihydropyrido[2,3-d]pyrimidin-3(4H)-yl]methyl}piperidine-1-carboxylate obtained in Step 1 and 6-bromo-4-chloroquinazoline.

ESI-MS m/z: 555 (M+H)$^+$

Step 3: The title Compound 50 (25 mg, yield: 26%) was obtained in the same manner as in Step 3 of Example 33 using 4-(3-{[1-(6-bromoquinazolin-4-yl)piperidin-4-yl]methyl}-2-oxo-3,4-dihydropyrido[2,3-d]pyrimidin-1(2H)-yl)picolinonitrile obtained in Step 2 and acetamide.

ESI-MS m/z: 534 (M+H)$^+$, $^1$H-NMR (400 MHz, DMSO-d$_6$, δ): 10.3 (s, 1H), 8.84 (d, J=5.2 Hz, 1H), 8.55 (s, 1H), 8.47 (s, 1H), 8.15 (s, 1H), 8.07 (d, J=4.8 Hz, 1H), 7.85-7.77 (m, 4H), 7.13-7.10 (m, 1H), 4.68 (s, 2H), 4.27-4.23 (m, 2H), 3.42 (d, J=6.8 Hz, 2H), 3.08 (t, J=13 Hz, 2H), 2.12 (br s, 4H), 1.87-1.84 (m, 2H), 1.51-1.45 (m, 2H)

Example 51

4-(6-Cyano-2-oxo-3-{[1-(4-oxo-3,4-dihydropyrido[4,3-d]pyrimidin-5-yl)piperidin-4-yl]methyl}-3,4-dihydroquinazolin-1(2H)-yl)picolinamide (Compound 51)

Step 1: Tert-butyl 4-{[(5-bromo-2-nitrobenzyl)amino]methyl}piperidine-1-carboxylate (7.0 g, yield: 63%) was obtained in the same manner as in Step 1 of Reference Example 1 using 5-bromo-2-nitrobenzaldehyde.

$^1$H-NMR (300 MHz, CDCl$_3$, δ): 7.84 (d, J=8.4 Hz, 2H), 7.60-7.50 (m, 1H), 5.30 (s, 1H), 4.22-4.05 (m, 2H), 4.03 (s, 2H), 2.79-2.60 (m, 2H), 2.52 (d, J=6.6 Hz, 2H), 1.80-1.50 (m, 2H), 1.46 (s, 9H), 1.22-1.02 (m, 2H)

Step 2: Tert-butyl 4-{[(5-bromo-2-nitrobenzyl)amino]methyl}piperidine-1-carboxylate (3.0 g, 7.0 mmol) obtained in Step 1, zinc (1.5 mg), zinc cyanide (540 mg, 4.6 mmol)

and tetrakis(triphenylphosphine)palladium(0) (100 mg, 0.09 mmol) were stirred in DMF (100 mL) at 100° C. for 12 hours. To the reaction mixture, water was added, and the resulting mixture was extracted with ethyl acetate. The organic layer was washed with saturated brine and dried over anhydrous magnesium sulfate. Then, a residue obtained by evaporating the solvent under reduced pressure was purified by silica gel column chromatography (a hexane/ethyl acetate mixed solvent), whereby tert-butyl 4-{[(5-cyano-2-nitrobenzyl)amino]methyl}piperidine-1-carboxylate (1.2 g, yield: 46%) was obtained.

$^1$H-NMR (300 MHz, CDCl$_3$, δ): 8.09 (s, 1H), 8.01 (d, J=8.4 Hz, 1H), 7.80-7.68 (m, 1H), 4.25-4.00 (m, 4H), 3.50 (s, 1H), 2.71 (t, J=12 Hz, 2H), 2.54 (d, J=3.3 Hz, 2H), 1.80-1.60 (m, 2H), 1.75-1.51 (m, 1H), 1.47 (s, 9H), 1.29-1.01 (m, 2H)

Step 3: Tert-butyl 4-[(6-cyano-2-oxo-1,2-dihydroquinazolin-3(4H)-yl)methyl]piperidine-1-carboxylate (600 mg, yield: 70%) was obtained in the same manner as in Reference Example 1 using tert-butyl 4-{[(5-cyano-2-nitrobenzyl)amino]methyl}piperidine-1-carboxylate obtained in Step 2.

$^1$H-NMR (300 MHz, CDCl$_3$, δ): 7.58 (s, 1H), 7.52-7.41 (m, 1H), 7.34 (s, 1H), 6.76 (d, J=8.4 Hz, 1H), 4.48 (s, 2H), 4.25-4.01 (m, 2H), 3.45-3.25 (m, 2H), 2.80-2.59 (m, 2H), 2.00-1.55 (m, 3H), 1.45 (s, 9H), 1.33-1.10 (m, 2H)

Step 4: Tert-butyl 4-{[6-cyano-1-(2-cyanopyridin-4-yl)-2-oxo-1,2,3,4-tetrahydroquinazolin-3-yl]methyl}piperidine-1-carboxylate (220 mg, yield: 57%) was obtained in the same manner as in Example 6 using tert-butyl 4-[(6-cyano-2-oxo-1,2-dihydroquinazolin-3(4H)-yl)methyl]piperidine-1-carboxylate obtained in Step 3 and 4-iodopicolinonitrile.

ESI-MS m/z: 473 (M+H)$^+$

Step 5: 1-(2-Cyanopyridin-4-yl)-2-oxo-3-{[1-(4-oxo-3,4-dihydropyrido[4,3-d]pyrimidin-5-yl)piperidin-4-yl]methyl}-1,2,3,4-tetrahydroquinazoline-6-carbonitrile (55 mg, yield: 26%) was obtained by performing the same treatments as in Step 4 of Reference Example 1 and Example 34 sequentially using tert-butyl 4-{[6-cyano-1-(2-cyanopyridin-4-yl)-2-oxo-1,2,3,4-tetrahydroquinazolin-3-yl]methyl}piperidine-1-carboxylate obtained in Step 4.

ESI-MS m/z: 518 (M+H)$^+$, $^1$H-NMR (300 MHz, DMSO-d$_6$, δ): 12.1 (br s, 1H), 8.91 (d, J=5.1 Hz, 1H), 8.25-8.18 (m, 2H), 8.10 (s, 1H), 7.86-7.73 (m, 2H), 7.62-7.52 (m, 1H), 6.81 (d, J=5.4 Hz, 1H), 6.46 (d, J=5.4 Hz, 1H), 4.67 (s, 2H), 3.88 (d, J=13 Hz, 2H), 3.40-3.27 (m, 2H), 2.95-2.78 (m, 2H), 2.05-1.85 (m, 1H), 1.77-1.63 (m, 2H), 1.49-1.30 (m, 2H)

Step 6: The title Compound 51 (28 mg, yield: 74%) was obtained in the same manner as in Step 4 of Example 48 using 1-(2-cyanopyridin-4-yl)-2-oxo-3-{[1-(4-oxo-3,4-dihydropyrido[4,3-d]pyrimidin-5-yl)piperidin-4-yl]methyl}-1,2,3,4-tetrahydroquinazoline-6-carbonitrile obtained in Step 5.

ESI-MS m/z: 536 (M+H)$^+$, $^1$H-NMR (400 MHz, DMSO-d$_6$, δ): 12.1 (br s, 1H), 8.81 (d, J=5.2 Hz, 1H), 8.22 (d, J=5.2 Hz, 2H), 8.10 (s, 1H), 8.00 (s, 1H), 7.78 (s, 2H), 7.28-7.66 (m, 1H), 7.55 (d, J=8.4 Hz, 1H), 6.82 (d, J=5.2 Hz, 1H), 6.33 (d, J=8.4 Hz, 1H), 4.68 (s, 2H), 3.88 (d, J=13 Hz, 2H), 3.34-3.32 (m, 2H), 2.87 (m, 2H), 2.05-1.93 (m, 1H), 1.82-1.62 (m, 2H), 1.45-1.29 (m, 2H)

Example 52

4-(4-{[1-(3-Cyano-4-fluorophenyl)-2-oxo-1,2-dihydropyrido[4,3-d]pyrimidin-3(4H)-yl]methyl}piperidin-1-yl)pyrido[4,3-d]pyrimidine-7-carboxamido Step 1: Tert-butyl 4-[(2-oxo-1,2-dihydropyrido[4,3-d]pyrimidin-3(4H)-yl)methyl]piperidine-1-carboxylate (3.6 g, yield: 61%) was obtained in the same manner as in Reference Example 1 using 4-aminonicotinaldehyde.

ESI-MS m/z: 347 (M+H)$^+$

Step 2: Tert-butyl 4-{[1-(3-cyano-4-fluorophenyl)-2-oxo-1,2-dihydropyrido[4,3-d]pyrimidin-3(4H)-yl]methyl}piperidine-1-carboxylate (450 mg, yield: 70%) was obtained in the same manner as in Step 1 of Example 50 using tert-butyl 4-[(2-oxo-1,2-dihydropyrido[4,3-d]pyrimidin-3(4H)-yl)methyl]piperidine-1-carboxylate obtained in Step 1 and 2-fluoro-5-iodobenzonitrile.

ESI-MS m/z: 449 (M+H)$^+$

Step 3: 5-(3-{[1-(7-Chloropyrido[4,3-d]pyrimidin-4-yl)piperidin-4-yl]methyl}-2-oxo-3,4-dihydropyrido[4,3-d]pyrimidin-1(2H)-yl)-2-fluorobenzonitrile (300 mg, 23%) was obtained in the same manner as in Step 3 of Example 5 using tert-butyl 4-{[1-(3-cyano-4-fluorophenyl)-2-oxo-1,2-dihydropyrido[4,3-d]pyrimidin-3(4H)-yl]methyl}piperidine-1-carboxylate obtained in Step 2 and Compound R11 obtained in Reference Example 11.

ESI-MS m/z: 529 (M+H)$^+$

Step 4: Propyl 4-(4-{[1-(3-cyano-4-fluorophenyl)-2-oxo-1,2-dihydropyrido[4,3-d]pyrimidin-3(4H)-yl]methyl}piperidin-1-yl)pyrido[4,3-d]pyrimidine-7-carboxylate (130 mg, yield: 53%) was obtained in the same manner as in Step 2 of Example 15 using 5-(3-{[1-(7-chloropyrido[4,3-d]pyrimidin-4-yl)piperidin-4-yl]methyl}-2-oxo-3,4-dihydropyrido[4,3-d]pyrimidin-(2H)-yl)-2-fluorobenzonitrile obtained in Step 3.

ESI-MS m/z: 581 (M+H)$^+$

Step 5: 4-(4-{[1-(3-Cyano-4-fluorophenyl)-2-oxo-1,2-dihydropyrido[4,3-d]pyrimidin-3(4H)-yl]methyl}piperidin-1-yl)pyrido[4,3-d]pyrimidine-7-carboxylic acid (35 mg, yield: 30%) was obtained in the same manner as in Step 3 of Example 15 using propyl 4-(4-{[1-(3-cyano-4-fluorophenyl)-2-oxo-1,2-dihydropyrido[4,3-d]pyrimidin-3(4H)-yl]methyl}piperidin-1-yl)pyrido[4,3-d]pyrimidine-7-carboxylate obtained in Step 4.

ESI-MS m/z: 539 (M+H)$^+$, $^1$H-NMR (400 MHz, DMSO-d$_6$, δ): 9.32 (s, 1H), 8.67 (s, 1H), 8.37 (s, 1H), 8.20 (d, J=5.6 Hz, 1H), 8.15-8.05 (m, 2H), 7.89-7.72 (m, 1H), 7.72 (t, J=9.0 Hz, 1H), 6.17 (d, J=5.6 Hz, 1H), 4.71 (s, 2H), 4.57 (d, J=13 Hz, 2H), 3.49-3.20 (m, 4H), 2.31-2.12 (m, 1H), 1.88 (d, J=10 Hz, 2H), 1.51-1.33 (m, 2H)

Step 6: The title Compound 52 (12 mg, yield: 34%) was obtained in the same manner as in Step 5 of Example 45 using 4-(4-{[1-(3-cyano-4-fluorophenyl)-2-oxo-1,2-dihydropyrido[4,3-d]pyrimidin-3(4H)-yl]methyl}piperidin-1-yl)pyrido[4,3-d]pyrimidine-7-carboxylic acid obtained in Step 5.

ESI-MS m/z: 538 (M+H)$^+$, $^1$H-NMR (300 MHz, DMSO-d$_6$, δ): 9.23 (s, 1H), 8.65 (s, 1H), 8.33 (s, 1H), 8.25-8.13 (m, 2H), 8.08 (s, 1H), 8.11-8.00 (m, 1H), 7.85 (s, 1H), 7.85-7.62 (m, 2H), 6.13 (d, J=5.4 Hz, 1H), 4.67 (s, 2H), 4.54 (d, J=12 Hz, 2H), 3.58-3.00 (m, 4H), 2.25-2.12 (m, 1H), 1.85 (d, J=12 Hz, 2H), 1.51-1.30 (m, 2H)

Example 53

Tablets (Compound 53)

Tablets having the following ingredients are prepared according to the conventional manner. Compound 53 (40 g), lactose (286.8 g) and potato starch (60 g) are mixed, and a 10% aqueous hydroxypropyl cellulose solution (120 g) is added thereto. The resulting mixture is kneaded, granulated, dried, and then sized according to the conventional manner, whereby granules for tableting are prepared. Magnesium stearate (1.2 g) is added thereto and mixed therewith, and the resulting mixture is tableted using a tablet press with a pestle having a diameter of 8 mm (model RT-15, manufactured by Kikusui Seisakusho Ltd.), whereby tablets (containing 20 mg of the active ingredient per tablet) are obtained.

TABLE 8

| Formulation | |
|---|---|
| Compound 53 | 20 mg |
| Lactose | 143.4 mg |
| Potato starch | 30 mg |
| Hydroxypropyl cellulose | 6 mg |
| Magnesium stearate | 0.6 mg |
| | 200 mg |

INDUSTRIAL APPLICABILITY

According to the present invention, a fused-ring heterocyclic compound or a pharmaceutically acceptable salt thereof, which has a Wnt signaling inhibitory activity, and is useful as a therapeutic and/or preventive agent for, for example, cancer, pulmonary fibrosis, fibromatosis, osteoarthritis, and the like, and the like can be provided.

The invention claimed is:
1. A fused-ring heterocyclic compound represented by formula (I) or a pharmaceutically acceptable salt thereof:

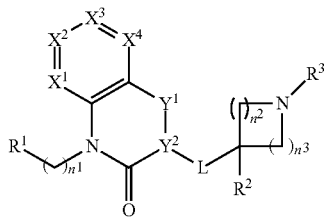

(I)

wherein:
$n^1$ represents 0 or 1;
$n^2$ and $n^3$ may be the same or different, and each represents 1 or 2;
when $n^1$ is 0, $R^1$ represents an optionally substituted aryl, an optionally substituted aromatic heterocyclic group, or an optionally substituted aliphatic heterocyclic group, and when $n^1$ is 1, $R^1$ represents an aryl substituted with cyano or carbamoyl, an optionally substituted aromatic heterocyclic group, or an optionally substituted aliphatic heterocyclic group;
$R^2$ represents a hydrogen atom or hydroxy;
$R^3$ represents an optionally substituted aromatic heterocyclic group or an optionally substituted aliphatic heterocyclic group;
$X^1$, $X^2$, $X^3$, and $X^4$ may be the same or different, and each represents N or $CR^4$;
each $R^4$ independently represents a hydrogen atom, a lower alkyl, cyano, a halogen, hydroxy, a lower alkoxy, a lower alkanoyl, or a lower alkylsulfonyl;
$Y^1$ represents $CH_2$ or $C(=O)$;
$Y^2$ represents CH or N; and
L represents $CH_2$ or NH.
2. The compound or pharmaceutically acceptable salt according to claim 1, wherein $n^2$ and $n^3$ are each 2.

3. The compound or pharmaceutically acceptable salt according to claim 1, wherein $Y^2$ is N, and L is $CH_2$.
4. The compound or pharmaceutically acceptable salt according to claim 1, wherein $Y^1$ is $CH_2$.
5. The compound or pharmaceutically acceptable salt according to claim 1, wherein $n^1$ is 0.
6. The compound or pharmaceutically acceptable salt according to claim 1, wherein:
when $n^1$ is 0, $R^1$ is (i) an optionally substituted phenyl, or (ii) an optionally substituted pyridyl, pyridonyl, or pyrimidinyl; and
when $n^1$ is 1, $R^1$ is (i) a phenyl substituted with cyano or carbamoyl, or (ii) an optionally substituted pyridyl, pyridonyl, or pyrimidinyl.
7. The compound or pharmaceutically acceptable salt according to claim 1, wherein $R^1$ is:
a group represented by formula (a1):

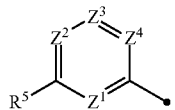

(a1)

wherein
when $n^1$ is 0:
$R^5$ represents a hydrogen atom, a $C_{1-10}$ alkyl which may be substituted with hydroxy, a $C_{1-10}$ alkoxycarbonyl, a $C_{2-11}$ alkanoyl, a $C_{1-10}$ alkylsulfonyl, a —$NR^{6a}R^{6b}$ wherein $R^{6a}$ and $R^{6b}$ may be the same or different, and each represents a hydrogen atom, a $C_{2-11}$ alkanoyl, or a $C_{1-10}$ alkyl, —$CONR^{6c}R^{6d}$ wherein $R^{6c}$ and $R^{6d}$ may be the same or different, and each represents a hydrogen atom or a $C_{1-10}$ alkyl, —$SO_2NR^{6e}R^{6f}$ wherein $R^{6e}$ and $R^{6f}$ may be the same or different, and each represents a hydrogen atom or a $C_{1-10}$ alkyl, a halogen, cyano, carboxy, or nitro; and
$Z^1$, $Z^2$, $Z^3$, and $Z^4$ may be the same or different, and each represents N or $CR^7$ wherein $R^7$ represents a hydrogen atom, carboxy, or a halogen; or
when $n^1$ is 1:
$R^5$ represents a carbamoyl or cyano; and
$Z^1$, $Z^2$, $Z^3$, and $Z^4$ may be the same or different, and each represents N or $CR^7$ wherein $R^7$ represents a hydrogen atom; or
a group represented by the following formula (a2):

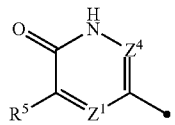

(a2)

wherein $R^5$, $Z^1$, and $Z^4$ are as defined above when $n^1$ is 0 and 1, respectively.
8. The compound or pharmaceutically acceptable salt according to claim 7, wherein:
when $n^1$ is 0, $R^5$ is cyano, —$CONH_2$, or —$SO_2NH_2$; and
when $n^1$ is 1 $R^5$ is cyano or —$CONH_2$.
9. The compound or pharmaceutically acceptable salt according to claim 7, wherein $R^5$ is cyano.
10. The compound or pharmaceutically acceptable salt according to claim 7, wherein:

when $n^1$ is 0, $R^7$ is a hydrogen atom or a fluorine atom; and when $n^1$ is 1, $R^7$ is a hydrogen atom.

11. The compound or pharmaceutically acceptable salt according to claim 1, wherein $R^3$ is an optionally substituted aromatic heterocyclic group.

12. The compound or pharmaceutically acceptable salt according to claim 11, wherein the aromatic heterocyclic group is a bicyclic aromatic heterocyclic group.

13. The compound or pharmaceutically acceptable salt according to claim 11, wherein the aromatic heterocyclic group is quinazolinyl.

14. The compound or pharmaceutically acceptable salt according to claim 1, wherein $R^3$ is an optionally substituted aliphatic heterocyclic group.

15. A pharmaceutical composition, comprising, as an active ingredient, the compound or pharmaceutically acceptable salt according to claim 1.

* * * * *